US010370450B2

(12) United States Patent
Fujikura et al.

(10) Patent No.: US 10,370,450 B2
(45) Date of Patent: Aug. 6, 2019

(54) ANTI-DR6 ANTIBODIES AND METHODS OF IMMUNE REGULATION

(71) Applicant: NATIONAL UNIVERSITY CORPORATION HOKKAIDO UNIVERSITY, Sapporo-shi (JP)

(72) Inventors: Daisuke Fujikura, Sapporo (JP); Toshimitsu Uede, Sapporo (JP)

(73) Assignee: National University Corporation Hokkaido University, Sapporo-Shi, Hokkaido (JP)

( * ) Notice: Subject to any disclaimer, the term of this patent is extended or adjusted under 35 U.S.C. 154(b) by 0 days.

(21) Appl. No.: 15/037,766

(22) PCT Filed: Nov. 19, 2014

(86) PCT No.: PCT/JP2014/080589
§ 371 (c)(1),
(2) Date: May 19, 2016

(87) PCT Pub. No.: WO2015/076282
PCT Pub. Date: May 28, 2015

(65) Prior Publication Data
US 2016/0289331 A1 Oct. 6, 2016

(30) Foreign Application Priority Data
Nov. 20, 2013 (JP) ................................. 2013-239500

(51) Int. Cl.
*A61K 39/395* (2006.01)
*C07K 16/28* (2006.01)
*C07K 14/705* (2006.01)
*G01N 33/50* (2006.01)
*A61K 38/00* (2006.01)
*A61K 39/00* (2006.01)

(52) U.S. Cl.
CPC .... *C07K 16/2878* (2013.01); *C07K 14/70578* (2013.01); *C07K 14/70596* (2013.01);
(Continued)

(58) Field of Classification Search
None
See application file for complete search history.

(56) References Cited

U.S. PATENT DOCUMENTS

| 2004/0043022 A1 | 3/2004 | Heuer et al. |
| 2004/0053022 A1 | 3/2004 | Ohlsson |
| 2012/0141456 A1* | 6/2012 | Mi ........................ C07K 14/00 424/130.1 |

FOREIGN PATENT DOCUMENTS

| JP | 2005-504380 | 2/2002 |
| JP | 2010-514700 | 5/2010 |

(Continued)

OTHER PUBLICATIONS

Cho et al., Uniique features of naive CD8+ T cell activation by IL-2, J. Immunol. 191:5559-5573, 2013.*
(Continued)

*Primary Examiner* — Claire Kaufman
(74) *Attorney, Agent, or Firm* — RatnerPrestia

(57) ABSTRACT

The problems: It is an object of the present invention to provide an immune regulating agent capable of modulating a receptor function concerning immune regulation of DR6, and a method for screening thereof.
The object aims to provide: The present invention relates to an immune regulating agent containing a physiologically active substance having an ability to bind specifically to DR6 and an ability to regulate signal transduction induced by specific binding between DR6 and Sdc1, as an active component. The immune regulating agent of the present invention can be used for treating or preventing diseases caused by excessive or abnormal immune response in mammals or diseases for which enhancement of immune function is desired in mammals, as an immune regulating agent based
(Continued)

on a hitherto unknown mechanism, capable of regulating signal transduction induced by specific binding between DR6 and Sdc1.

10 Claims, 27 Drawing Sheets

Specification includes a Sequence Listing.

(52) U.S. Cl.
CPC .......... *G01N 33/5041* (2013.01); *A61K 38/00* (2013.01); *A61K 2039/505* (2013.01); *C07K 2317/14* (2013.01); *C07K 2317/51* (2013.01); *C07K 2317/515* (2013.01); *C07K 2317/565* (2013.01); *C07K 2317/75* (2013.01); *C07K 2317/92* (2013.01); *C07K 2319/30* (2013.01); *G01N 2333/70578* (2013.01); *G01N 2333/70596* (2013.01); *G01N 2800/24* (2013.01)

(56) References Cited

FOREIGN PATENT DOCUMENTS

| WO | WO 99/43839 | 9/1999 | | |
|---|---|---|---|---|
| WO | WO 2008/080045 A2 | 7/2008 | | |
| WO | WO 2009080830 A1 | * 7/2009 | ....... | A61K 47/48384 |
| WO | WO 2010/062904 A2 | 6/2010 | | |
| WO | WO-2010062904 A2 | * 6/2010 | ............. | C07K 14/00 |

OTHER PUBLICATIONS

Sharma et al., Novel cancer immunotherapy agents with survival benefit: recent successes and next steps, Nat. Rev. Canc. 11:805-812, Nov. 2011.*
Klima et al., Novel cancer immunotherapy agents with survival benefit:recent successes and next steps , Mol. Immunol. 48:1439-1447, 2011.*
Perry et al., Murine models of systemic lupus erythematosus, J. Biomed. Biotech. vol. 2011, Article ID 271694, 19 pages, 2011. [Retrieved online: <URL: https://doi.org/10.1155/2011/271694>], [accessed on Mar. 21, 2019].*
Fujikura et al., Nature Communications, 8(13957):1-11 (2017).
Horwitz, Arthritis & Rheumatism, 62(8):2185-87 (2010).
Hu et al., FEBS Letters, 588:401-7 (2014).
Ohl and Tenbrock, Journal Biomedicine and Biotechnology, 1-14 (2011).
Supplementary European Search Report for Application No. 14864670.6, dated Jun. 26, 2017 by Zoran Cilensek.
Wang et al., Journal of Cell Science, 127:3257-68 (2014).
Jefferis et al., Immunol., 65:111-28 (1997).
Jones et al., Nature, 321:522-25 (1986).
Reiter et al., Protein Engineering, 7:697-704 (1994).
Riechmann et al. Nature, 332:323-27 (1988).
Verhoeyen et al., Science, 239:1534-36 (1988).
Wright et al., TibTECH, 15:26-32 (1997).
International Search Report for International Application No. PCT/JP2014/080589 dated Mar. 3, 2015 by the Japanese Patent Office.
Lamorte et al., Leukemia, 26:1801-90 (2012).
Mali et al., J. Biol. Chem., 265(12):6884-89 (1990).
Mi et al., Nature Medicine, 17(7):816-22 (2011).
Nikolaev et al., APP binds DR6 to trigger axon pruning and neuron death via distinct caspases, Supplementary Figures, 24 pages.
Nikolaev et al., Nature, 457:981-90 (2009).
Pan et al., FEBS Lett., 431:351-56 (1998).
Sasaroli et al., Cancer Biology & Therapy, 12(3):169-80 (2011).
Schmidt et al., J. Immunol., 175:2286-92 (2005).
Venkataraman et al., Immunol. Letter, 106:42-47 (2006).
Zhao et al., J. Exp. Med., 194(10):1441-48 (2001).
European Communication for European Application No. 14864670.6, dated Mar. 7, 2019, 6 pages.
European Result of Consultation for European Application No. 14864670.6, dated Mar. 21, 2019, 3 pages.

* cited by examiner

ANTI-DR6 ANTIBODIES AND METHODS OF IMMUNE REGULATION

CROSS-REFERENCE TO RELATED APPLICATIONS

This application is a U.S. National Phase application of PCT International Application PCT/JP2014/080589, filed Nov. 19, 2014 which claims priority to Japanese Application No. 2013-239500, filed Nov. 20, 2013, the contents of which are incorporated herein by reference in their entireties for all purposes.

TECHNICAL FIELD

The present invention relates to an immune regulating agent containing a substance capable of suppressing or inducing signal transduction resulting from the binding between death receptor 6 (DR6) and its ligand syndecan-1 (Sdc1), as an active component.

BACKGROUND OF THE INVENTION

DR6 is a member of a death receptor family, and is also called a TNF receptor super family member 21 (TNFRSF21), or TR9. DR6 is a type-I transmembrane receptor having four extracellular cysteine rich motifs and one cytoplasmic death domain structure (Non Patent Literature 1).

Expression of DR6 is observed in tissues such as heart, brain, placenta, pancreas, lymph node, thymus, prostatic tissue, skeletalmuscle, kidney and didymus, and plays an important role in various biological control mechanisms, and also relationships with diverse diseases have been indicated.

For example, the possibility that DR6 is an aggravating factor of multiple sclerosis has been indicated (Non Patent Literature 2). Also, the possibility that DR6 is an aggravating factor of asthma has been indicated (Non Patent Literature 3).

Also there has been reported that DR6 has a function of binding with amyloid precursor protein (APP) which is believed to cause Alzheimer's disease, and controlling cell death and defective axon elongation of nerve cells (Non Patent Literature 4), and there is a patent application directed to a DR6 antagonistic antibody which is to be a DR6 antagonist that inhibits or blocks the interaction between DR6 and APP (Patent Literature 1).

Meanwhile, it is known that DR6 is deeply involved in the control of the immune mechanism. For example, the above Non Patent Literature 1 reports that overexpression of DR6 in a specific cell strain into which a gene encoding DR6 is transduced causes the activation of both NF-kB and JNK, and apoptosis.

There has been also reported that in DR6 gene-deficient model mice, T cells do not substantially have a normal function in JNK activation, and when protein antigens are administered to DR6 (−/−) mice, T cells excessively proliferate, and show excessively strong deviation to Th2 response (Non Patent Literature 5).

Further, when a model of experimental autoimmune encephalomyelitis induced by myelin oligodendrocyte glycoprotein was used, DR6 (−/−) mice showed higher tolerance to both of the onset and the progression of CNS disease in comparison with wild-type littermates. That is, there is a possibility that DR6 is involved in the infiltration of leukocyte, and has a function of inducing and progressing experimental autoimmune encephalomyelitis (Non Patent Literature 6).

Thus, DR6 is believed to be an important receptor molecule which is a starting point of intracellular signal transduction concerning immune mechanism, particularly activation regulation of peripheral T-cell. Therefore, a molecule capable of modulating the receptor function concerning immune regulation of DR6 by specifically binding with DR6 is expected to become a trigger molecule that activates or suppresses immune function via signal transduction of DR6, and can be used as an immune regulating agent.

However, DR6 does not show binding affinity to known TNF ligand family molecules, and the true nature of DR6 ligand capable of inducing a signal concerning immune regulation by specifically binding to DR6 is still unknown.

Meanwhile, Sdc1, which is also called CD138 antigen, is a transmembrane heparan sulfate proteoglycan macromolecule (HSPG) that forms a syndecan family having homology with a transmembrane domain and a cytoplasmic domain, together with syndecan 2 which is also called fibroglycan, syndecan 3 which is also called N-syndecan, and syndecan 4 which is also called amphiglycan.

HSPG shows distribution specific for cell types, and is known to be involved in interaction with extracellular matrix proteins, cell surface molecules or soluble proteins such as cytokines. In the transmembrane domain and the intracellular domain, there exist four tyrosine residues of which positions are highly conserved, and the possibility of involvement in intracellular signal transduction by phosphorylation of any one of the tyrosine residues has been indicated.

A gene encoding human Sdc1 (hSdc1) has been already cloned (Non Patent Literature 7). hSdc1 consists of 310 amino acid residues, and includes an extracellular domain of amino acids at positions 1 to 251 followed by a hydrophobic transmembrane region of 25 amino acid residues (amino acids at positions 252 to 276), and a cytoplasmic domain of the last 34 amino acid residues (amino acids at positions 277 to 310). The amino acids at positions 1 to 17 form a secretion signal, which is understood as being useful when Sdc1 is secreted from a cell that biosynthesizes hSdc1, but not being necessary for physiological activity of hSdc1.

Meanwhile, the extracellular domain of hSdc1 includes five glycosaminoglycan (GAG) adherable sites at position 37, position 45, position 47, position 206 and position 216. Among these, the amino acid residues at position 45 and position 47 are known to lose the binding ability to heparan sulfate, and to simultaneously lose the physiological activity as hSdc1 when they are substituted with other amino acid residues.

However, it is unknown that specific binding between Sdc1 and DR6 is involved in suppression of T cell activation, namely Sdc1 is a physiological ligand of DR6 regarding regulation of immune response by DR6.

CITATION LIST

Non Patent Literature

Non Patent Literature 1: Pan et al., FEBS Lett., 1998, Vol. 431, pp. 351-356
Non Patent Literature 2: Mi et al., Nature medicine, 2011, Vol. 17, pp. 816-821
Non Patent Literature 3: Venkataraman et al., Immunol. Letter, 2006, Vol. 106, pp. 42-47

Non Patent Literature 4: Nikolaev et al., Nature, 2009, Vol. 457, pp. 981-989

Non Patent Literature 5: Zhao et al., J. Exp. Med., 2001, Vol. 194, pp. 1441-1448

Non Patent Literature 6: Schmidt et al., J. Immunol., 2005, Vol. 175, pp. 2286-2292

Non Patent Literature 7: Mali et al., J. Biol. Chem., 1990, Vol. 265, pp. 6884-6889

Patent Literature

Patent Literature 1: JP 2010-514700 W

SUMMARY OF THE INVENTION

Technical Problem

It is an object of the present invention to provide a molecule capable of modulating a receptor function concerning immune regulation of DR6 that can be used as an immune regulating agent, and a method for screening an immune regulating agent using DR6 and syndecan 1.

Solution to Problem

Through various studies, the present inventors found that Sdc1 is a DR6 ligand capable of specifically binding to DR6 and inducing signal transduction concerning immune regulation, and accomplished each aspect of the invention shown below.

(1) An immune regulating agent containing a physiologically active substance having an ability to bind specifically to DR6 and an ability to regulate signal transduction induced by specific binding between DR6 and Sdc1, as an active component.

(2) The immune regulating agent according to (1), wherein the physiologically active substance is Sdc1 or a functional equivalent thereof.

(3) The immune regulating agent according to (2), wherein the physiologically active substance is a polypeptide consisting of any one of the following amino acid sequences of a) to d):

a) a polypeptide consisting of the amino acid sequence represented by SEQ ID NO: 6 or SEQ ID NO: 8;

b) a polypeptide consisting of an amino acid sequence in which one or several amino acids except for amino acids at position 45 and position 47 in the amino acid sequence represented by SEQ ID NO: 6 or SEQ ID NO: 8 are deleted and/or substituted, or an amino acid sequence in which one or several amino acids are added to the amino acid sequence represented by SEQ ID NO: 6 or SEQ ID NO: 8, and having an ability to bind specifically to DR6, c) a polypeptide consisting of the amino acid sequence represented by SEQ ID NO: 10 or SEQ ID NO: 12, and d) a polypeptide consisting of an amino acid sequence in which one or several amino acids except for amino acids at position 45 and position 47 in the amino acid sequence represented by SEQ ID NO: 10 or SEQ ID NO: 12 are deleted and/or substituted, or an amino acid sequence in which one or several amino acids are added to the amino acid sequence represented by SEQ ID NO: 10 or SEQ ID NO: 12, and having an ability to bind specifically to DR6.

(4) The immune regulating agent according to (1), wherein the physiologically active substance is an anti-DR6 agonist antibody or an anti-DR6 antagonist antibody that acts on signal transduction induced by specific binding between DR6 and Sdc1.

(5) The immune regulating agent according to (4), wherein the anti-DR6 agonist antibody is one or more anti-DR6 antibodies selected from the group consisting of a) to e):

a) an anti-DR6 antibody comprising a heavy chain CDR1 consisting of the amino acid sequence represented by SEQ ID NO: 14, a heavy chain CDR2 consisting of the amino acid sequence represented by SEQ ID NO: 16, a heavy chain CDR3 consisting of the amino acid sequence represented by SEQ ID NO: 18, a light chain CDR1 consisting of the amino acid sequence represented by SEQ ID NO: 20, a light chain CDR2 of which the amino acid sequence is Trp-Ala-Ser, and a light chain CDR3 consisting of the amino acid sequence represented by SEQ ID NO: 22, b) an anti-DR6 antibody comprising a heavy chain CDR1 consisting of the amino acid sequence represented by SEQ ID NO: 24, a heavy chain CDR2 consisting of the amino acid sequence represented by SEQ ID NO: 26, a heavy chain CDR3 consisting of the amino acid sequence represented by SEQ ID NO: 28, a light chain CDR1 consisting of the amino acid sequence represented by SEQ ID NO: 30, a light chain CDR2 of which the amino acid sequence is Tyr-Ala-Ser, and a light chain CDR3 consisting of the amino acid sequence represented by SEQ ID NO: 32, c) an anti-DR6 antibody comprising a heavy chain CDR1 consisting of the amino acid sequence represented by SEQ ID NO: 34, a heavy chain CDR2 consisting of the amino acid sequence represented by SEQ ID NO: 36, a heavy chain CDR3 consisting of the amino acid sequence represented by SEQ ID NO: 38, a light chain CDR1 consisting of the amino acid sequence represented by SEQ ID NO: 40, a light chain CDR2 of which the amino acid sequence is Trp-Ala-Ser, and a light chain CDR3 consisting of the amino acid sequence represented by SEQ ID NO: 42, d) an anti-DR6 antibody comprising a heavy chain CDR1 consisting of the amino acid sequence represented by SEQ ID NO: 44, a heavy chain CDR2 consisting of the amino acid sequence represented by SEQ ID NO: 46, a heavy chain CDR3 consisting of the amino acid sequence represented by SEQ ID NO: 48, a light chain CDR1 consisting of the amino acid sequence represented by SEQ ID NO: 50, a light chain CDR2 of which the amino acid sequence is Trp-Ala-Ser, and a light chain CDR3 consisting of the amino acid sequence represented by SEQ ID NO: 52, and e) an anti-DR6 antibody comprising a heavy chain CDR1 consisting of the amino acid sequence represented by SEQ ID NO: 54, a heavy chain CDR2 consisting of the amino acid sequence represented by SEQ ID NO: 56, a heavy chain CDR3 consisting of the amino acid sequence represented by SEQ ID NO: 58, a light chain CDR1 consisting of the amino acid sequence represented by SEQ ID NO: 60, a light chain CDR2 of which the amino acid sequence is Trp-Ala-Ser, and a light chain CDR3 consisting of the amino acid sequence represented by SEQ ID NO: 62.

(6) The immune regulating agent according to (4), wherein the anti-DR6 antagonist antibody is one or more anti-DR6 antibodies selected from the group consisting of f) and g):

f) an anti-DR6 antibody comprising a heavy chain CDR1 consisting of the amino acid sequence represented by SEQ ID NO: 64, a heavy chain CDR2 consisting of the amino acid sequence represented by SEQ ID NO: 66, a heavy chain CDR3 consisting of the amino acid sequence represented by SEQ ID NO: 68, a light chain CDR1 consisting of the amino acid sequence represented by SEQ ID NO: 70, a light chain CDR2 of which the amino acid sequence is Arg-Val-Ser, and a light chain CDR3 consisting of the amino acid sequence represented by SEQ ID NO: 72, and g) an anti-DR6 antibody comprising a heavy chain CDR1 consisting of the amino acid sequence represented by SEQ ID NO: 74, a heavy chain CDR2 consisting of the amino acid sequence represented by SEQ ID NO: 76, a heavy chain CDR3 consisting of the amino acid sequence represented by SEQ ID NO: 78, a light chain CDR1 consisting of the amino acid sequence represented by SEQ ID NO: 80, a light chain CDR2 of which the amino acid sequence is Trp-Ala-Ser, and a light chain CDR3 consisting of the amino acid sequence represented by SEQ ID NO: 82.

(7) A method for screening a physiologically active substance having an ability to regulate signal transduction induced by specific binding between DR6 and Sdc1, comprising the steps a) to e):

a) bringing DR6, a functional equivalent of DR6 or a protein comprising at least a functional extracellular domain of DR6, into co-presence with at least one of the polypeptides defined in (3) and a test substance, b) detecting signal transduction induced by specific binding between DR6, the functional equivalent of DR6 or the protein comprising at least a functional extracellular domain of DR6, and at least one of the polypeptides defined in (3) in step a), c) bringing DR6, a functional equivalent of DR6 or a protein comprising at least a functional extracellular domain of DR6, into co-presence with at least one of the polypeptides defined in (3) in the absence of a test substance, d) detecting signal transduction induced by specific binding between DR6, the functional equivalent of DR6 or the protein comprising at least a functional extracellular domain of DR6, and at least one of the polypeptides defined in (3) in step c), and e) comparing a detection result of step b) and a detection result of step d).

(8) The screening method according to (7), wherein DR6, the functional equivalent of DR6 or the protein comprising at least a functional extracellular domain of DR6 is expressed in an antigen presenting cell.

(9) The screening method according to (7) or (8), wherein detection of signal transduction is carried out by detection of interleukin 2 produced by an antigen presenting cell.

(10) A hybridoma cell strain selected from the group consisting of hybridoma cell strain clone 25-1 deposited under the accession number NITE BP-01729, hybridoma cell strain clone 177-1 deposited under the accession number NITE BP-01730, hybridoma cell strain clone 82-30 deposited under the accession number NITE BP-01731, hybridoma cell strain clone 186-18 deposited under the accession number NITE BP-01732, hybridoma cell strain clone 180-10 deposited under the accession number NITE BP-01733, hybridoma cell strain clone 46-15-23 deposited under the accession number NITE BP-01734, and hybridoma cell strain clone 100-11 deposited under the accession number NITE BP-01735.

Advantageous Effects of Invention

According to the present invention, it is possible to provide an immune regulating agent based on an action mechanism that has not been known heretofore, and it allows the development of new therapeutic agents against autoimmune diseases such as rheumatism, systemic lupus erythematosus (SLE), multiple sclerosis, transplantation disease, Crohn disease, and ulcerative colitis, and allergic diseases such as pollinosis, atopy, and serious drug eruption.

DETAILED DESCRIPTION OF THE INVENTION

Figure 1:
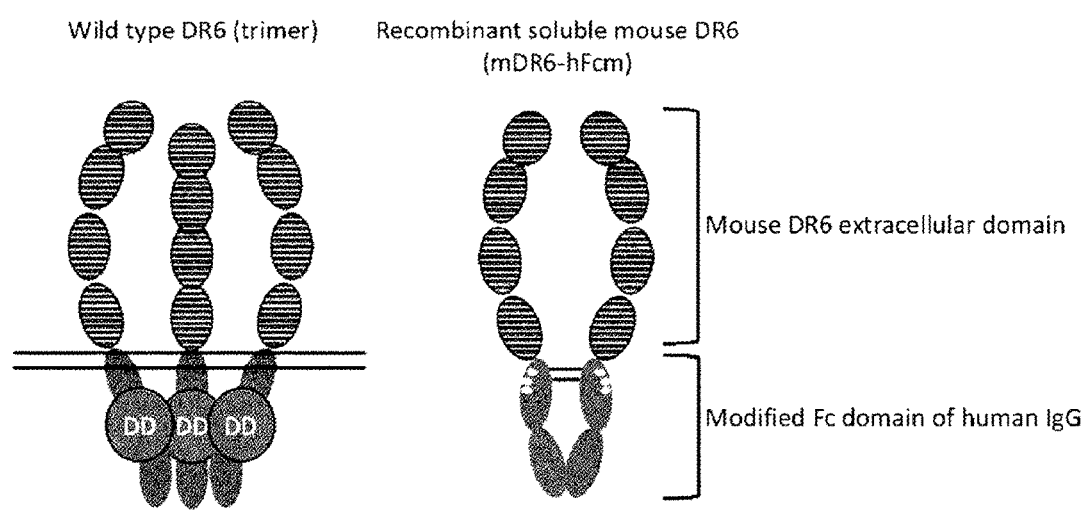
FIG. 1 includes schematic views showing the structures of wild-type DR6 and recombinant soluble mouse DR6 (mDR6-hFcm).

The present invention relates to an immune regulating agent containing a physiologically active substance having an ability to bind specifically to DR6 and an ability to regulate signal transduction induced by specific binding between DR6 and Sdc1, as an active component.

DR6 in the present invention refers to a type-I transmembrane receptor having four extracellular cysteine-rich motifs (CRD1 to CRD4) and one cytoplasmic death domain structure. Human DR6 (hDR6) is a protein consisting of a total of 655 amino acid residues consisting of the amino acid sequence represented by SEQ ID NO: 2 reported in Non Patent Literature 1, and includes a predicted signal sequence (amino acids at positions 1-41), an extracellular domain (amino acids at positions 42-211), a transmembrane domain (amino acids at positions 351-370) and a cytoplasmic domain (amino acids at positions 371-655). Mouse DR6 (mDR6) is a protein consisting of a total of 655 amino acid residues consisting of the amino acid sequence represented by SEQ ID NO: 4 reported in Non Patent Literature 5, and has 88% amino acid sequence identity with the amino acid sequence of hDR6.

The term DR6 used herein includes naturally occurring DR6 mutants encoded by so-called gene polymorphs consisting of amino acid sequences partially different from SEQ ID NO: 2 or SEQ ID NO: 4, naturally occurring cleaved forms or secreted forms (for example, solubilized DR6 comprising an extracellular domain sequence), naturally occurring splicing variants and naturally occurring allelic variants. Herein, by DR6 alone means any of naturally occurring DR6 derived from any mammals including human. The DR6 may be isolated and purified from nature, or can be produced by genetic engineering techniques or chemical synthesis techniques.

The term "mutant" herein embraces, for example, in the case of DR6 consisting of the amino acid sequence represented by SEQ ID NO: 2 or SEQ ID NO: 4, DR6 or a fragment thereof, or an extracellular domain thereof consisting of an amino acid sequence having at least about 80% or more, preferably at least about 85% or more, more preferably at least about 90% or more, further preferably at least about 95% or more identity with the amino acid sequence represented by SEQ ID NO: 2 or SEQ ID NO: 4. The term "mutant" also embraces, for example, in the case of DR6 consisting of the amino acid sequence represented by SEQ ID NO: 2 or SEQ ID NO: 4, DR6 consisting of an amino acid sequence in which one or more amino acid residues are deleted, substituted and/or added in the amino acid sequence represented by SEQ ID NO: 2 or SEQ ID NO: 4, a polypeptide in which one or more amino acid residues are added to N-terminus or C-terminus of the amino acid sequence represented by SEQ ID NO: 2 or SEQ ID NO: 4, and DR6 in which one or more amino acid residues are deleted from N-terminus or C-terminus of the amino acid sequence represented by SEQ ID NO: 2 or SEQ ID NO: 4.

The amino acid sequence identity (%) means the maximum percent sequence identity obtained when amino acid sequences to be compared are aligned by using an appropriate software program that is ordinarily used by those skilled in the art, for example, a sequence comparing computer program ALIGN-2.

The hSdc1 herein consists of the amino acid sequence represented by SEQ ID NO: 6 reported in Non Patent Literature 7, and refers to a transmembrane heparan sulfate proteoglycan macromolecule consisting of a total of 310 amino acid residues in which heparan sulfate is bound at position 45 and position 47. Mouse Sdc1 (mSdc1) consists of the amino acid sequence represented by SEQ ID NO: 8, and refers to a transmembrane heparan sulfate proteoglycan macromolecule consisting of a total of 311 amino acid residues in which heparan sulfate is bound at position 45 and position 47.

The Sdc1 herein includes naturally occurring Sdc1 mutants encoded by so-called gene polymorphs consisting of an amino acid sequence partially different from SEQ ID NO: 6 or SEQ ID NO: 8, naturally occurring cleaved forms or secreted forms (for example, solubilized Sdc1 comprising an extracellular domain sequence), naturally occurring splicing variants and naturally occurring allelic variants. Herein, by Sdc1 alone means any of naturally occurring Sdc1 derived from any mammals including human. The Sdc1 may be isolated and purified from nature, or can be produced by genetic engineering techniques or chemical synthesis techniques.

Herein, the expression "signal transduction induced by specific binding between DR6 and Sdc1" refers to all or part of the chain reactions in a DR6-expressing cell, that is initiated by ligand-receptor interaction between these two molecules leading to suppression of immune cell (T cell) activation. In the case where DR6-expressing cell is T cell, the signal transduction can be monitored by measuring interleukin 2 (IL2) production level of the T cell. Also, since the signal transduction is achieved by interaction between an intracellular death domain of DR6 and other protein in the cell, the signal transduction referred in the present invention may be monitored by measuring changes in function, activity, form, chemical structure and the like of an intracellular molecule other than DR6 involved in the signal transduction.

The "an ability to regulate signal transduction" herein refers to the ability to initiate, enhance or amplify the aforementioned signal transduction, or the ability to prevent, inhibit, neutralize, block, stop, interrupt or attenuate the start of the signal transduction. Unless otherwise specified, in the present invention, the ability to initiate, enhance or amplify the signal transduction is expressed as an inductive ability, and the ability to prevent, inhibit, neutralize, block, stop, interrupt or attenuate the start of the signal transduction is expressed as a suppressive ability. A substance having an ability to bind to DR6 and the inductive ability is referred to as a DR6 agonist, and a substance having an ability to bind to DR6 and the suppressive ability is referred to as a DR6 antagonist.

The term "DR6 antagonist" or "DR6 agonist" is used in its broadest meaning, and includes any molecules that regulate signal transduction leading to suppression of T cell activation by binding between DR6 and Sdc1 in any of in vitro, in situ, or ex vivo.

The DR6 antagonist or the DR6 agonist intended as the present invention includes anti-DR6 antibodies, Sdc1, Sdc1 mutants, solubilized Sdc1, solubilized Sdc1 mutants or fusion proteins consisting of these and other protein, multimers of these, or low molecular compounds that bind with DR6 to suppress binding between DR6 and Sdc1.

Therefore, one aspect of the "immune regulating agent" in the present invention includes an agonist or an antagonist having an ability to bind to DR6 andrelatingtosignaltransductionleadingtosuppressionofTcellactivityinitiated by specific binding between DR6 and Sdc1, for initiating, enhancing, amplifying, preventing, inhibiting, blocking, stopping, interrupting or attenuating immune response in which T cell activation is involved.

Another aspect of the "immune regulating agent" in the present invention includes substances having an ability to bind to Sdc1, for preventing, inhibiting, blocking, stopping, interrupting or attenuating signal introduction leading to suppression of T cell activity initiated by specific binding between DR6 and Sdc1.

Hereinafter, the present invention is further described by illustrating embodiments.

1. Agonist Immune Regulating Agent

In one embodiment of the present invention, there is provided an immune regulating agent having an ability to bind specifically to DR6, and an inductive ability of signal transduction leading to suppression of T cell activation induced by specific binding between DR6 and Sdc1. That is, the present embodiment relates to an immune regulating agent as a DR6 agonist, capable of binding to DR6 and inducing the signal transduction to suppress T cell activation.

1-a) Sdc1

One embodiment of a DR6 agonist which is an immune regulating agent of the present invention is hSdc1 which is a polypeptide consisting of the amino acid sequence represented by SEQ ID NO: 6, or mSdc1 consisting of the amino acid sequence represented by SEQ ID NO: 8.

The following studies (1) to (7) by the present inventors elucidated that mSdc1, a polypeptide consisting of the amino acid sequence represented by SEQ ID NO: 8, binds with mDR6 under physiological conditions thereby induces signal transduction leading to suppression of T cell activity.

(1) For screening a ligand molecule of DR6, a gene encoding mDR6 (SEQ ID NO: 3) was recombined to prepare recombinant soluble mDR6 (mDR6-hFcm). The recombinant protein is a dimer in which two fusion protein molecules consisting of a mDR6 extracellular region (amino acids at positions 1-350, SEQ ID NO: 88) and a human IgG Fc region are bound via a disulfide bond in the Fc regions. Also, for suppressing nonspecific binding, glutamic acid at position 233 in the Fc region of the human IgG is substituted with phenylalanine, and leucine at position 234 is substituted with valine, and leucine at position 235 is substituted with alanine. FIG. 1 illustrates schematic views of structures of wild-type DR6 and mDR6-hFcm.

Figure 2:
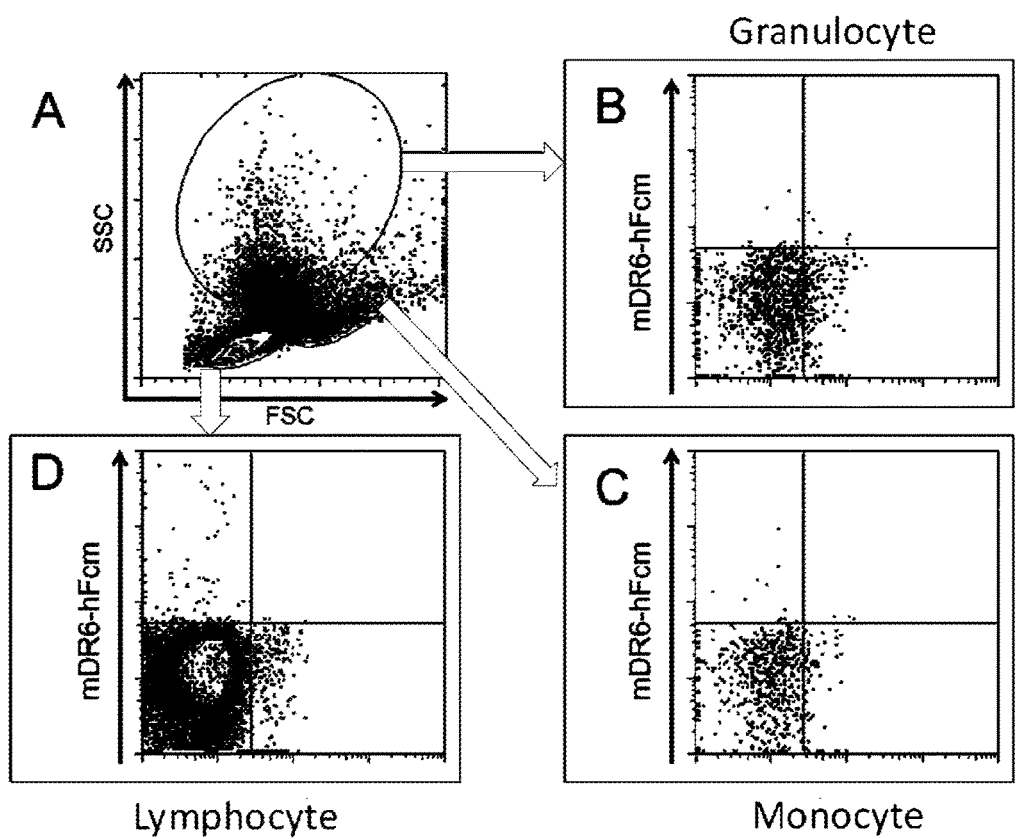
FIG. 2 includes charts showing the results of FACS analysis for naive cells derived from mouse spleen to which mDR6-hFcm is bound. DR6 ligand expressing cells are contained in a lymphocytes fraction.
Figure 3:
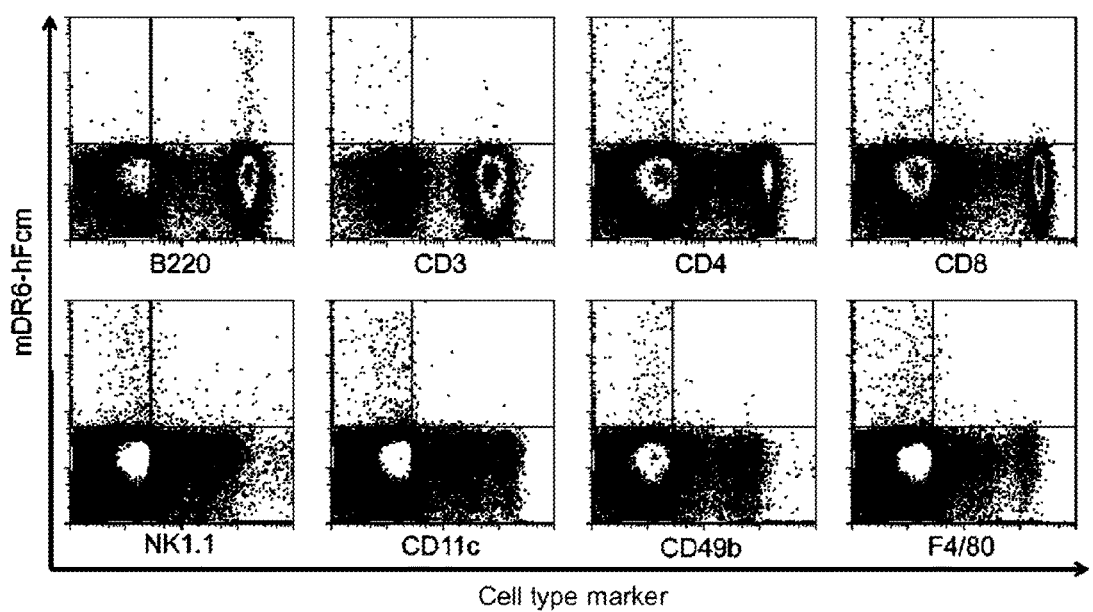
FIG. 3 includes charts showing the results of FACS analysis for DR6 ligand expressing cells stained with labelled antibodies against various cell specific marker proteins.

After staining naive cells derived from mouse spleen by using mDR6-hFcm labeled with APC (allophycocyanin) (labeled mDR6-hFcm), the cells were separated by FACS, and cells to which labeled mDR6-hFcm is bound, namely DR6 ligand expressing cells were detected in lymphocytes population (FIG. 2, panel D, left upper part of lymphocyte). Further, the DR6 ligand expressing cells were stained with labeled antibodies specific for cell specific marker proteins B220, CD3, CD4, CD8, NK1.1, CD11c, CD49b and F4/80 respectively. The DR6 ligand expressing cells were stained with a labeled antibody against B220 which is B cell specific marker protein (FIG. 3, right upper part of the B220 cells panel).

Figure 4:
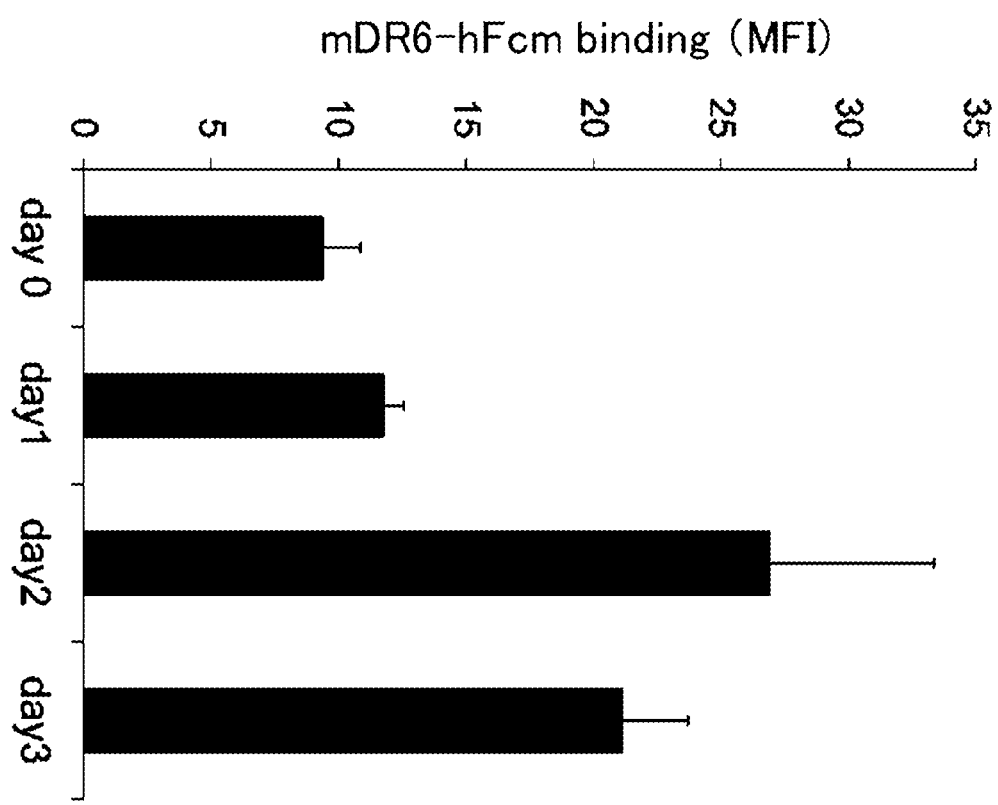
FIG. 4 is a graph showing the time course of the binding ability of LPS-stimulated B cells to mDR6-hFcm.
Figure 5:
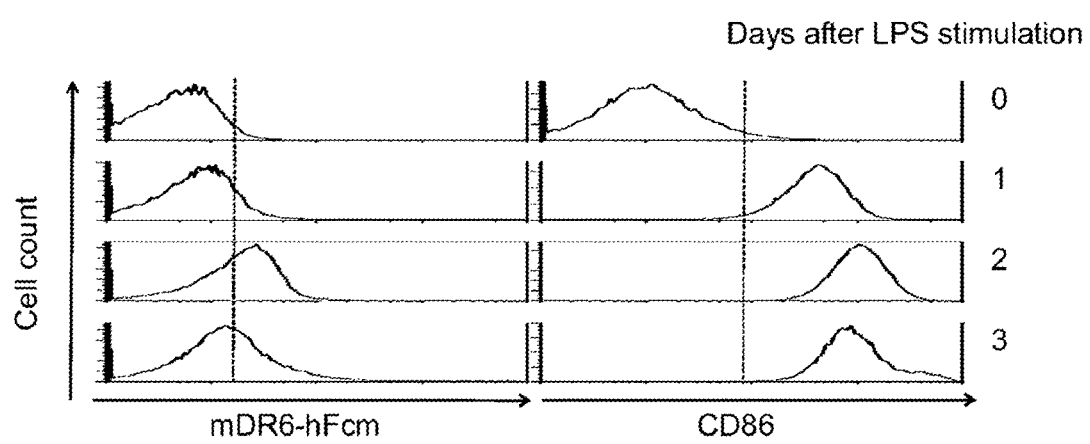
FIG. 5 is a graph showing the time course of the binding ability of LPS-stimulated B cells and the expression pattern of an activation marker CD86 in the cells.
Figure 6:
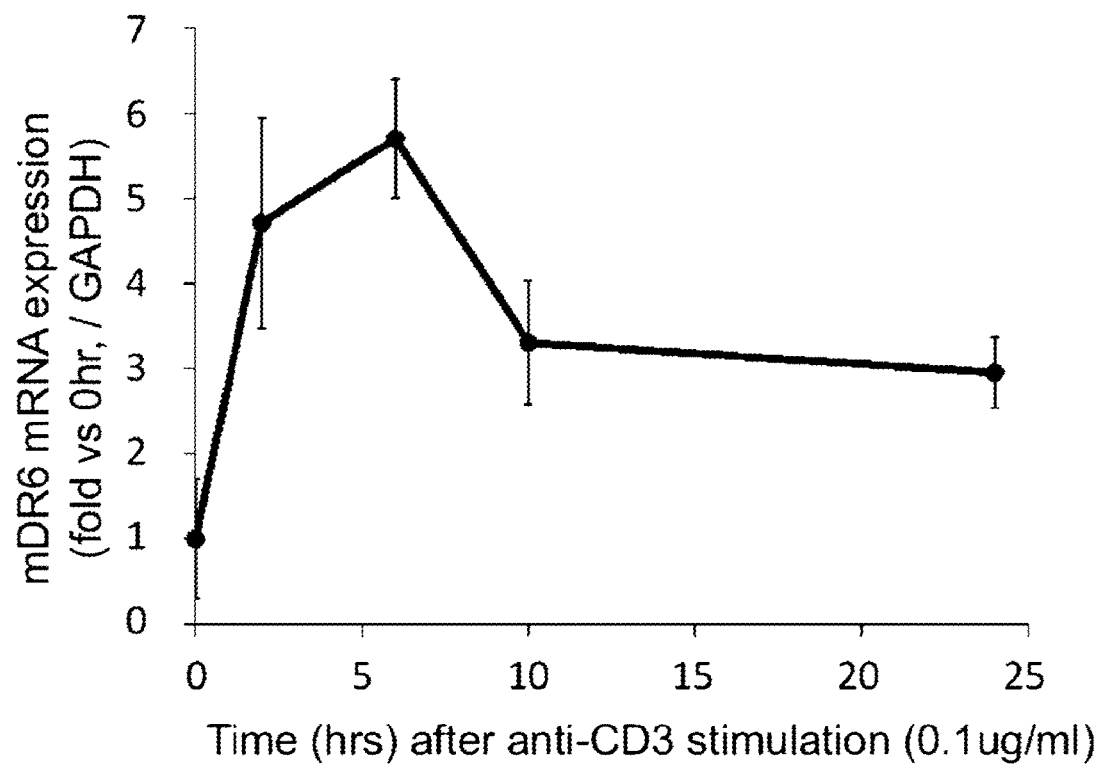
FIG. 6 is a graph showing the time course of the expression level of DR6 mRNA in T cells stimulated with anti-CD3 antibody.

(2) B cells isolated from mouse spleen were stimulated with LPS, and binding of the cells with labeled mDR6-hFcm was measured over time. Binding of labeled mDR6-hFcm to B cell increased at day 2 after LPS stimulation (FIG. 4). Also CD86, an activation marker of B cell that was measured simultaneously increased at day 2 after LPS stimulation (FIG. 5). These confirmed that expression of DR6 ligand is induced in the activation period of B cell. Meanwhile, T cells expressing DR6 on the cell membrane were stimulated with an anti-CD3 antibody, and an expression level of DR6-mRNA in the cell was measured over time, and it was confirmed that expression of DR6 as well was induced by stimulation with an anti-CD3 antibody, namely by stimulation of T cell activation (FIG. 6).

Figure 7:
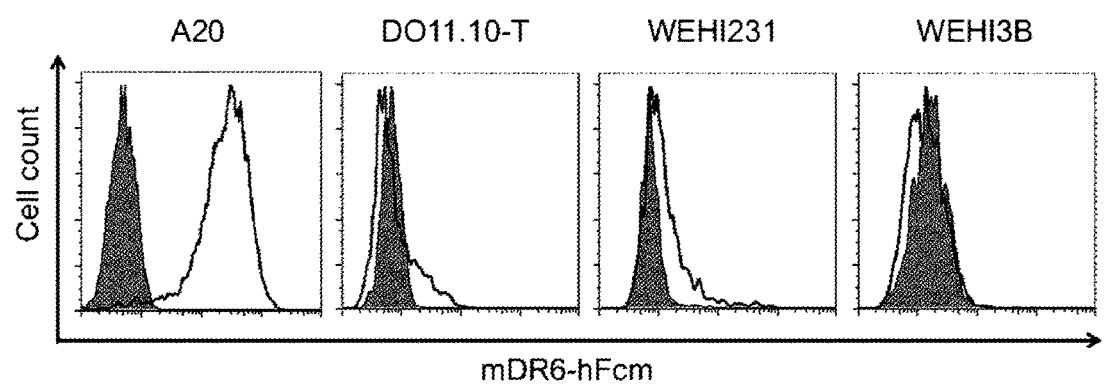
FIG. 7 includes charts showing the binding ability of A20 cells, DO11.10-T cells, WEHI231 cells and WEHI3B cells to mDR6-hFcm.
Figure 8:
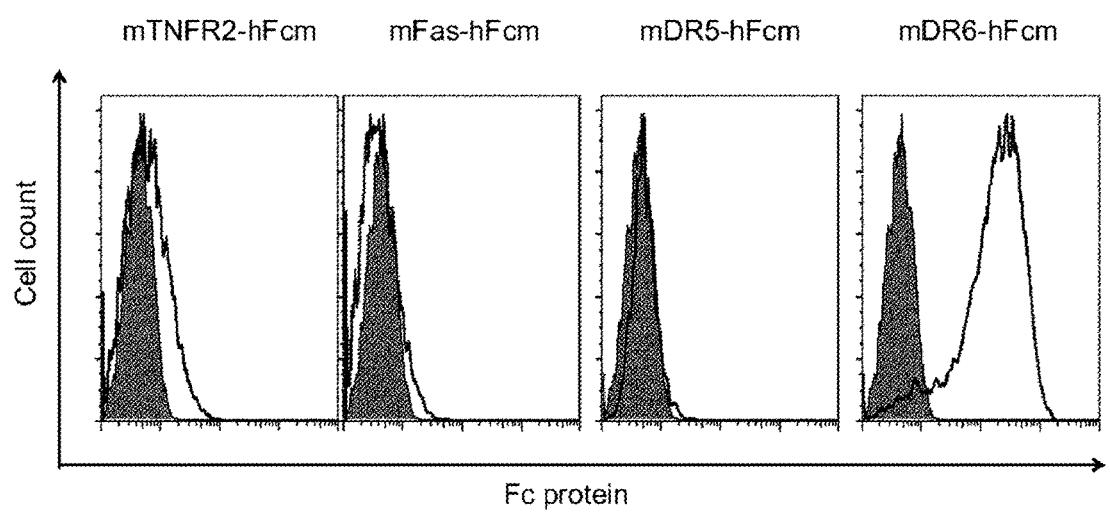
FIG. 8 includes charts showing the binding ability of A20 cells to mTNFR2-hFcm, mFas-hFcm, mDR5-hFcm and mDR6-hFcm.

(3) Binding abilities of immune cells (A20 cell, DO11.10-T cell, WEHI231 cell and WEHI3B cell) to labeled mDR6-hFcm were examined, and only A20 derived from matured B cell showed the binding ability to the labeled mDR6-hFcm (FIG. 7). Further, mDR6 (amino acids at positions 1-350) of labeled mDR6-hFcm was replaced by mouse TNF receptor (mTNFR2), mouse Fas protein (mFas), and mouse death receptor 5 (mDR5) to prepare labeled mTNFR2-hFcm, labeled mFas-hFcm and labeled mDR5-hFcm, respectively, and a binding ability of A20 cell thereto was examined. A20 cells specifically bound to labeled mDR6-hFcm (FIG. 8). That is, it was confirmed that the DR6 ligand that was present on A20 cell specifically bound to DR6.

(4) An expression vector into which a gene encoding mSdc1 (SEQ ID NO: 7) is incorporated in an expressible manner (pMXsIG/mSdc1), an expression vector into which a gene encoding hSdc1 (SEQ ID NO: 5) is incorporated in an expressible manner (pMXsIG/hSdc1) and a control vector (pMXsIG) were respectively introduced into DO11.10-T cells to prepare transformed cells. Also mDR6 (amino acids at positions 1-350) of labeled mDR6-hFcm was substituted with an extracellular region of hDR6 (amino acids at positions 1-350, SEQ ID NO: 86) to prepare labeled hDR6-hFcm.

Figure 9:
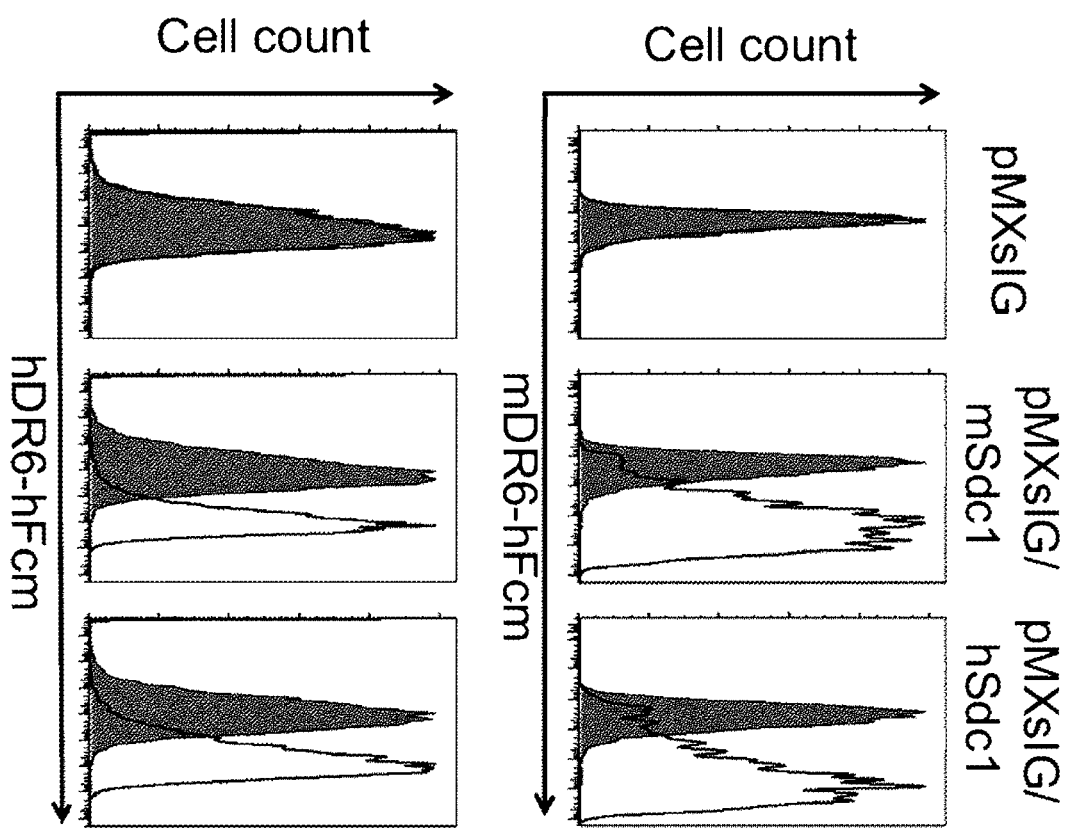
FIG. 9 includes charts showing the binding ability of DO11.10-T transformed cells expressing mSdc1 or hSdc1 to mDR6-hFcm and hDR6-hFcm.

Binding abilities of the aforementioned three kinds of transformed cells to labeled mDR6-hFcm and labeled hDR6-hFcm was examined, and all of the transformed cells except for the control bound to both labeled mDR6-hFcm and labeled hDR6-hFcm (FIG. 9). In other words, it was confirmed that mDR6 bound to mSdc1 and hSdc1, and hDR6 bound to mSdc1 and hSdc1.

Figure 10:
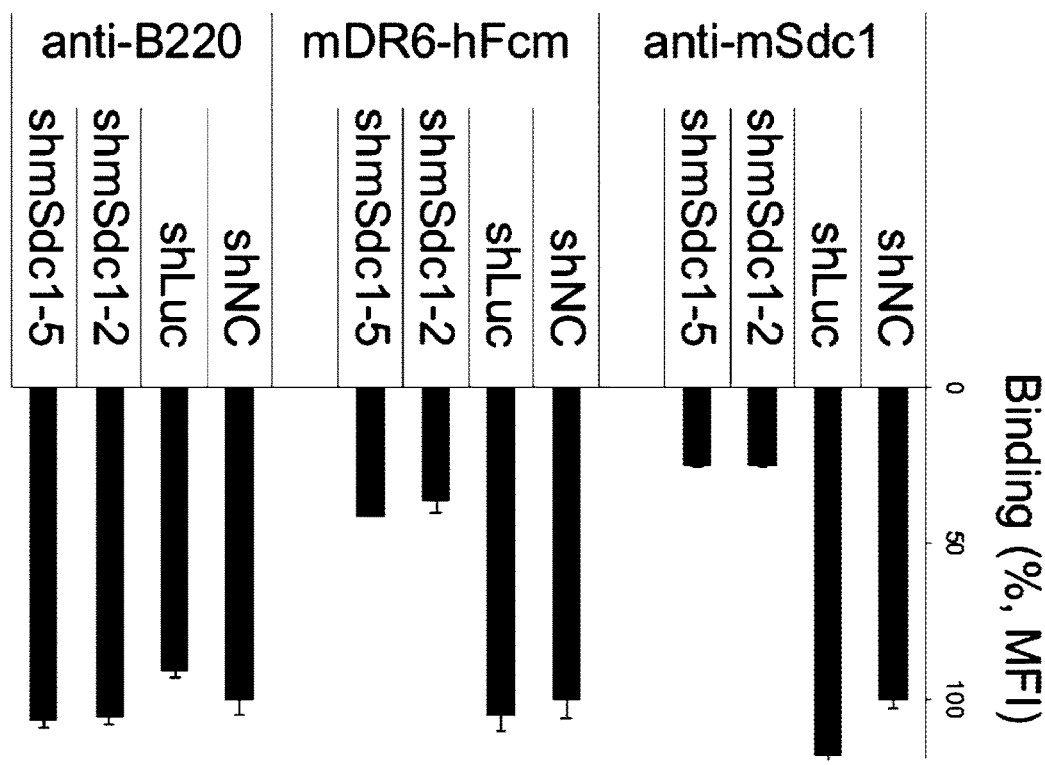
FIG. 10 is a graph showing the binding ability of A20 cells into which mSdc1-specific shRNA is introduced, to anti-mSdc1 antibody, mDR6-hFcm and anti-B220 antibody.

(5) Two kinds of specific shRNAs (shmSdc1-2 and shmSdc1-5) targeting different regions of the gene encoding mSdc1 were introduced into A20 cells to prepare transformed cells in which the expression of mSdc1 was suppressed. Binding abilities of the transformed cells to a commercially available anti-mSdc1 antibody, labeled mDR6-hFcm and an anti-B220 antibody were examined. The binding ability to labeled mDR6-hFcm decreased to the same extent as the anti-Sdc1 antibody (FIG. 10). That is, positive correlation between the expression of Sdc1 in A20 cell and the binding ability to labeled mDR6-hFcm was confirmed.

Figure 11:
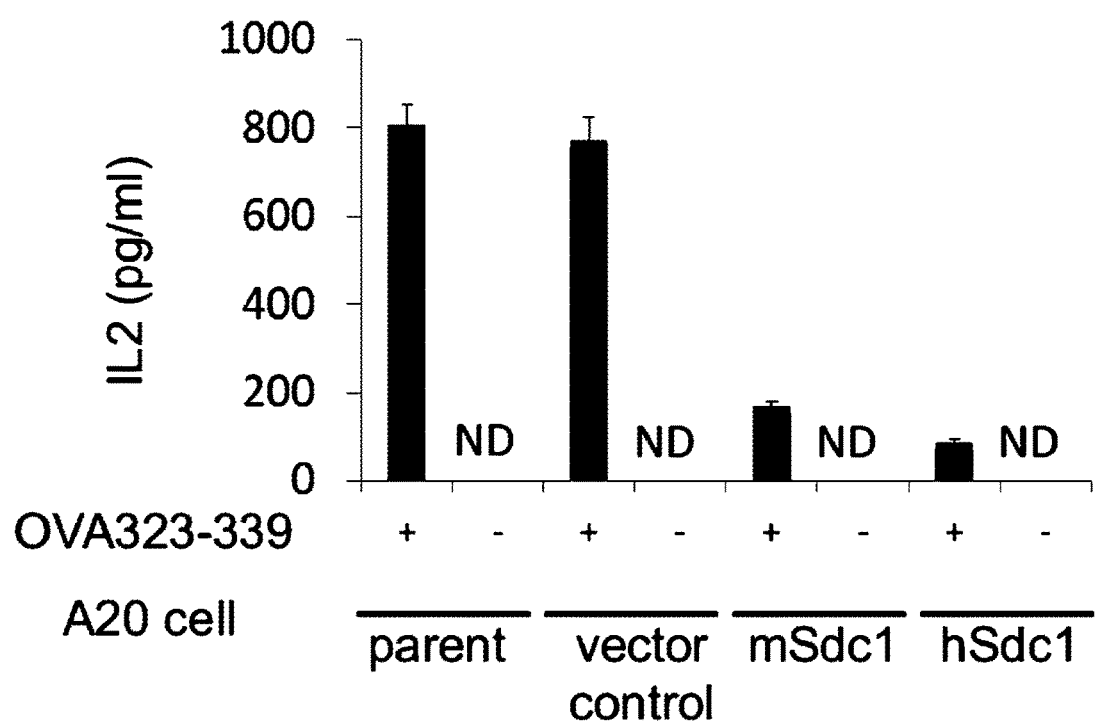
FIG. 11 is a graph showing the decrease in IL-2 production level produced by DO11.10-T cells co-cultured with mSdc1- or hSdc1-expressing A20 cells in a 10% fetal bovine serum (FCS)-containing RPMI1640 culture medium containing antigen OVA323-339.

(6) An expression vector into which a gene encoding mouse Sdc1 (mSdc1) was incorporated in an expressible manner (pMXsIG/mSdc1), an expression vector into which a gene encoding hSdc1 was incorporated in an expressible manner (pMXsIG/hSdc1) and a control vector (pMXsIG) were respectively introduced into A20 cells as antigen presenting cells showing reactivity with antigen OVA323-339 to prepare three kinds of transformed cells. After co-culturing the transformed cells and DO11.10-T cells in a 10% FCS-containing RPMI1640 culture medium containing antigen OVA323-339, the IL2 production level in each culture medium was measured by ELISA. In comparison with control transformed cells and untransformed A20 cells, the IL2 production level in the culture medium in which transformed A20 cells expressing mSdc1 or hSdc1 and DO11.10-T cells are cocultured decreased to less than or equal to 170 pg/ml (FIG. 11). That is, it was confirmed that the expression of hSdc1 or mSdc1 in antigen presenting cells suppressed T cell activation.

Figure 12:
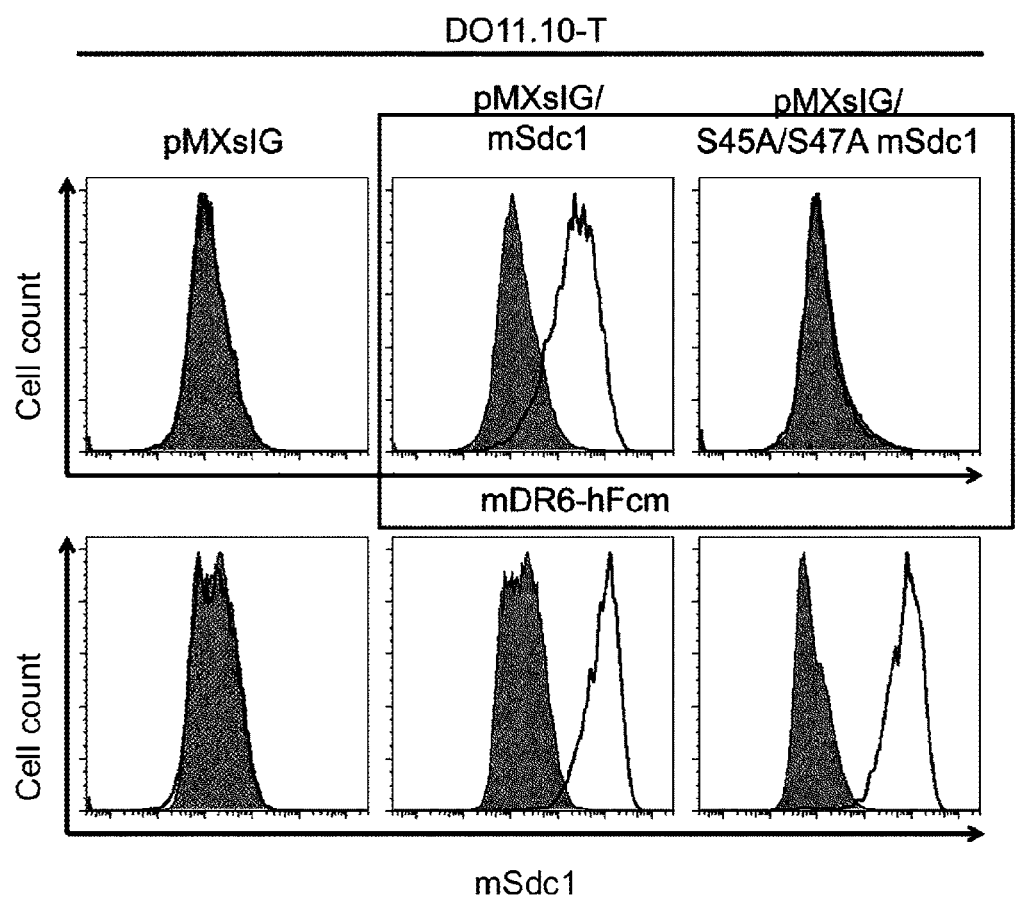
FIG. 12 includes charts showing the binding ability to mDR6-hFcm of transformed cells expressing a mSdc1 mutant in which serine at both of position and position 47 of mSdc1 is substituted with alanine.

(7) An expression vector into which a gene encoding mSdc1 mutant in which serine at both of position 45 and position 47 in mSdc1 was substituted with alanine was incorporated in an expressible manner (pMXsIG/S45A/S47AmSdc1) and the aforementioned pMXsIG/mSdc1 were respectively introduced into A20 cells to prepare transformed cells expressing mSdc1 mutant and transformed cells expressing mSdc1. Binding abilities of these two kinds of transformed cells to labeled mDR6-hFcm were examined. The binding ability of the cell expressing mSdc1 mutant was hardly detected in comparison with the transformed cell expressing mSdc1 (control) (FIG. 12).

The results of study shown in (1) to (7) reveal that Sdc1 is expressed on the cell membrane of B cells, and has a function of suppressing T cell activation, namely suppressing IL2 production by T cells, by binding to DR6 expressed on the cell membrane of T cells. This means that Sdc1 can be used as an immune regulating agent having an ability to bind specifically to DR6, and having an inductive ability of signal transduction leading to suppression of T cell activation. Therefore, one preferred embodiment of the present invention relates to an immune regulating agent or a T cell activation suppressing agent containing Sdc1 consisting of the amino acid sequence represented by SEQ ID NO: 6 or 8 as an active component.

The various experiments conducted in the above study were carried out by the techniques that are known or well known to those skilled in the art, for example, by the techniques described in textbooks or handbooks of the present field such as "Molecular Cloning: A Laboratory Manual 2nd. edition" (1989, Cold Spring Harbor Laboratory Press, Cold Spring Harbor, N.Y.) by Sambrook et al. and widely used by those skilled in the art. The procedure with use of a commercially available kit orreagentfollowedtheprotocoland/ortheparameterindicatedbythemanufacturer of the kit or the reagent unless otherwise specified.

Sdc1 which is one of the immune regulating agents of the present invention can beproducedasarecombinantproteinbyapplyingcommongenerecombinanttechniques to a nucleic acid represented by SEQ ID NO: 5 or SEQ ID NO: 7, which encodes the amino acid sequence.

In the present invention, for imparting an appropriate sugar chain at position and position 47 in the amino acid sequence represented by SEQ ID NO: 6 or SEQ ID NO: 8, it is preferred to use mammalian cells such as HEK293T cells derived from human fetal nephrocyte as host cells. Common gene recombinant techniques, comprising expression of a foreign protein in mammalian cells, include various methods described in textbooks or handbooks of the present field such as the aforementioned Sambrook et al. and widely used by those skilled in the art.

1-b) Agonist Sdc1 Mutant

Another embodiment of the present invention is an immune regulating agent which is a polypeptide consisting of an amino acid sequence in which one or more amino acids except for amino acids at position 45 and position 47 in the amino acid sequence represented by SEQ ID NO: 6 or SEQ ID NO: 8 are deleted and/or substituted, and/or an amino acid sequence in which one or more amino acids are added to the amino acid sequence represented by SEQ ID NO: 6 or SEQ ID NO: 8, and having an ability to bind specifically to DR6 and an activity of inducing signal transduction induced by specific binding between DR6 and Sdc1 (hereinafter, referred to as a Sdc1 mutant).

Generally, it is widely known to those skilled in the art that in a functional protein consisting of a certain amino acid sequence, deletion, substitution and/or addition of amino acids within a certain range are allowed while the function is kept. For example, regarding amino acid residues that are different between the amino acid sequence of hSdc1 and an amino acid sequence of Sdc1 derived from a different organism, e.g., mSdc1, which are confirmed by alignment of these amino acid sequences, and amino acid residues that are different among a syndecan family which are confirmed by alignment of the amino acid sequences of the family, they can sometimes be exchanged without loss of the functionality of the original protein.

Also regarding an amino acid gap confirmed by alignment of amino acid sequences, in which a corresponding amino acid is absent, the amino acid corresponding to the gap can sometimes be deleted or added without loss of the functionality of the original protein. Additionally, it is widely known that by substitution between amino acids, for example, between Leu (herein, natural amino acid is indicated by three letter code) and Ile, between Asp and Glu, between Asn and Gln, between Lys and Agr, between Ser and Thr or the like that are known to those skilled in the art as conservative substitution, the functionality of the original protein is sometimes not lost. In the current state of art, it is possible to predict with high accuracy the selection of the substitution position and the amino acid to be substituted capable of maintaining the function from the secondary structure prediction and/or three-dimensional structure prediction of the protein, and hydrophobicity, hydrophilicity, electric charge, bulkiness of side chains and other physical and chemical properties of amino acid.

Therefore, in one embodiment of the present invention Sdc1, a polypeptide consisting of an amino acid sequence in which one or more amino acids are deleted, substituted and/or added in the amino acid sequence represented by SEQ ID NO: 6 or SEQ ID NO: 8, and having an ability to bind to DR6 and an activity of inducing signal transduction leading to suppression of T cell activation can be used as a Sdc1 agonist mutant for DR6, and constitutes the immune regulating agent of the present invention.

A polypeptide consisting of an amino acid sequence in which amino acid residues at position 45 and position 47 in SEQ ID NO: 6 or SEQ ID NO: 8 are substituted with other amino acid residues cannot undergo glycosylation by heparan sulfate, and thus the polypeptide cannot exhibit the function as an agonist for DR6. A polypeptide consisting of an amino acid sequence in which amino acid residues at position 45 and position 47 are substituted or deleted in the amino acid sequence represented by SEQ ID NO: 6 or SEQ ID NO: 8 is not included in the present invention.

Also, the amino acid sequence at positions 1-17 in SEQ ID NO: 6 or SEQ ID NO: 8 is a so-called signal sequence that is useful when Sdc1 is secreted or placed on the membrane in the cell that biosynthesizes Sdc1. Such a signal sequence is not necessary for the ligand function for DR6. Therefore, a polypeptide consisting of an amino acid sequence in which amino acids at positions 1-17 in the amino acid sequence represented by SEQ ID NO: 6 or SEQ ID NO: 8 are deleted can also be used as a Sdc1 agonist mutant for DR6, and constitutes the immune regulating agent of the present invention.

The Sdc1 mutant which is one of the immune regulating agents of the present invention can be produced as a recombinant protein by applying common gene recombinant techniques including a method of introducing desired mutation to a nucleic acid represented by SEQ ID NO: 5 or SEQ ID NO: 7, which encodes the amino acid sequence.

In the present invention, for imparting an appropriate sugar chain at position and position 47 in the amino acid sequence represented by SEQ ID NO: 6 or SEQ ID NO: 8, it is preferred to use mammalian cells such as HEK293T cells as expression host cells. Common gene recombinant techniques, comprising expression of a foreign protein in such mammalian cells and a method of introducing desired mutation, include methodologies described in textbooks or handbooks of the present field such as the aforementioned Sambrook et al. and widely used by those skilled in the art.

1-c) Agonist Solubilized Sdc1

A further embodiment of the present invention is an immune regulating agent which is a polypeptide consisting of the amino acid sequence represented by SEQ ID NO: 10 or SEQ ID NO: 12, and having an ability to bind specifically to DR6 and an activity of inducing signal transduction induced by specific binding between DR6 and Sdc1 (hereinafter, referred to as solubilized Sdc1).

Solubilized Sdc1 is a polypeptide corresponding to the entire extracellular domain of Sdc1 or a part thereof, and the amino acid sequence thereof corresponds to the amino acid sequence at positions 1-250 in the amino acid sequence represented by SEQ ID NO: 6 or the amino acid sequence at positions 1-251 in SEQ ID NO: 8. Since solubilized Sdc1 does not have a transmembrane region, it is not anchored to membrane, and can be present in a solubilized state in cytoplasm, blood and other liquid medium.

Solubilized Sdc1 which is one of the immune regulating agents of the present invention can be produced as a recombinant protein by applying common gene recombinant techniques to a nucleic acid represented by SEQ ID NO: 9 or SEQ ID NO: 11, which encodes the amino acid sequence. Solubilized Sdc1 may be produced by protease digestion of Sdc1 obtained by applying common gene recombinant techniques to a nucleic acid represented by SEQ ID NO: 5 or SEQ ID NO: 7, which encodes the amino acid sequence.

In the present invention, for imparting an appropriate sugar chain at position and position 47 in the amino acid sequence represented by SEQ ID NO: 10 or SEQ ID NO: 12, it is preferred to use mammalian cells such as HEK293T cells as host cells. Common gene recombinant techniques, comprising expression of a foreign protein in mammalian cells, and a method of introducing desired mutation, include methodologies described in textbooks or handbooks of the present field such as the aforementioned Sambrook et al. and widely used by those skilled in the art.

1-d) Agonist Solubilized Sdc1 Mutant

A still another embodiment of the present invention is an immune regulating agent which is a polypeptide consisting of an amino acid sequence in which one or more amino acids except for amino acids at position 45 and position 47 in the amino acid sequence represented by SEQ ID NO: 10 or SEQ ID NO: 12 are deleted and/or substituted, and/or an amino acid sequence in which one or more amino acids are added to the amino acid sequence represented by SEQ ID NO: 10 or SEQ ID NO: 12, and having an ability to bind specifically to DR6 and an activity of inducing signal transduction induced by specific binding between DR6 and Sdc1 (hereinafter, referred to as a solubilized Sdc1 mutant).

The present embodiment includes a solubilized Sdc1 mutant consisting of an amino acid sequence in which amino acid is substituted, deleted, or added in the amino acid sequence represented by SEQ ID NO: 10 or SEQ ID NO: 12 as is the aspect above described for the Sdc1 mutant. For example, a polypeptide consisting of an amino acid sequence in which amino acids at positions 1-17 in the amino acid sequence represented by SEQ ID NO: 10 or SEQ ID NO: 12 are deleted is also a polypeptide having an ability to bind to DR6 and an activity of inducing signal transduction leading to suppression of T cell activation, and constitutes the immune regulating agent of the present invention as a solubilized Sdc1 mutant.

The C terminal amino acid residue of SEQ ID NO: 10 corresponds to the amino acid residue at position 250 in SEQ ID NO: 6, and even if several to ten and several amino acids of the amino acid sequence at position 251 or later in SEQ ID NO: 6 are added to C terminus of the amino acid sequence represented by SEQ ID NO: 10, or even if several to ten and several amino acids are deleted from the C terminus of SEQ ID NO: 10, the polypeptide consisting of such an amino acid sequence can have an ability to bind specifically to DR6 and an activity of inducing signal transduction concerning immune regulation via DR6. The same applies to SEQ ID NO: 12. A polypeptide consisting of an amino acid sequence in which several to ten and several amino acids are added or deleted in C terminus of SEQ ID NO: 10 or SEQ ID NO: 12 also constitutes the immune regulating agent of the present invention as a solubilized Sdc1 mutant.

The solubilized hSdc1 mutant which is one of the immune regulating agents of the present invention can be produced as a recombinant protein by applying common gene recombinant techniques including a method of introducing desired mutation to a nucleic acid represented by SEQ ID NO: 9 or SEQ ID NO: 11, which encodes the amino acid sequence.

In the present invention, for imparting an appropriate sugar chain at position and position 47 in the amino acid sequence represented by SEQ ID NO: 10 or SEQ ID NO: 12, it is preferred to use mammalian cells such as HEK293T cells as host cells. Common gene recombinant techniques, comprising expression of a foreign protein in such mammalian cells, and a method of introducing desired mutation, include methodologies described in textbooks or handbooks of the present field such as the aforementioned Sambrook et al. and widely used by those skilled in the art.

1-e) Anti-DR6 Agonist Antibody Another exemplary embodiment of the DR6 agonist is an anti-DR6 agonist antibody that specifically binds to DR6, and can induce signal transduction induced by specific binding between DR6 and Sdc1. The anti-DR6 agonist antibody includes a monoclonal antibody, a chimera antibody, a humanized antibody and a human antibody.

In a specific embodiment of the present invention, the DR6 agonist immune regulating agent can contain an anti-DR6 agonist antibody which binds to DR6 extracellular domain or a fragment thereof.

The anti-DR6 antibody of the present invention can be obtained by a common antibody preparation method known to those skilled in the art. Specifically, by immunizing a nonhuman mammal such as rat, rabbit, or human antibody producing transgenic mouse, with DR6, preferably DR6 produced by gene recombinant techniques or a part thereof, or a conjugate of the same with an appropriate carrier substance (for example, keyhole limpet hemocyanin, serum albumin, bovine thyroglobulin and soybean trypsin inhibitor etc.), together with an immunostimulant (Freund's complete or incomplete adjuvant etc.) as required, it is possible to induce a population of anti-DR6 antibody producing cells and to prepare the anti-DR6 antibody. Alternatively, the anti-DR6 antibody may be prepared by introducing a gene encoding DR6 to an appropriate expression vector, and causing DR6 to be expressed in a nonhuman mammal to thereby immunize the same to induce a population of anti-DR6 antibody producing cells.

The anti-DR6 antibody of the present invention is preferably a monoclonal antibody. Monoclonal antibodies can be acquired by culturing hybridomas obtained by fusing an anti-DR6 antibody producing cell and an immortalized cell lacking the autoantibody producing ability, for example, a myeloma cell, and selecting clones that produces monoclonal antibodies showing a specific affinity with the antigen used for immunization by immune precipitation or in vitro binding assay such as radioimmunoassay (RIA) or enzyme linked immunoassay (ELISA). As the steps constituting the monoclonal antibody preparation method, steps that are well known to those skilled in the art can be employed except for the step of preparing antigens and the step of selecting desired antibodies including assays of a physiological activity and a recognition specificity of the monoclonal antibody as will be described in later-described Examples.

Generally, a heavy chain and a light chain of an antibody respectively has a variable region on the N-terminus side and constant regions (CH, CL) on the C-terminus side. In variable regions of the heavy chain and the light chain respectively, complementarity determining regions (CDRs) exist, and this part is responsible for the specificity of antigen recognition. The part other than CDR has a function of retaining the structure of CDR, and is called a framework region (FR).

In a heavy chain variable region, there are three complementarity determining regions: a first complementarity determining region (CDR1), a second complementarity determining region (CDR2) and a third complementarity determining region (CDR3). The three complementarity determining regions in the heavy chain variable regions are referred to as heavy chain complementarity determining regions. Similarly in a light chain variable region, there are three complementarity determining regions: a first complementarity determining region (CDR1), a second complementarity determining region (CDR2) and a third complementarity determining region (CDR3). The three complementarity determining regions in the light chain variable region are referred to as light chain complementarity determining regions.

The anti-DR6 agonist antibody of the present invention includes an anti-DR6 agonist antibody, preferably a monoclonal antibody, having CDR comprising a novel amino acid sequence.

A preferred embodiment of the anti-DR6 agonist antibody of the present invention includes an antibody produced by clone 25-1 (25-1 antibody) as described in the later-described examples. Clone 25-1 is domestically deposited with Patent Microorganisms Depositary in National Institute of Technology and Evaluation on Oct. 17, 2013 under the accession number NITE P-01729 (Identification reference: 25-1), and internationally deposited on Oct. 27, 2014 under the accession number NITE BP-01729 (Identification reference: 25-1).

The anti-DR6 antibody produced by clone 25-1 is an anti-DR6 monoclonal antibody comprising a heavy chain CDR1 consisting of the amino acid sequence represented by SEQ ID NO: 14, a heavy chain CDR2 consisting of the amino acid sequence represented by SEQ ID NO: 16, a heavy chain CDR3 consisting of the amino acid sequence represented by SEQ ID NO: 18, a light chain CDR1 consisting of the amino acid sequence represented by SEQ ID NO: 20, a light chain CDR2 of which the amino acid sequence is Trp-Ala-Ser, and a light chain CDR3 consisting of the amino acid sequence represented by SEQ ID NO: 22.

An another preferred embodiment of the anti-DR6 agonist antibody of the present invention includes an antibody produced by clone 177-1 (177-1 antibody) as described in the later-described examples. Clone 177-1 is domestically deposited with Patent Microorganisms Depositary in National Institute of Technology and Evaluation on Oct. 17, 2013 under the accession number NITE P-01730 (Identification reference: 177-1), and internationally deposited on Oct. 27, 2014 under the accession number NITE BP-01730 (Identification reference: 177-1).

The anti-DR6 antibody produced by clone 177-1 is an anti-DR6 monoclonal antibody comprising a heavy chain CDR1 consisting of the amino acid sequence represented by SEQ ID NO: 24, a heavy chain CDR2 consisting of the amino acid sequence represented by SEQ ID NO: 26, a heavy chain CDR3 consisting of the amino acid sequence represented by SEQ ID NO: 28, a light chain CDR1 consisting of the amino acid sequence represented by SEQ ID NO: 30, a light chain CDR2 of which the amino acid sequence is Tyr-Ala-Ser, and a light chain CDR3 consisting of the amino acid sequence represented by SEQ ID NO: 32.

An another preferred embodiment of the anti-DR6 agonist antibody of the present invention includes an antibody produced by clone 82-30 (82-30 antibody) as described in the later-described examples. Clone 82-30 is domestically deposited with Patent Microorganisms Depositary in National Institute of Technology and Evaluation on Oct. 17, 2013 under the accession number NITE P-01731 (Identification reference: 82-30), and internationally deposited on Oct. 27, 2014 under the accession number NITE BP-01731 (Identification reference: 82-30).

The anti-DR6 antibody produced by clone 82-30 is an anti-DR6 monoclonal antibody comprising a heavy chain CDR1 consisting of the amino acid sequence represented by SEQ ID NO: 34, a heavy chain CDR2 consisting of the amino acid sequence represented by SEQ ID NO: 36, a heavy chain CDR3 consisting of the amino acid sequence represented by SEQ ID NO: 38, a light chain CDR1 consisting of the amino acid sequence represented by SEQ ID NO: 40, a light chain CDR2 of which the amino acid sequence of Trp-Ala-Ser, and a light chain CDR3 consisting of the amino acid sequence represented by SEQ ID NO: 42.

An another preferred embodiment of the anti-DR6 agonist antibody of the present invention includes an antibody produced by clone 186-18 (186-18 antibody) as described in the later-described examples. Clone 186-18 is domestically deposited with Patent Microorganisms Depositary in National Institute of Technology and Evaluation on Oct. 17, 2013 under the accession number NITE P-01732 (Identification reference: 186-18), and internationally deposited on Oct. 27, 2014 under the accession number NITE BP-01732 (Identification reference: 186-18).

The anti-DR6 antibody produced by clone 186-18 is an anti-DR6 monoclonal antibody comprising a heavy chain CDR1 consisting of the amino acid sequence represented by SEQ ID NO: 44, a heavy chain CDR2 consisting of the amino acid sequence represented by SEQ ID NO: 46, a heavy chain CDR3 consisting of the amino acid sequence represented by SEQ ID NO: 48, a light chain CDR1 consisting of the amino acid sequence represented by SEQ ID NO: 50, a light chain CDR2 of which the amino acid sequence of Trp-Ala-Ser, and a light chain CDR3 consisting of the amino acid sequence represented by SEQ ID NO: 52.

An another preferred embodiment of the anti-DR6 agonist antibody of the present invention includes an antibody produced by clone 180-10 (180-10 antibody) as described in the later-described examples. Clone 180-10 is domestically deposited with Patent Microorganisms Depositary in National Institute of Technology and Evaluation on Oct. 17, 2013 under the accession number NITE P-01733 (Identification reference: 180-10), and internationally deposited on Oct. 27, 2014 under the accession number NITE BP-01733 (Identification reference: 180-10).

The anti-DR6 antibody produced by clone 180-10 is an anti-DR6 monoclonal antibody comprising a heavy chain CDR1 consisting of the amino acid sequence represented by SEQ ID NO: 54, a heavy chain CDR2 consisting of the amino acid sequence represented by SEQ ID NO: 56, a heavy chain CDR3 consisting of the amino acid sequence represented by SEQ ID NO: 58, a light chain CDR1 consisting of the amino acid sequence represented by SEQ ID NO: 60, a light chain CDR2 of which the amino acid sequence of Trp-Ala-Ser, and a light chain CDR3 consisting of the amino acid sequence represented by SEQ ID NO: 62.

In the above-mentioned anti-DR6 agonist antibodies which are respective specific embodiments, the amino acid sequence other than respective CDR is not particularly limited, and one or several amino acid residues may be added, deleted, substituted and/or inserted in FR as required. Also, a so-called CDR grafted antibody in which the amino acid sequence other than CDR is derived from an antibody other than the antibody of the present invention, in particular derived from an antibody of a different organism species is encompassed in the antibody of the present invention.

A preferred example of the CDR grafted antibody is a humanized antibody in which CDR sequence is derived from mouse, rat, rabbit or other nonhuman animals, and the amino acid sequence other than CDR is derived from humans, or is a human antibody. A method for producing such a humanized antibody or a human antibody is known to those skilled in the art, and for example, the methods of Jones et al. (Nature, 1986, Vol. 321, pp. 522-525), Riechmann et al. (Nature, 1988, Vol. 332, pp. 323-327), and Verhoeyen et al. (Science, 1988, Vol. 239, pp. 1534-1536) are known, and they may be applied to each clone of the anti-DR6 agonist antibodies described above.

The anti-DR6 agonist antibody of the present invention includes a functional fragment thereof. The functional fragment means a partial fragment of an antibody, having an ability to bind to an antigen, and having a reactivity with the antigen or a capability of recognizing the antigen. The functional fragments include Fab, Fab', F(ab')$_2$, scFv, diabody, dsFv and peptides comprising CDR.

The Fab included in the present invention can be prepared as an antibody fragment having an antigen binding activity with a molecular weight of about 50,000 in which approximately N terminus half of the heavy chain and the entire light chain are bound via a disulfide bond, among the fragments obtained by digesting an anti-DR6 agonist antibody with papain. Also, Fab can be produced by making a nucleic acid encoding Fab of the antibody, and expressing it in a prokaryote or eukaryote by using various host expression systems that are well known to those skilled in the art, followed by recovering.

The F(ab')$_2$ included in the present invention can be prepared as an antibody fragment having an antigen binding activity with a molecular weight of about 100,000 which is larger than those consisting of Fabs bound via a disulfide bond in the hinge region, among fragments obtained by digesting an anti-DR6 agonist antibody with pepsin. Also F(ab')$_2$ can be prepared by binding two molecules of Fab' as will be described below via a thioether bond or a disulfide bond.

The Fab' included in the present invention can be prepared as an antibody fragment having an antigen binding activity with a molecular weight of about 50,000 in which the disulfide bond in the hinge region of the F(ab')$_2$ is dissociated with a reducing agent such as dithiothreitol. Also Fab' can be produced by making a nucleic acid encoding Fab' of the antibody, and expressing it in a prokaryote or eukaryote by using various host expression systems that are well known to those skilled in the art, followed by recovering.

The scFv included in the present invention is an antibody fragment having an antigen binding activity with a structure in which one heavy chain variable region (hereinafter, indicated by VH) and one light chain variable region (hereinafter, indicated by VL) are linked via an appropriate peptide linker (hereinafter, indicated by L), as indicatable by VH-L-VL or VL-L-VH.

The scFv included in the present invention can be produced by constructing a nucleic acid encoding scFv having the above-described structure based on the nucleic acids encoding VH and VL of the anti-DR6 agonist antibody of the present invention, and expressing it in a prokaryote or eukaryote by using various host expression systems that are well known to those skilled in the art, followed by recovering.

The diabody included in the present invention is an antibody fragment in which scFv is dimerized, having a bivalent antigen binding activity. The bivalent antigen binding activity may be the same or different from each other. For the diabody, the detailed description can be found, for example, in European patent No. 404,097 and International Publication WO01993/11161 pamphlet.

The diabody included in the present invention can be produced by constructing a nucleic acid encoding a polypeptide in which VH and VL are linked via a peptide linker L of 8 or less residues in amino acid sequence length based on the nucleic acids encoding VH and VL of the anti-DR6 agonist antibody of the present invention, and expressing it in a prokaryote or eukaryote by using various host expression systems that are well known to those skilled in the art, followed by recovering.

The dsFv included in the present invention refers to the one in which cysteine-containing HV and cysteine-containing LV prepared by substituting each one amino acid residue in VH and VL of the anti-DR6 agonist antibody of the present invention with a cysteine residue, are bound via a disulfide bond between these cysteine residues. The amino acid residue to be substituted with a cysteine residue can be determined by selection based on the conformation prediction of the antibody according to the method of Reiter et al. (Protein Engineering, 7:697-704, 1994).

The dsFv included in the present invention can be produced by constructing a nucleic acid encoding a polypeptide in which an amino acid residue specified by the method of Reiter et al. is substituted with cysteine, based on the nucleic acids encoding VH and VL of the anti-DR6 agonist antibody of the present invention, and expressing it in a prokaryote or eukaryote by using various host expression systems that are well known to those skilled in the art, followed by recovering.

The anti-DR6 agonist antibody of the present invention and the functional fragment thereof can be made into a labeled antibody or a derivative by binding or conjugating a radioisotope such as iodine 125, a low molecular compound such as a nucleic acid probe or a fluorescent labeling substance, a high molecular agent such as polyethylene glycol, albumin, dextran, polyoxyethylene, styrene maleic acid copolymer, polyvinyl pyrrolidone, pyrane copolymer and hydroxypropylmethacrylamide or protein and so on chemically or by genetic engineering, all of which are included in the present invention. Regarding the chemicals that can be bound to the antibody or the functional fragment thereof and their bindings, a method well known to those skilled in the art (for example, the method described in "Koutai Kogaku Nyumon (Introduction to Antibody Engineering)", by Osamu Kanemitsu, CHIJIN SHOKAN, 1994) can be used.

The anti-DR6 agonist antibody of the present invention may be glycosylated by a known method. The method of glycosylating an antibody is described, for example, in Jefferis et al. (Immunol., 1997, Vol. 65, pp. 111-128) or Wright et al. (TibTECH, 1997, Vol. 15, pp. 26-32), and such a method can be employed for the antibody of the present invention or the functional fragment thereof.

By the method of glycosylation, it is possible to prepare an antibody in which glycosylation pattern of the monoclonal antibody of the present invention is modified, specifically an antibody in which one or more sugar chains in the original antibody are removed, or one or more sugar chains are newly added, or the composition of sugar chain is modified. The present invention also includes such a glycosylated antibody as long as it is an anti-DR6 agonist antibody.

Further, the present invention includes a polypeptide comprising one or more of amino acid sequences of respective CDRs of the aforementioned clones 25-1, 177-1, 82-30, 186-18 and 180-10, as an anti-DR6 agonist. The CDRs may be bound to each other directly or via an appropriate peptide linker. Such a polypeptide can be produced by constructing a nucleic acid encoding one or more of the amino acid sequences, and expressing it in a prokaryote or eukaryote by using various host expression systems that are well known to those skilled in the art, followed by recovering. The polypeptide comprising CDR of the present invention can be produced by chemical synthesis methods that are well known to those skilled in the art, such as the Fmoc method (fluorenylmethyloxycarbonyl method), or the tBoc method (t-butyloxycarbonyl method).

2. Antagonist Immune Regulating Agent

In one embodiment of the present invention, there is provided an immune regulating agent having an ability to bind specifically to DR6, and a suppressive ability of signal transduction induced by specific binding between DR6 and Sdc1. That is, the present embodiment relates to an immune regulating agent as a DR6 antagonist, capable of binding to DR6 and suppressing the signal transduction leading to suppression of T cell activation to thereby activate T cells.

2-a) Anti-DR6 Antagonist Antibody

An exemplary embodiment of the DR6 antagonist is an anti-DR6 antagonist antibody that specifically binds to DR6, and can suppress signal transduction leading to suppression of T cell activation. The anti-DR6 antagonist antibody includes a monoclonal antibody, a chimera antibody, a humanized antibody and a human antibody.

In a specific embodiment of the present invention, the DR6 antagonist immune regulating agent can contain an anti-DR6 antagonist antibody which binds to DR6 extracellular domain or a fragment thereof.

A preferred embodiment of the anti-DR6 antagonist antibody of the present invention includes an antibody produced by clone 46-15-23 (46-15-23 antibody) as described in the later-described examples. Clone 46-15-23 is domestically deposited with Patent Microorganisms Depositary in National Institute of Technology and Evaluation on Oct. 17, 2013 under the accession number NITE P-01734 (Identification reference: 46-15-23), and internationally deposited on Oct. 27, 2014 under the accession number NITE BP-01734 (Identification reference: 46-15-23).

The anti-DR6 antibody produced by clone 46-15-23 is an anti-DR6 monoclonal antibody comprising a heavy chain CDR1 consisting of the amino acid sequence represented by SEQ ID NO: 64, a heavy chain CDR2 consisting of the amino acid sequence represented by SEQ ID NO: 66, a heavy chain CDR3 consisting of the amino acid sequence represented by SEQ ID NO: 68, a light chain CDR1 consisting of the amino acid sequence represented by SEQ ID NO: 70, a light chain CDR2 of which the amino acid sequence is Arg-Val-Ser, and a light chain CDR3 consisting of the amino acid sequence represented by SEQ ID NO: 72.

An another preferred embodiment of the anti-DR6 antagonist antibody of the present invention includes an antibody produced by clone 100-11 (100-11 antibody) as described in the later-described examples. Clone 100-11 is domestically deposited with Patent Microorganisms Depositary in National Institute of Technology and Evaluation on Oct. 17, 2013 under the accession number NITE P-01735 (Identification reference: 100-11), and internationally deposited on Oct. 27, 2014 under the accession number NITE BP-01735 (Identification reference: 100-11).

The anti-DR6 antibody produced by clone 100-11 is an anti-DR6 monoclonal antibody comprising a heavy chain CDR1 consisting of the amino acid sequence represented by SEQ ID NO: 74, a heavy chain CDR2 consisting of the amino acid sequence represented by SEQ ID NO: 76, a heavy chain CDR3 consisting of the amino acid sequence represented by SEQ ID NO: 78, a light chain CDR1 consisting of the amino acid sequence represented by SEQ ID NO: 80, a light chain CDR2 of which the amino acid sequence of Trp-Ala-Ser, and a light chain CDR3 consisting of the amino acid sequence represented by SEQ ID NO: 82.

In the above-mentioned anti-DR6 antagonist antibodies which are respective specific embodiments, the amino acid sequence other than respective CDR is not particularly limited, and one or several amino acid residues may be added, deleted, substituted and/or inserted in FR as required. Also, a so-called CDR grafted antibody in which the amino acid sequence other than CDR is derived from an antibody other than the antibody of the present invention, in particular derived from an antibody of a different organism species is encompassed in the antibody of the present invention.

A preferred example of the CDR grafted antibody is a humanized antibody in which CDR sequence is derived from mouse, rat, rabbit or other nonhuman animals, and the amino acid sequence other than CDR is derived from humans, or is a human antibody. A method for producing such a humanized antibody or a human antibody is known to those skilled in the art, and for example, the methods of Jones et al. (Nature, 1986, Vol. 321, pp. 522-525), Riechmann et al. (Nature, 1988, Vol. 332, pp. 323-327), and Verhoeyen et al. (Science, 1988, Vol. 239, pp. 1534-1536) are known, and they may be applied to each clone of the anti-DR6 antagonist antibodies described above.

The anti-DR6 antagonist antibody of the present invention includes a functional fragment thereof. The functional fragment means a partial fragment of an antibody, having an ability to bind to an antigen, and having a reactivity with the antigen or a capability of recognizing the antigen. The functional fragments include Fab, Fab', F(ab')$_2$, scFv, diabody, dsFv and peptides comprising CDR.

The Fab included in the present invention can be prepared as an antibody fragment having an antigen binding activity with a molecular weight of about 50,000 in which approximately N terminus half of the heavy chain and the entire light chain are bound via a disulfide bond, among the fragments obtained by digesting an anti-DR6 antagonist antibody with papain. Also, Fab can be produced by making a nucleic acid encoding Fab of the antibody, and expressing it in a prokaryote or eukaryote by using various host expression systems that are well known to those skilled in the art, followed by recovering.

The F(ab')$_2$ included in the present invention can be prepared as an antibody fragment having an antigen binding activity with a molecular weight of about 100,000 which is larger than those consisting of Fabs bound via a disulfide bond in the hinge region, among fragments obtained by digesting an anti-DR6 antagonist antibody with pepsin. Also F(ab')$_2$ can be prepared by binding two molecules of Fab' as will be described below via a thioether bond or a disulfide bond.

The Fab' included in the present invention can be prepared as an antibody fragment having an antigen binding activity with a molecular weight of about 50,000 in which the disulfide bond in the hinge region of the F(ab')$_2$ is dissociated with a reducing agent such as dithiothreitol. Also Fab' can be produced by making a nucleic acid encoding Fab' of the antibody, and expressing it in a prokaryote or eukaryote by using various host expression systems that are well known to those skilled in the art, followed by recovering.

The scFv included in the present invention is an antibody fragment having an antigen binding activity with a structure in which one heavy chain variable region (hereinafter, indicated by VH) and one light chain variable region (hereinafter, indicated by VL) are linked via an appropriate peptide linker (hereinafter, indicated by L), as indicatable by VH-L-VL or VL-L-VH.

The scFv included in the present invention can be produced by constructing a nucleic acid encoding scFv having the above-described structure based on the nucleic acids encoding VH and VL of the anti-DR6 antagonist antibody of the present invention, and expressing it in a prokaryote or eukaryote by using various host expression systems that are well known to those skilled in the art, followed by recovering.

The diabody included in the present invention is an antibody fragment in which scFv is dimerized, having a bivalent antigen binding activity. The bivalent antigen binding activity may be the same or different from each other. For the diabody, the detailed description can be found, for example, in European patent No. 404,097 and International Publication WO01993/11161 pamphlet.

The diabody included in the present invention can be produced by constructing a nucleic acid encoding a polypeptide in which VH and VL are linked via a peptide linker L of 8 or less residues in amino acid sequence length based on the nucleic acids encoding VH and VL of the anti-DR6 antagonist antibody of the present invention, and expressing it in a prokaryote or eukaryote by using various host expression systems that are well known to those skilled in the art, followed by recovering.

The dsFv included in the present invention refers to the one in which cysteine-containing HV and cysteine-containing LV prepared by substituting each one amino acid residue in VH and VL of the anti-DR6 antagonist antibody of the present invention with a cysteine residue, are bound via a disulfide bond between these cysteine residues. The amino acid residue to be substituted with a cysteine residue can be determined by selection based on the conformation prediction of the antibody according to the method of Reiter et al. (Protein Engineering, 7:697-704, 1994).

The dsFv included in the present invention can be produced by constructing a nucleic acid encoding a polypeptide in which an amino acid residue specified by the method of Reiter et al. is substituted with cysteine, based on the nucleic acids encoding VH and VL of the anti-DR6 antagonist antibody of the present invention, and expressing it in a prokaryote or eukaryote by using various host expression systems that are well known to those skilled in the art, followed by recovering.

The anti-DR6 antagonist antibody of the present invention and the functional fragment thereof can be made into a labeled antibody or a derivative by binding or conjugating a radioisotope such as iodine 125, a low molecular compound such as a nucleic acid probe or a fluorescent labeling substance, a high molecular agent such as polyethylene glycol, albumin, dextran, polyoxyethylene, styrene maleic acid copolymer, polyvinyl pyrrolidone, pyrane copolymer and hydroxypropylmethacrylamide or protein and so on chemically or by genetic engineering, all of which are included in the present invention. Regarding the chemicals that can be bound to the antibody or the functional fragment thereof and their bindings, a method well known to those skilled in the art (for example, the method described in "Introduction to Antibody Engineering", by Osamu Kanemitsu, CHIJIN SHOKAN, 1994) can be used.

The anti-DR6 antagonist antibody of the present invention may be glycosylated by a known method. The method of glycosylating an antibody is described, for example, in Jefferis et al. (Immunol., 1997, Vol. 65, pp. 111-128) or Wright et al. (TibTECH, 1997, Vol. 15, pp. 26-32), and for the antibody of the present invention or the functional fragment thereof, such a method can be employed.

By the method of glycosylation, it is possible to prepare an antibody in which glycosylation pattern of the monoclonal antibody of the present invention is modified, specifically an antibody in which one or more sugar chains in the original antibody are removed, or one or more sugar chains are newly added, or the composition of sugar chain is modified. The present invention also includes such a glycosylated antibody as long as it is an anti-DR6 antagonist antibody.

Further, the present invention includes a polypeptide comprising one or more of amino acid sequences of respective CDRs of the aforementioned clones 46-15-23 and 100-11, as an anti-DR6 antagonist. The CDRs may be bound to each other directly or via an appropriate peptide linker. Such a polypeptide can be produced by constructing a nucleic acid encoding one or more of the amino acid sequences of respective CDRs, and expressing it in a prokaryote or eukaryote by using various host expression systems that are well known to those skilled in the art, followed by recovering. The polypeptide comprising CDR of the present invention can be produced by chemical synthesis methods that are well known to those skilled in the art, such as the Fmoc method (fluorenylmethyloxycarbonyl method), or the tBoc method (t-butyloxycarbonyl method).

2-b) Antagonist Sdc1 Mutant

Another exemplary embodiment of the DR6 antagonist is a Sdc1 mutant that specifically binds to DR6, but is unable to induce signal transduction induced by specific binding between DR6 and Sdc1. Specifically, it is an immune regulating agent which is a polypeptide consisting of an amino acid sequence in which one or more amino acids except for amino acids at position 45 and position 47 in the amino acid sequence represented by SEQ ID NO: 6 or SEQ ID NO: 8 are deleted and/or substituted, and/or an amino acid sequence in which one or more amino acids are added to the amino acid sequence represented by SEQ ID NO: 6 or SEQ ID NO: 8, and having an ability to bind to DR6 and being unable to induce signal transduction induced by specific binding between DR6 and Sdc1 (hereinafter, referred to as a Sdc1 inactivation mutant).

2-c) Solubilized Sdc1 Mutant as Antagonist

Another exemplary embodiment of the DR6 antagonist is a solubilized Sdc1 mutant that specifically binds to DR6, but is unable to induce signal transduction induced by specific binding between DR6 and Sdc1. Specifically, it is an immune regulating agent which is a polypeptide consisting of an amino acid sequence in which one or more amino acids except for amino acids at position 45 and position 47 in the amino acid sequence represented by SEQ ID NO: 10 or SEQ ID NO: 12 are deleted and/or substituted, and/or an amino acid sequence in which one or more amino acids are added to the amino acid sequence represented by SEQ ID NO: 10 or SEQ ID NO: 12, and having an ability to bind to DR6 and being unable to induce signal transduction induced by specific binding between DR6 and Sdc1 (hereinafter, referred to as a solubilized Sdc1 inactivation mutant).

3. Immune Regulating Agent Having an Ability to Bind to Sdc1

In one embodiment of the present invention, provided is an immune regulating agent containing, as an active component, a physiologically active substance having an ability to bind to Sdc1 or a polypeptide consisting of an extracellular domain thereof, and a suppressive ability of signal transduction induced by specific binding between DR6 and Sdc1.

In a cell expressing DR6, when Sdc1 binds to DR6, signal transduction leading to suppression of T cell activation occurs. Therefore, a substance capable of preventing binding between Sdc1 and DR6 by binding to Sdc1 is expected to promote T cell activation by cancelling the suppression of T cell activation in the DR6 expressing cell.

Examples of the substance capable of preventing binding between Sdc1 and DR6 by binding to Sdc1 include anti-Sdc1 antibodies against Sdc1, particularly against the extracellular domain of Sdc1. The anti-Sdc1 antibodies are already commercially available, and any of these can be used as an immune regulating agent of the present invention. Also, an anti-Sdc1 antibody may be prepared newly according to a method that is well-known to those skilled in the art and may be used as the immune regulating agent of the present invention. Furthermore, various functional fragments corresponding to Fab, Fab', F(ab')$_2$, scFv, diabody, dsFv and peptides comprising CDR can be prepared from an anti-Sdc1 antibody, and these are also used as the immune regulating agent of the present invention.

Another example of the substance capable of preventing binding between Sdc1 and DR6 by binding to Sdc1 is a protein consisting of a soluble extracellular domain of DR6 and/or a mutant thereof. It is already known that solubilized DR6 consisting of an extracellular domain sequence of DR6 exists in nature. Since the solubilized-type DR6 lacks cytoplasmic death domain while retaining a binding ability to Sdc1, it is unable to cause a cell to initiate signal transduction leading to suppression of T cell activation. Such a naturally occurring solubilized-type DR6 is a substance that can prevent binding between Sdc1 and DR6 by binding to Sdc1, and can be used as the immune regulating agent of the present invention.

Such a naturally occurring solubilized DR6 can be prepared from a nucleic acid encoding DR6 by gene recombinant techniques, and in that case, the aforementioned mutation such as "conservative substitution" of amino acid, deletion or addition of amino acid gap, addition of an amino acid residue to the N-terminus and/or the C-terminus can be made without losing a binding ability to Sdc1. Such a mutant of solubilized DR6 can also be used as the immune regulating agent of the present invention.

The solubilized DR6 mutant can be produced as a recombinant protein by applying common gene recombinant techniques including a method of introducing desired mutation to a nucleic acid represented by SEQ ID NO: 1 or SEQ ID NO: 3, which encodes the amino acid sequence. Common gene recombinant techniques comprising expression of a foreign protein, and a method of introducing desired mutation include methodologies that are described in textbooks or handbooks of the present field such as the aforementioned Sambrook et al. and widely used by those skilled in the art.

In the later-described Example 10, it was revealed that a binding ability to Sdc1 increased with a deficiency of CRD1 among four CRDs present in the extracellular domain of DR6. Therefore the CRD1-deficient solubilized DR6 mutant is one preferred aspect of the immune regulating agent of the present invention.

4. Hybridoma

The present invention also includes hybridoma cell strain clone 25-1 deposited under the accession number NITE BP-01729, hybridoma cell strain clone 177-1 deposited under the accession number NITE BP-01730, hybridoma cell strain clone 82-30 deposited under the accession number NITE BP-01731, hybridoma cell strain clone 186-18 deposited under the accession number NITE BP-01732, hybridoma cell strain clone 180-10 deposited under the accession number NITE BP-01733, hybridoma cell strain clone 46-15-23 deposited under the accession number NITE BP-01734, hybridoma cell strain clone 100-11 deposited under the accession number NITE BP-01735, and hybridomas which provide antibodies capable of recognizing and binding the same epitopes as recognized and bound by monoclonal antibodies produced by these hybridoma cell strains.

5. Nucleic Acid

Another aspect of the present invention provides an isolated nucleic acid (DNA or RNA) encoding the aforementioned DR6 antagonist or DR6 agonist polypeptide, an expression vector comprising the nucleic acid, and a host cell comprising the nucleic acid or the vector. These nucleic acids may form "gene" by coupling a base sequence encoding the protein with any functional base sequences for modulating transcription and expression thereof, for example, a promotor sequence, an operator sequence, a ribosome binding site, a polyadenylation signal, and an enhancer.

Further, the present invention also includes a nucleic acid consisting of a base sequence capable of hybridizing with the aforementioned nucleic acid under stringent conditions. The stringent conditions of the hybridization reaction can be appropriately determined by those skilled in the art in consideration of conditions such as temperature and ion concentration, or can be such that hybridization is achieved by Southern hybridization including the general condition of washing the membrane in 6×SSC at 50° C., 5× Denhard's, 0.1% SDS, at 25° C. to 68° C. (1×SSC contains 0.15 M NaCl, and 0.015 M sodium citrate) after hybridization.

6. Screening Method

In one embodiment of the present invention, a method for screening an immune regulating agent having an ability to regulate signal transduction induced by specific binding between DR6 and Sdc1 is provided. Specifically, a method for screening a physiologically active substance having an ability to regulate signal transduction induced by binding between DR6 and Sdc1 comprising the following steps a) to e) is provided.

a) step of bringing DR6, a functional equivalent of DR6, or a protein comprising at least a functional extracellular domain of DR6, into co-presence with at least one of the polypeptides selected from the group consisting of Sdc and functional equivalents thereof, and a test substance, b) step of detecting signal transduction induced by specific binding between DR6, the functional equivalent of DR6 or the protein comprising at least a functional extracellular domain of DR6 and at least one of the polypeptides selected from the group consisting of Sdc and functional equivalents thereof in a), c) step of bringing DR6, a functional equivalent of DR6 or a protein comprising at least a functional extracellular domain of DR6 into co-presence with at least one of the polypeptides selected from the group consisting of Sdc and functional equivalents thereof in the absence of a test substance, d) step of detecting signal transduction induced by specific binding between DR6, the functional equivalent of DR6 or the protein comprising at least a functional extracellular domain of DR6 and at least one of the polypeptides selected from the group consisting of Sdc and functional equivalents thereof in c), and e) step of comparing a detection result in step b) and a detection result in step d).

The functional equivalent of DR6 in this context refers to a mutant retaining the function of DR6, an extracellular domain of DR6 having an ability to bind to Sdc1, a mutant retaining the function of the extracellular domain, or a polypeptide comprising them. The functional equivalent of Sdc1 refers to a substance having an ability to bind to DR6 and the function of inducing signal transduction induced by specific binding between DR6 and Sdc1, concretely refers to the Sdc1 mutant, the solubilized Sdc1 and the solubilized Sdc1 mutant having an agonistic effect on DR6.

DR6 and a functional equivalent thereof and Sdc1 and a functional equivalent thereof may be obtained by isolating and purifying a naturally occurring one, however, it ispreferredtousearecombinantproteinpreparedbyso-calledgeneticengineering techniques including gene cloning, gene amplification, incorporation into an expression vector, introduction of nucleic acid or an expression vector into a host cell, expression and purification of protein, and other operations. Specific examples include a recombinant protein that can be prepared by applying genetic engineering techniques to a nucleic acid consisting of the base sequence represented by SEQ ID NO: 1 or SEQ ID NO: 3 for DR6 and a functional equivalent thereof, and a recombinant protein that can be prepared by applying genetic engineering techniques to a nucleic acid consisting of the base sequence represented by SEQ ID NO: 5 or SEQ ID NO: 7 for Sdc1 and a functional equivalent thereof.

The genetic engineering techniques include techniques known or well known to those skilled in the art, for example, the techniques described in textbooks or handbooks of the present field such as "Molecular Cloning: A Laboratory Manual 2nd. edition" (1989, Cold Spring Harbor Laboratory Press, Cold Spring Harbor, N.Y.) by Sambrook et al. and widely used by those skilled in the art. With use of commercially available kits or reagents, it is preferred to follow the protocols and/or the parameters provided by the manufacturer of the kits or the reagents.

In preparation of DR6 and a functional equivalent thereof and Sdc1 and a functional equivalent thereof, particularly preferred expression vectors, host cells and purification methods include pcDNA3, HEK293T cell, Fc region of human IgG, and affinity column purification to an added tag such as a histidine tag.

The screening method of the present invention is preferably performed by using DR6 expressed on a natural T cell, or recombinant DR6 or a functional equivalent thereof expressed on a host cell that is transformed with a nucleic acid encoding DR6 or a functional equivalent thereof. In particular, it is preferably performed by using the aforementioned recombinant DR6 or a functional equivalent thereof with T cell as a host cell. By using such T cell, it is possible to monitor induction or suppression of signal transduction leading to suppression of T cell activation by IL2 production level in the T cell.

Also in the screening method of the present invention performed by using a natural T cell expressing DR6 or using recombinant DR6 or a functional equivalent thereof expressed on a host cell that is transformed with a nucleic acid encoding DR6 or a functional equivalent thereof, signal transduction in the present invention may be monitored by measuring changes in function, activity, form, chemical structure and the like of an intracellular molecule (including membrane protein) involved in signal transduction leading to suppression of T cell activation other than DR6. Such intracellular molecules include NFκB, NFAT, Fas, and FasL. All of these intracellular molecules are known molecules, and detection methods of the intracellular molecules such as immunoassay using respective specific antibodies or the like are known to those skilled in the art.

Further, signal transduction in the present invention may be monitored by using a host cell that is preliminarily modified so that expression of an appropriate reporter protein is induced or suppressed in response to signal transduction leading to suppression of T cell activation, and measuring behaviors of the reporter protein in place of the IL2 production level.

Further, signal transduction in the present invention may be monitored by using a chimera protein in which a transmembrane region and an intracellular death domain of DR6 is substituted with a transmembrane region and an intracellular domain of other transmembrane protein, and measuring signal transduction initiated by binding between DR6 and Sdc1 as a functional change in the intracellular domain of the chimera protein, or measuring changes in function, activity, form, chemical structure and the like of other intracellular molecule receiving a signal from the intracellular domain. Such a chimera protein is also encompassed in the DR6 mutant in the present invention.

One embodiment of the screening method of the present invention includes the step of bringing DR6 or a functional equivalent thereof and Sdc1 or a functional equivalent thereof into co-presence with a test substance under such a condition that signal transduction initiated by binding between DR6 or a functional equivalent thereof and Sdc1 or a functional equivalent thereof can be detected. A preferred example of the present embodiment is a screening method comprising the step of bringing DR6 expressed on a natural T cell, or recombinant DR6 or a functional equivalent thereof expressed on a host cell that is transformed with a nucleic acid encoding DR6 or a functional equivalent thereof, and Sdc1 or a functional equivalent thereof into co-presence with a test substance, and the step of detecting signal transduction in the natural T cell or the host cell.

By performing the screening method of the present embodiment, it is possible to select not only the substance that is directly involved in binding between DR6 or a functional equivalent thereof and Sdc1 or a functional equivalent thereof, but also the substance capable of regulating signal transduction by binding between DR6 or a functional equivalent thereof and Sdc1 or a functional equivalent thereof without direct involvement in the binding.

Another embodiment of the screening method of the present invention comprises the steps of: bringing DR6 or a functional equivalent thereof and Sdc1 or a functional equivalent thereof into co-presence with a test substance, selecting a test substance capable of inhibiting or suppressing binding between DR6 or a functional equivalent thereof and Sdc1 or a functional equivalent thereof, and then further detecting signal transduction initiated by binding between DR6 or a functional equivalent thereof and Sdc1 or a functional equivalent thereof for the selected test substance.

A preferred example of the present embodiment is a screening method comprising: a step of bringing a functional equivalent of DR6 and Sdc1 or a functional equivalent thereof, preferably solubilized Sdc1 or a solubilized Sdc1 mutant into co-presence with a test substance, a step of selecting a test substance capable of inhibiting or suppressing binding between a functional equivalent of DR6 and Sdc1 or a functional equivalent thereof, and a step of bringing DR6 expressed on a natural T cell, or recombinant DR6 or a functional equivalent thereof expressed on a host cell transformed with a nucleic acid encoding DR6 or a functional equivalent thereof, into co-presence with the selected test substance, to detect signal transduction in the natural T cell or the host cell. In particular, a method comprising a step of bringing solubilized DR6 and solubilized Sdc1 or a solubilized Sdc1 mutant, into co-presence with a test substance is preferred.

By performing the screening method of the present embodiment, it is possible to select a substance that is directly involved in binding between DR6 or a functional equivalent thereof and Sdc1 or a functional equivalent thereof more efficiently.

In the screening method of the present invention, binding between DR6 or a functional equivalent thereof and Sdc1 or a functional equivalent thereof, or binding between them and a test substance can be detected by ELISA, sandwich immune assay, Western blot assay, pull-down assay and other biochemical techniques. Also the binding may be detected by using IAsys analysis, BIAcore sensor chip analysis, microarray analysis, surface plasmon resonance (SPR) or the like. In that case, it is preferred that DR6 or a functional equivalent thereof or Sdc1 or a functional equivalent thereof is immobilized on an appropriate matrix and used. All of these techniques are widely known to those skilled in the art, and they can be applied to the present invention within the range of ordinary practicing ability of a person skilled in the art.

7. Treating Method

An embodiment of the present invention also provides a method for preventing or treating immune disease in a subject, and specifically comprises administering an effective amount of an immune regulating agent of the present invention to a mammal.

The "subject" used herein is a mammal, including, for example, human, bovine, equine, canine, and feline, and in particular, the subject of the present invention is human.

The "effective amount" used herein means the amount of the immune regulating agent effective for preventing, curing or remitting the disease or the symptom which is to be treated. The effective amount is appropriately adjusted depending on the kind of the disease, the severity of the symptom, the patient and other medical factors.

One embodiment of the treating method of the present invention relates to a method for preventing or treating disease caused by excessive or abnormal immune response in a mammal by administering an effective amount of the immune regulating agent capable of inducing signal transduction induced by specific binding between DR6 and Sdc1.

The diseases to be treated by the treating method of the present embodiment include autoimmune diseases such as rheumatism, systemic lupus erythematosus (SLE), multiple sclerosis, transplantation disease, Crohn disease, ulcerative colitis, and Sjögren syndrome, and allergic diseases such as pollinosis, atopy, and serious drug eruption.

Another embodiment of the treating method of the present invention relates to a method for preventing or treating disease for which enhancement of immune function in a mammal is desired by administering an effective amount of the immune regulating agent capable of suppressing signal transduction induced by specific binding between DR6 and Sdc1.

The diseases to be treated by the treating method of the present embodiment include infectious diseases by bacteria, fungi or other foreign organisms, and malignant neoplasm. Use of the immune regulating agent of the present invention as a vaccine adjuvant is also encompassed in the present embodiment.

In the treating method of the present invention, the immune regulating agent is preferably administered in the form of a pharmaceutical composition or a preparation containing a pharmaceutically acceptable excipient, carrier and other components. The immune regulating agent in the form of the pharmaceutical composition or the preparation is also one aspect of the immune regulating agent of the present invention.

The pharmaceutically acceptable components are well known to those skilled in the art, and a person skilled in the art can appropriately select and use a component from components indicated in the 16th Edition of the Japanese Pharmacopoeia or other standards depending on the form of the preparation, within the range of the ordinary practicing ability. The immune regulating agent of the present invention may also be used together with other pharmaceuticals depending on the disease to be treated.

8. Diagnostic Method

The present invention provides a method for diagnosing a subject suffering from or suspected of a disease caused by excessive or abnormal immune response or a disease caused by deterioration in immune function, comprising a step of examining a sample for presence or content of DR6 and/or Sdc1 in a sample collected from a subject.

The disease to be diagnosed by the diagnostic method of the present invention include autoimmune disease such as rheumatism and systemic lupus erythematosus (SLE), and allergic diseases such as pollinosis, atopy, and serious drug eruption.

A preferred embodiment of the diagnostic method of the present invention relates to an immune assay for examining presence and/or content of the aforementioned DR6 and/or Sdc1 using the anti-DR antibody and/or anti-Sdc1 antibody disclosed herein. Also another embodiment of the diagnostic method of the present invention relates to a method for examining presence or content of DR6 and/or Sdc1 in a sample based on a nucleic acid encoding the same.

The immune assay can be carried out by various techniques well known in the art, and non-limiting examples of such techniques include immunohistological analysis, in situ hybridization, immunoblot analysis, Western blot analysis, and tissue array analysis of a sample and a cell strain. Also diagnosis based on nucleic acid can be carried out by various techniques well known in the art, and non-limiting examples of such techniques include various PCR analyses including RT-PCR, Northern blot analysis, and Southern blot analysis.

EXAMPLES

Hereinafter, the present invention will be described in more detail by way of non-limiting examples, however it is easily recognized by a person skilled in the art that the present invention is not limited to specific methodologies, protocols, cell strains, animal species or genus, constructs, and reagents described herein, and these can be appropriately changed.

The techniques and procedures described or referred herein including examples are conducted by using the techniques that are described, for example, in the Sambrook et al. or other textbooks or handbooks of the present field, and are widely used by those skilled in the art. The procedure accompanied with use of a commercially available kit or reagent was conducted according to the protocol and/or the parameter indicated by the manufacturer of the kit or the reagent unless otherwise specified. These textbooks and handbooks of the present field, and all documents referenced by the present specification are incorporated herein by reference.

Example 1

(1) Construction of Expression Vectors of mSdc1 and hSdc1

Using a cDNA library prepared by using mRNA extracted from A20 cells as a template, PCR amplification was carried out by using DNA primers designed so that DNA corresponding to the open reading frame (ORF) of mouse Sdc1 (mSdc1) represented by SEQ ID NO: 8 was amplified. The amplified DNA was recombined in an expression vector pMXsIG that was cleaved with restriction enzymes EcoRI and NotI to construct pMXsIG/mSdc1.

Similarly, using a cDNA library prepared by using mRNA extracted from HeLa cells derived from human cervical cancer as a template, PCR amplification was carried out by using DNA primers designed so that DNA corresponding to the open reading frame (ORF) of human Sdc1 (hSdc1) represented by SEQ ID NO: 6 was amplified. The amplified DNA was recombined in an expression vector pMXsIG that was cleaved with restriction enzymes BamHI and XhoI to construct pMXsIG/hSdc1.

(2) Transformation and Measurement of IL2 Production Level

The pMXsIG/mSdc1 or the pMXsIG/hSdc1 was introduced into Plat-E cells by the lipofection method using Lipofectamine 2000 (available from Invitrogen) to prepare a retrovirus. The obtained retrovirus and A20 cell as an antigen presenting cell showing reactivity with antigen OVA323-339 were mixed, and cultured in 10% FCS-containing RPMI1640 culture medium for 48 hours to prepare transformed A20 cells in which mSdc1 or hSdc1 is expressed on the cell. After co-culturing the transformed cells and DO11.10-T cells in 10% FCS-containing RPMI1640 culture medium containing antigen OVA 323-339 at 37° C. for 16 hours, the IL2 production level in each culture medium was measured by a ELISA kit (available from R&D Systems).

As shown in FIG. 11, the production level of IL2 in the culture medium in which A20 cells expressing mSdc1 or hSdc1 and DO11.10-T cells are cocultured decreased to less than or equal to 170 pg/mL in contrast to the control and untransformed A20 cells.

Example 2

(1) Preparation of Recombinant Sdc1

Using a cDNA vector pMXsIG/mSdc1 as a template in which the gene encoding mSdc1 represented by SEQ ID NO: 7 was cloned, PCR amplification was carried out by using DNA primers designed and synthesized so that DNA (SEQ ID NO: 11) encoding an extracellular domain of mSdc1 (amino acid sequence up to position 251 in SEQ ID NO: 8) was amplified.

The amplified DNA was incorporated in an expression vector pcDNA3.1/myc-his_ver. B (available from Invitrogen) that was cleaved with restriction enzymes EcoRI and BamHI in such a manner that the reading frame of the His sequence preliminarily incorporated in the expression vector and the reading frame of the incorporated mSdc1 extracellular domain match each other, and pcDNA3.1/mSdc1-his was constructed so that a protein consisting of an amino acid sequence to which His sequence was added at the C terminus (mSdc1-His, SEQ ID NO: 84) was amplified. This pcDNA3.1/mSdc1-his was introduced into HEK293T cells, and cultured for 7 days in a Freestyle 293 Expression culture medium (available from Invitrogen) to allow secretion of mSdc1-His in the culture medium, and mSdc1-His was purified by using a Ni-NTA affinity column.

(2) Effect of mSdc1 Stimulation on CD3-Dependent IL2 Production

Figure 13:
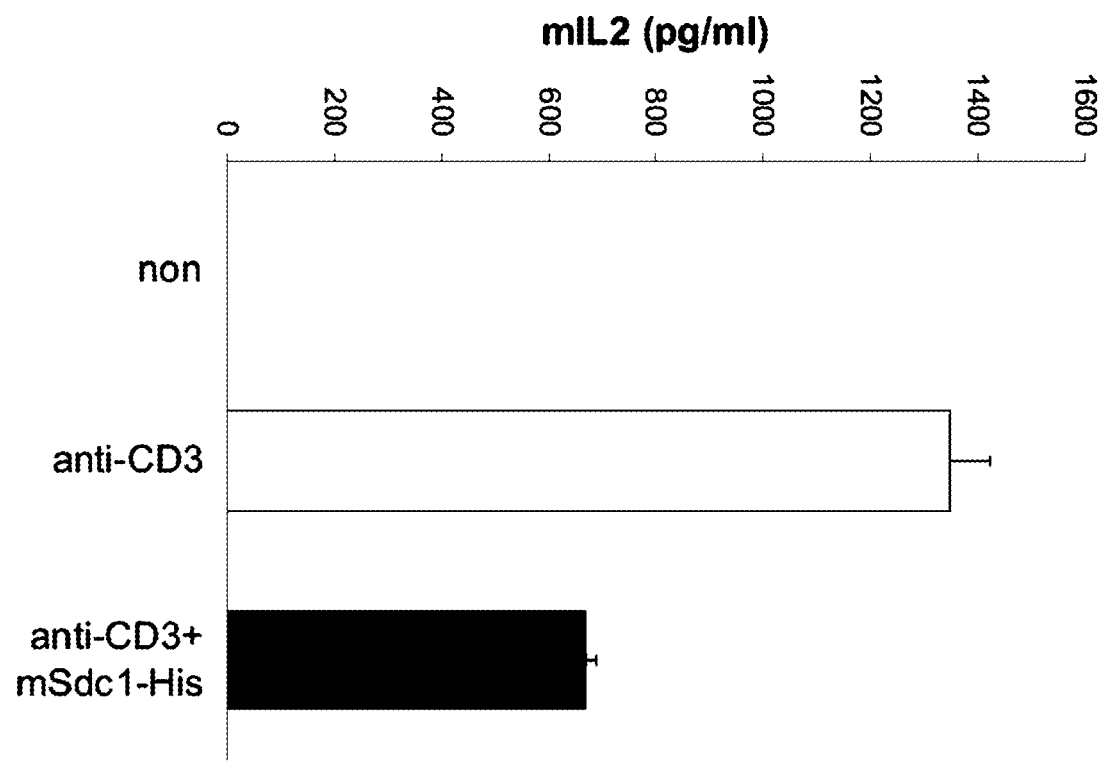
FIG. 13 is a graph showing the agonistic effect (suppression of IL2 production level of T cells) of mSdc1-His on DO11.10-T cells.

In a 96-well cell culturing plate in which anti-CD3 antibody was immobilized, 3×10$^4$ cells of DO11.10-T cell were cultured for 16 hours in a 10% FCS-containing RPMI 1640 culture medium containing mSdc1-His (final concentration 100 nM) prepared in (1). IL2 in the culture supernatant was quantified by an ELISA kit (available from R&D systems). The result is shown in FIG. 13.

It was observed that in comparison with the IL2 level produced by DO11.10-T cells to which only anti-CD3 antibody stimulation was given (anti-CD3 in the drawing), the IL2 production level of the hybridoma to which mSdc1-His was added decreased to about 50%. The "non" in the drawing is a negative control in which DO11.10-T cells were cultured in the absence of anti-CD3 antibody and mSdc1-His, the culture medium of which was measured for IL2.

(3) Effect of Suppression of DR6 Expression

Figure 14:
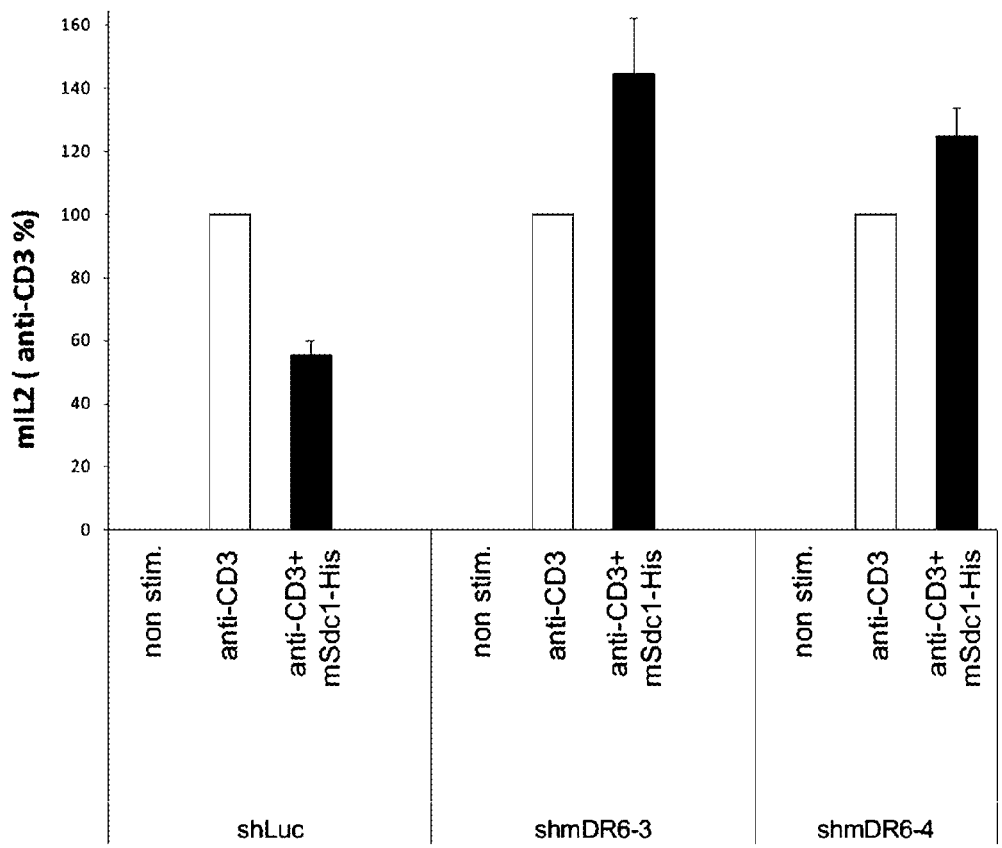
FIG. 14 is a graph indicating that the suppression of IL2 production by mSdc1-His is not observed in DO11.10-T cells into which mDR6-specific shRNA is introduced.

The experiment of the above (2) was carried out by using DO11.10-T cells into which two specific shRNAs (mDR6-3 and mDR6-4) targeting different regions in the gene encoding DR6 were introduced in place of DO11.10-T cells. As can be seen from the result shown in FIG. 14, suppression of IL2 production by mSdc1-His was not observed in DO11.10-T cells into which shRNA was introduced.

From the above, it was confirmed that mSdc1 had a function of suppressing IL2 production depending on the expression of DR6 for T cell expressing DR6.

Example 3 Change in Expression of Fas and FasL

Figure 15:
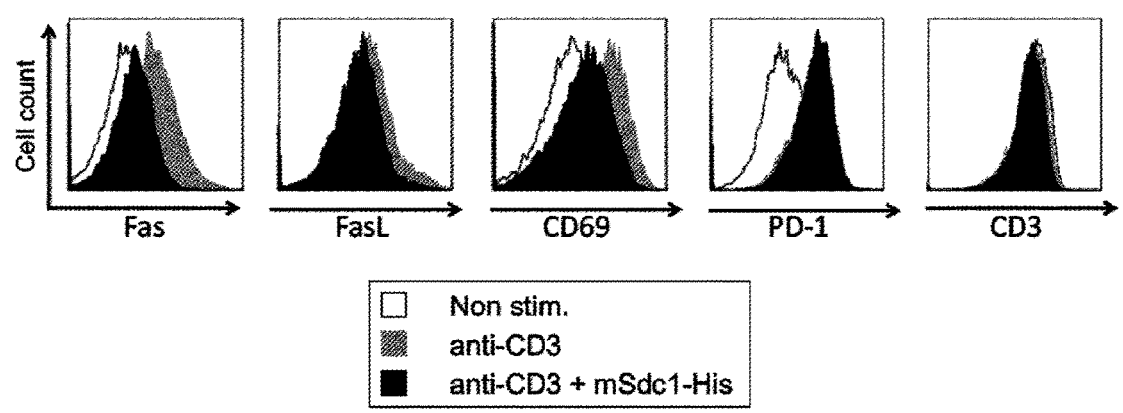
FIG. 15 includes charts showing the expression variation of each protein (Fas, FasL, CD69, PD-1 and CD3) in DO11.10-T cells stimulated with anti-CD3 antibody and mSdc1-His.

In DO11.10-T cells stimulated with anti-CD3 antibody and mSdc1-His in Example 2, the expression variation of each protein (Fas, Fas ligand (FasL), CD69, PD-1 and CD3) after a lapse of 6 hours from stimulation was analyzed by flow cytometry. The result is shown in FIG. 15. In the chart, the outline waveform indicates the control not stimulated with anti-CD3 antibody and mSdc1-His, the gray waveform indicates DO11.10-T cells stimulated only with anti-CD3 antibody, and the black waveform indicates DO11.10-T cells stimulated with anti-CD3 antibody and mSdc1-His.

As shown in FIG. 15, it was observed that expression of Fas and FasL induced depending on the stimulation with anti-CD3 antibody was suppressed by stimulation with mSdc1. It was revealed that signal transduction induced by specific binding between DR6 and Sdc1 could be monitored by the variation in expression level of Fas or FasL.

Example 4 Change in Behaviors of Transcription Factors

A DNA fragment encoding NFκB, CREB, or ISRE response sequence synthesized to have a XhoI restriction enzyme recognition sequence on 5'-terminal side and a HindIII restriction enzyme recognition sequence on 3'-terminal side was incorporated into pGL4.26 (available from Promega) harboring firefly luciferase gene, that was cleaved by a treatment with restriction enzymes XhoI and HindIII, to prepare NFκB, CREB and ISRE responsive reporter plasmid. For measuring NFAT activity, a commercially available reporter plasmid (pGL4.30 [luc2P/NFAT-RE/Hygro], available from Promega) harboring firefly luciferase gene incorporated downstream the NFAT response sequence was used.

Stimulation with anti-CD3 antibody or stimulation with anti-CD3 antibody and mSdc1-His was applied to DO11.10-T cells into which the aforementioned reporter plasmid was introduced, and the activity of each of the transcription factor proteins (NFAT, NFκB, CREB and ISRE) after a lapse of 6 hours from stimulation was monitored by change in the activity of a reporter protein luciferase. The result is shown in FIG. 16.

Figure 16:
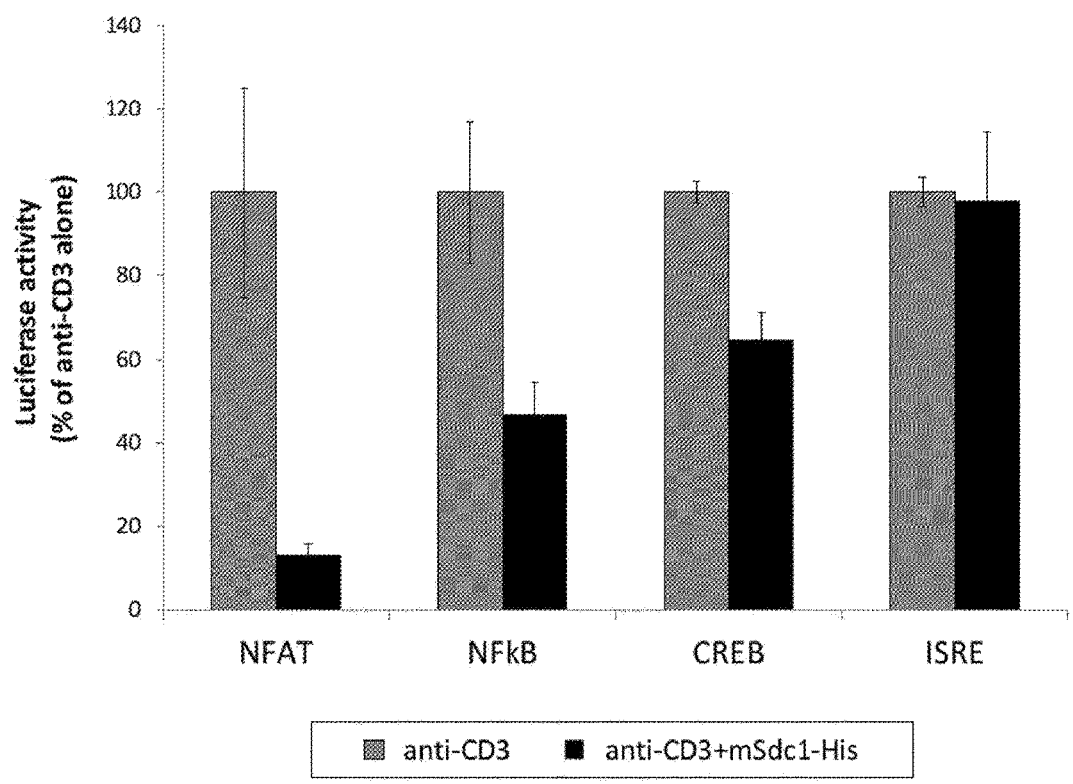
FIG. 16 is a graph showing the change in the activity of a reporter protein luciferase indicating the activity variation of each protein (NFAT, NFκB, CREB and ISRE) in DO11.10-T cells stimulated with anti-CD3 antibody and mSdc1-His.

As illustrated in FIG. 16, it was observed stimulation with mSdc1 strongly suppressed the activities of NFAT and NFκB. It was revealed that signal transduction induced by specific binding between DR6 and Sdc1 could be monitored by variation in the activity of NFAT or NFκB.

Example 5 Preparation of Monoclonal Antibody (1) Preparation of Hybridoma

After passing mDR6-hFcm, recombinant soluble mDR6, through a filter having a pore size of 0.45 mm (available from Millipore), the mDR6-hFcm was intraperitoneally injected three times (0.2 mg/time) to Wistar rats having injected with an adjuvant according to a routine method to immunize the rats. Then splenocytes were collected from the immunized rats, and fused with mouse myeloma cell strain P3U1 by using 50% polyethylene glycol 1500 (available from Roche) to prepare hybridomas. The hybridomas were cultured for about 10 days until colonies were observed in a RPMI1640 culture medium containing penicillin/streptomycin, 10% (w/v) fetal bovine serum (FCS) and a HAT solution according to a routine method.

By these operations, clone 25-1, clone 25-2, clone 25-3, clone 177-1, clone 82-30, clone 186-18, clone 180-10, clone 46-15-23 and clone 100-11 were obtained as hybridomas that produce anti-DR6 antibody. These hybridomas except for clone 25-2 and clone 25-3 were lyophilized according to a routine method, and deposited with Patent Microorganisms Depositary in National Institute of Technology and Evaluation.

(2) CDR Analysis

Using SMART cDNA library preparation kit (available from TAKARA BIO INC.), CDR sequences of the hybridomas selected in (1) were analyzed. Specifically, total RNA was extracted from each hybridoma, and cDNA was prepared by using the total RNA as a template, and using a 3'-terminal side IgG1 heavy chain specific primer, an IgG2a heavy chain specific primer or a K light chain specific primer. Using the cDNA as a template, PCR amplification was carried out by using a 5'-terminal side specific primer accompanying the kit as a forward primer, and the 3'-terminal side IgG1 heavy chain specific primer, the IgG2a heavy chain specific primer or the K light chain specific primer as a reverse primer. The nucleic acid sequence of the amplified DNA fragment was analyzed by a DNA sequencer, and the obtained sequence information was searched on the IgBLAST database. As a result, it was confirmed that all monoclonal antibodies produced by the hybridomas prepared in (1) had a new combination of CDR sequences. Amino acid sequences of heavy chains CDR1 to 3 of each of clones 25-1, 177-1, 82-30, 186-18, 180-10, 46-15-23 and 100-11 are shown in Table 1, and amino acid sequences of light chains CDR1 to 3 are shown in Table 2.

TABLE 1

| Heavy chain | CDR1 | CDR2 | CDR3 |
|---|---|---|---|
| 25-1 | Gly Phe Thr Phe Ser Tyr Tyr (SEQ ID NO: 14) | Asn Ile Ser Asn Gly Gly Asn Thr (SEQ ID NO: 16) | Gly Ala Arg Gln Asp Tyr Pro Ala Ile Thr Gly Val Met Glu Ala (SEQ ID NO: 18) |
| 177-1 | Gly Phe Thr Phe Asn Tyr Trp (SEQ ID NO: 24) | Asn Ile Thr Asn Thr Gly Ser Ile (SEQ ID NO: 26) | Gly Thr Arg Asp Ser Asp Tyr Gly Gly Tyr Gly Trp Phe Ala Tyr (SEQ ID NO: 28) |
| 82-30 | Gly Phe Thr Phe Ser Tyr Gly (SEQ ID NO: 34) | Asn Ile Ser Thr Ser Thr Ser Thr (SEQ ID NO: 36) | Gly Thr Asn Tyr Tyr Asp Gly Ser Tyr Phe Asp Tyr (SEQ ID NO: 38) |
| 186-18 | Gly Phe Thr Phe Ser Tyr Gly (SEQ ID NO: 44) | Asp Ile Ser Tyr Asp Gly Arg Thr (SEQ ID NO: 46) | Ser Ala Arg His Gly Asn Tyr Phe Asp Gly Tyr Tyr Asp Tyr (SEQ ID NO: 48) |
| 180-10 | Gly Phe Thr Phe Ser Tyr Tyr (SEQ ID NO: 54) | Asn Ile Ser Asn Gly Gly Ser Thr (SEQ ID NO: 56) | Asp Ala Arg Gln Asp Tyr Pro Ser Ile Thr Gly Val Leu Asn Ala (SEQ ID NO: 58) |
| 46-15-23 | Gly Phe Thr Phe Ser Tyr Asp (SEQ ID NO: 64) | Asn Ile Ser Pro Ser Gly Ser Thr (SEQ ID NO: 66) | Gly Ala Arg Leu Tyr Asp Gly Ser Tyr Tyr Arg Tyr Trp Phe Asp Phe (SEQ ID NO: 68) |
| 100-11 | Gly Phe Thr Phe Ser Tyr Tyr (SEQ ID NO: 74) | Asn Ile Ser Asn Gly Gly Asn Thr (SEQ ID NO: 76) | Gly Ala Arg Gln Asp Tyr Pro Ala Ile Thr Gly Val Met Asp Ala (SEQ ID NO: 78) |

TABLE 2

| Light chain | CDR1 | CDR2 | CDR3 |
|---|---|---|---|
| 25-1 | Gln Ser Leu Leu Tyr Ser Gly Asn Trp Ala Gln Lys Asn Tyr (SEQ ID NO: 20) | Ser | Gln Gln Tyr Tyr Asp Thr Pro Phe Thr (SEQ ID NO: 22) |
| 177-1 | Gln Ser Ile Ser Thr Ser (SEQ ID NO: 30) | Tyr Ala Ser | Gln Gln Ser Tyr Ser Ser Pro Leu Thr (SEQ ID NO: 32) |
| 82-30 | Gln Asn Leu Leu Tyr Ser Gly Asn Trp Ala Gln Lys Asn Tyr (SEQ ID NO: 40) | Ser | Gln Gln Tyr Tyr Asp Thr Pro Phe Thr (SEQ ID NO: 42) |
| 185-18 | Gln Ser Leu Leu Tyr Ser Gly Asn Trp Ala Gln Lys Asn Tyr (SEQ ID NO: 50) | Ser | Gln Gln Tyr Tyr Asp Thr Pro Phe Thr (SEQ ID NO: 52) |
| 180-10 | Gln Ser Leu Leu Tyr Ser Gly Asn Trp Ala Gln Lys Asn Tyr (SEQ ID NO: 60) | Ser | Gln Gln Tyr Tyr Asp Thr Pro Phe Thr (SEQ ID NO: 62) |
| 46-15-23 | Gln Ser Leu Val His Ser Asp Gly Arg Val Asn Thr Tyr (SEQ ID NO: 70) | Ser | Leu Gln Ser Thr His Phe Pro Leu Thr (SEQ ID NO: 72) |
| 100-11 | Gln Ser Leu Leu Tyr Ser Gly Asn Trp Ala Lys Thr Tyr (SEQ ID NO: 80) | Ser | Gln Gln Tyr Tyr Asp Thr Pro Phe Thr (SEQ ID NO: 82) |

(3) Binding Affinity to hDR6 and mDR6

A gene encoding hDR6 represented by SEQ ID NO: 1 was amplified by PCR by using a cDNA library prepared based on RNA extracted from Jurkat cells derived from human T lymphoma cells as a template, and DNA primers designed so that DNA encoding amino acids 1-371 region comprising the predicted signal sequence and a transmembrane domain was amplified. Similarly, a gene encoding mDR6 represented by SEQ ID NO: 3 was amplified by PCR by using a cDNA library prepared based on RNA extracted from DO11.10-T cells as a template, and DNA primers designed so that DNA encoding amino acids 1-371 region comprising the predicted signal sequence and a transmembrane domain was amplified. The primers were so designed that the amplified DNA has a restriction enzyme site BamHI in one terminus, and a restriction enzyme site EcoRI in the other terminus.

Each of the two kinds of amplified fragments was treated with restriction enzymes, and recombined into a retrovirus vector pMXsIG that was cleaved with the same restriction enzymes, to prepare expression plasmid pMXsIG encoding hDR6 and expression plasmid pMXsIG encoding mDR6. These plasmids were packaged by using PLAT-E cells to prepare viral particles. Mouse L929 cells were infected with the viral particles, and two kinds of transformed L929 cells expressing hDR6 or mDR6 were obtained.

Figure 17:
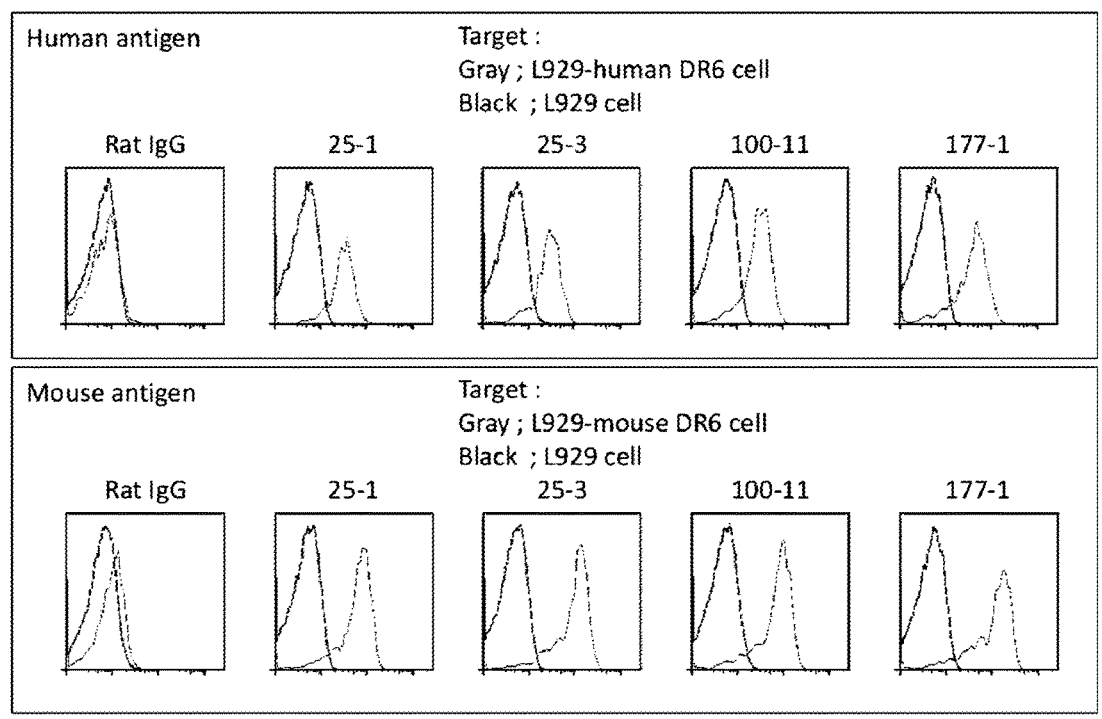
FIG. 17 includes charts showing the binding strength of monoclonal antibodies produced by clone 25-1, clone 25-3, clone 100-11 and clone 177-1, to transformed L929 cells expressing mDR6 or hDR6.

These two kinds of transformed L929 cells and the parent strain L929 cells were incubated for 1 hour at 4° C. in a culture medium containing a non-specific rat IgG (ratIgG), a monoclonal antibody produced by clone 25-1, clone 25-3, clone 100-11 and clone 177-1 respectively, and then washed twice, and incubated again for 1 hour at 4° C. in a culture medium containing labeled anti-rat IgG antibody, and washed twice, and then the binding strength of each antibody was measured by using flow cytometry. The result is shown in FIG. 17.

All monoclonal antibodies used in the present experiment showed reactivity with mDR6, and showed cross reaction with hDR6.

Example 6 Screening of Anti-DR6 Agonist Antibody

PCR amplification was carried out by using a cDNA library prepared based on RNA extracted from Jurkat cells as a template, and a forward primer added with an EcoRI recognition sequence and a reverse primer added with a NotI recognition sequence that were designed to amplify DNA encoding a transmembrane region and an intracellular domain of human CD40 (hCD40). Similarly, PCR amplification was carried out by using a forward primer added with an EcoRI recognition sequence and a reverse primer added with a EcoRI recognition sequence that were designed to amplify DNA encoding an extracellular domain of mDR6.

Two kinds of amplified fragments were treated with the aforementioned two kinds of restriction enzymes, and recombined into an expression vector pTracer-SV40 (available from Invitrogen) that was cleaved with the same restriction enzymes, to prepare an expression plasmid pmDR6-hCD40 encoding a chimera protein consisting of an extracellular domain of mDR6, and a transmembrane region and an intracellular domain of hCD40. The pmDR6-hCD40 was introduced into HEK293T cells together with an NFκB activation dependent firefly luciferase expression reporter plasmid, to obtain transformed HEK293T cells in which the chimera protein was arranged on the cell surface so that the extracellular domain of mDR6 was exposed. The transformed HEK293T cell is a cell that was modified to allow monitoring of signal transduction initiated by binding of ligand Sdc1 or an agonistic anti-DR6 antibody to the extracellular domain of DR6, by change in the activity of a reporter protein firefly luciferase.

Figure 18:
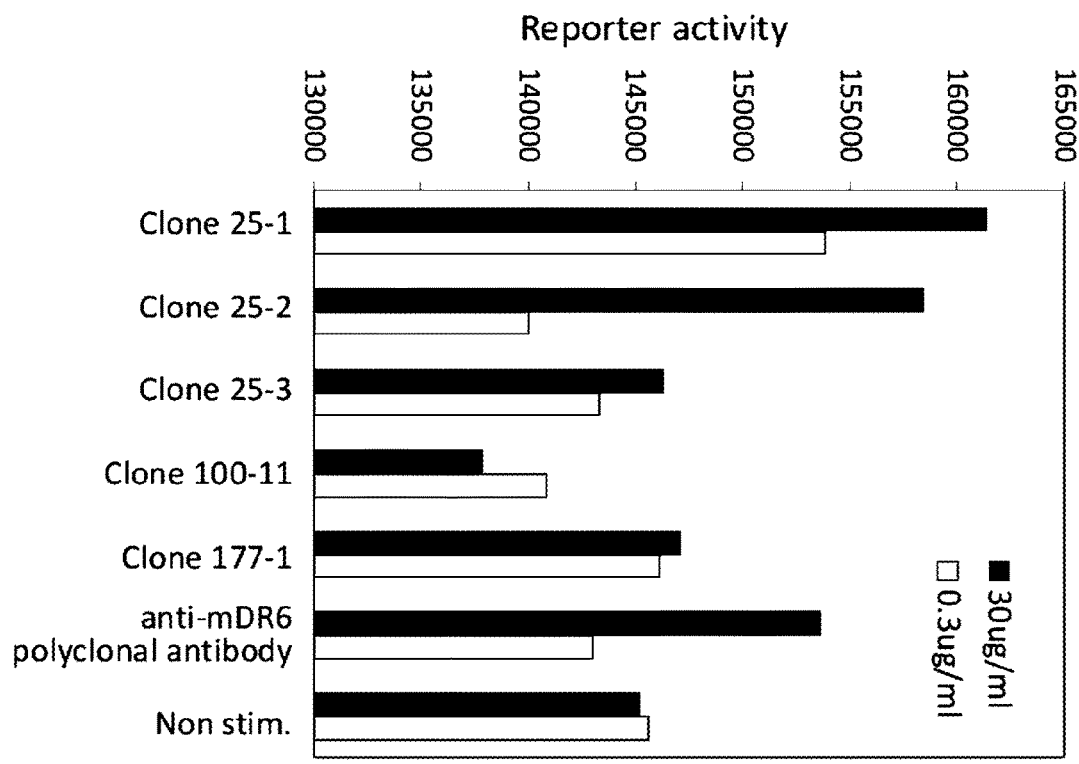
FIG. 18 is a graph showing the result of the action of monoclonal antibodies produced by clone 25-1, clone 25-2, clone 25-3, clone 100-11 and clone 177-1 examined by using a chimera protein consisting of an extracellular domain of mDR6, and a transmembrane region and an intracellular domain of mCD40.

The transformed HEK293T cells were inoculated into a 96-well cell culturing plate in which monoclonal antibodies produced by clone 25-1, clone 25-2, clone 25-3, clone 100-11 and clone 177-1 were immobilized in 30 μg/mL or 0.3 μg/mL, and incubated at 37° C. for 16 hours. The reporter protein activity in transformed HEK293T cells after incubation was measured by using Steady-Glo Luciferase Assay System (available from Promega). The result is shown in FIG. 18.

As a result, it was demonstrated that the monoclonal antibody produced by clone 25-1 was an anti-DR6 agonist antibody capable of significantly inducing signal transduction via DR6. An expression plasmid phDR6-hCD40 encoding a chimera protein consisting of an extracellular domain of hDR6, a transmembrane region and an intracellular domain of hCD40 was prepared by replacing mDR6 of pmDR6-hCD40 with hDR6, and subjected to the experiment as the above to confirm that this chimera protein also showed similar behavior.

Example 7 IL2 Production-Suppressing Effect of Monoclonal Antibody 25-1

An effect of monoclonal antibody 25-1 on CD3-dependent IL2 production in DO11.10-T cells/RPMI1640 culture medium was measured in the same condition as in (2) of Example 2 except that mSdc1-His was replaced with monoclonal antibody 25-1. The experiment in which mSdc1-His was replaced with a non-specific rat IgG was carried out as a control. The result is shown in FIG. 19.

Figure 19:
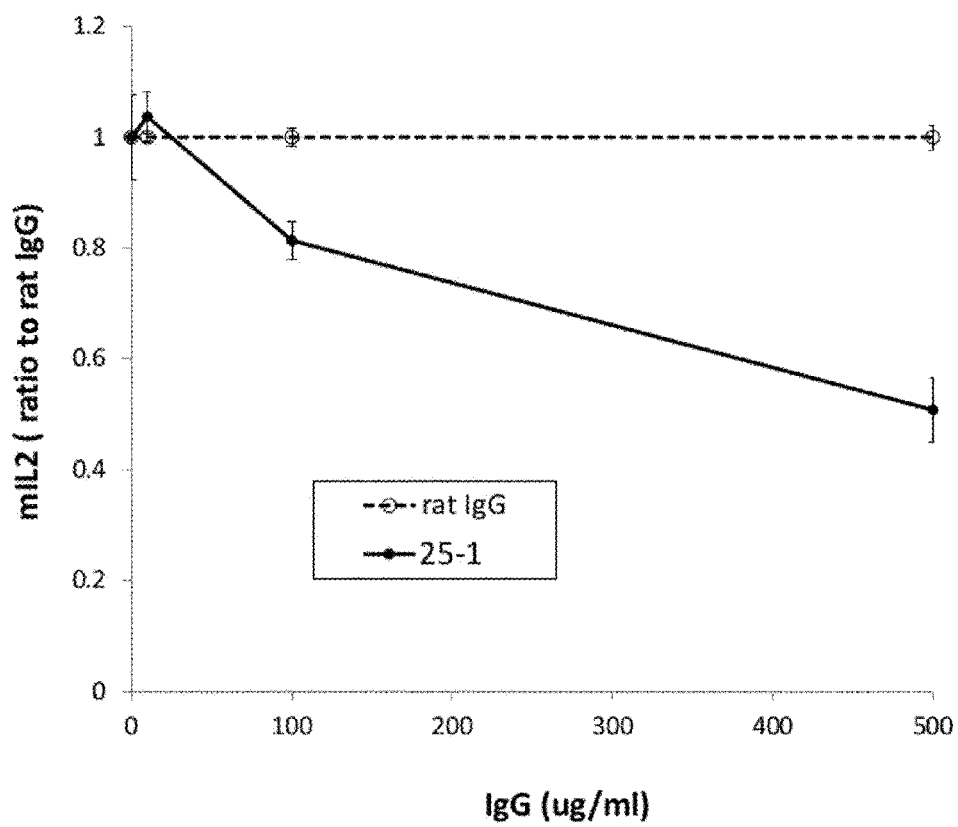
FIG. 19 is a graph showing the IL2 production suppressing effect of monoclonal antibody 25-1 on DO11.10-T cells.

As shown in FIG. 19, monoclonal antibody 25-1 suppressed IL2 production of DO11.10-T cells in a dose dependent manner.

Example 8 Evaluation of Anti-DR6 Antibody

Figure 20:
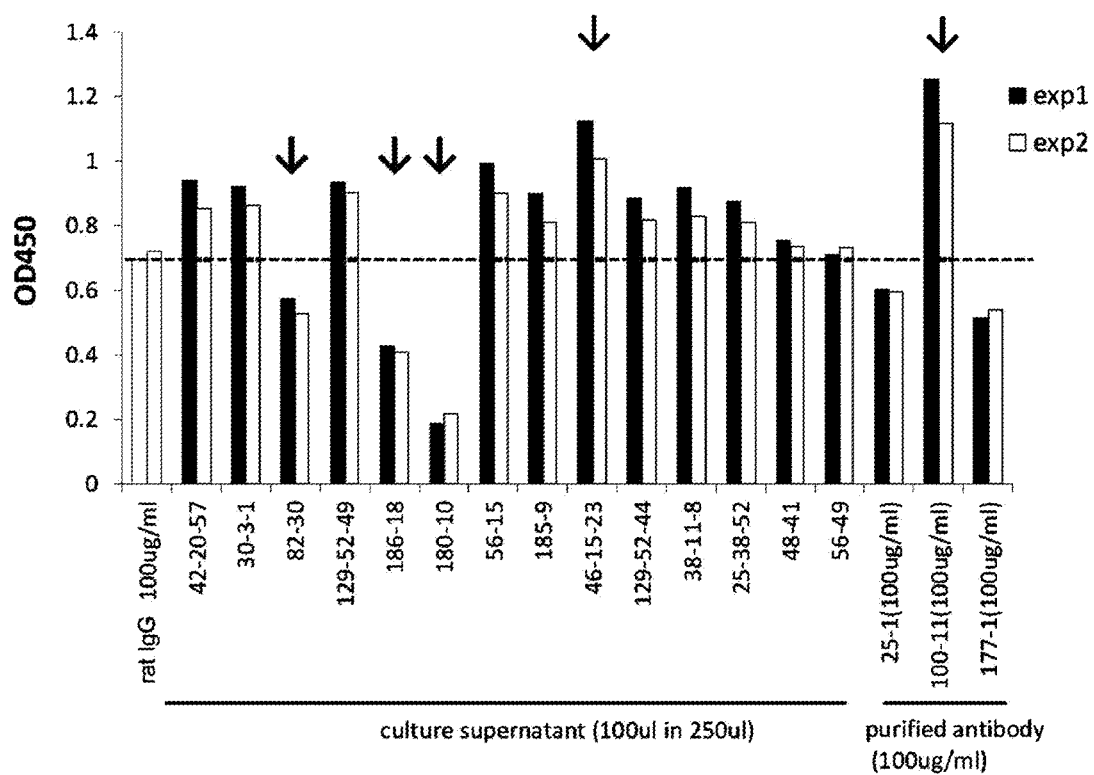
FIG. 20 is a graph showing the IL2 production level when a culture supernatant of anti-mDR6 antibody-producing hybridomas (100 μL) or a purified antibody therefrom (100 μg/mL) is added to a co-culture system of DO11.10-T cells and A20 cells pulsed with OVA peptide.

In a co-culture system of DO11.10-T cells and A20 cells pulsed with OVA peptide, a culture supernatant (100 μL) or a purified antibody (100 μg/mL) of the anti-mDR6 antibody producing hybridoma was added. IL2 contained in the culture supernatant at 48 hours after addition was measured by the ELISA method. The result is shown in FIG. 20.

From this experiment result, it was confirmed that clone 25-1, clone 177-1, clone 82-30, clone 186-18 and clone 180-10 were anti-DR6 agonist antibodies, and clone 46-15-23 and clone 100-11 were anti-DR6 antagonist antibodies.

Example 9 Sdc1 Expression in Systemic Lupus Erythematosus Model Animal

From normal B6 mice, and NZB/WF1 mice (available from Japan SLC, Inc.) which are known as model mice of systemic lupus erythematosus (SLE), serum was sampled at each time point of 4-month old (before onset of SLE), 6-month old (early phase of SLE onset) and 8-month old (later phase of SLE onset), and solubilized mSdc1 contained in serum was immune precipitated by using anti-mSdc1 antibody (available from Biolegend). The mSdc1 contained in each precipitate was detected by anti-mSdc1 antibody, and sugar chain bound to mSdc1 was detected by anti-heparan sulfate antibody 10E4 (available from SEIKAGAKU CORPORATION) which is a sugar chain specific antibody. The result is shown in FIG. 21.

Figure 21:
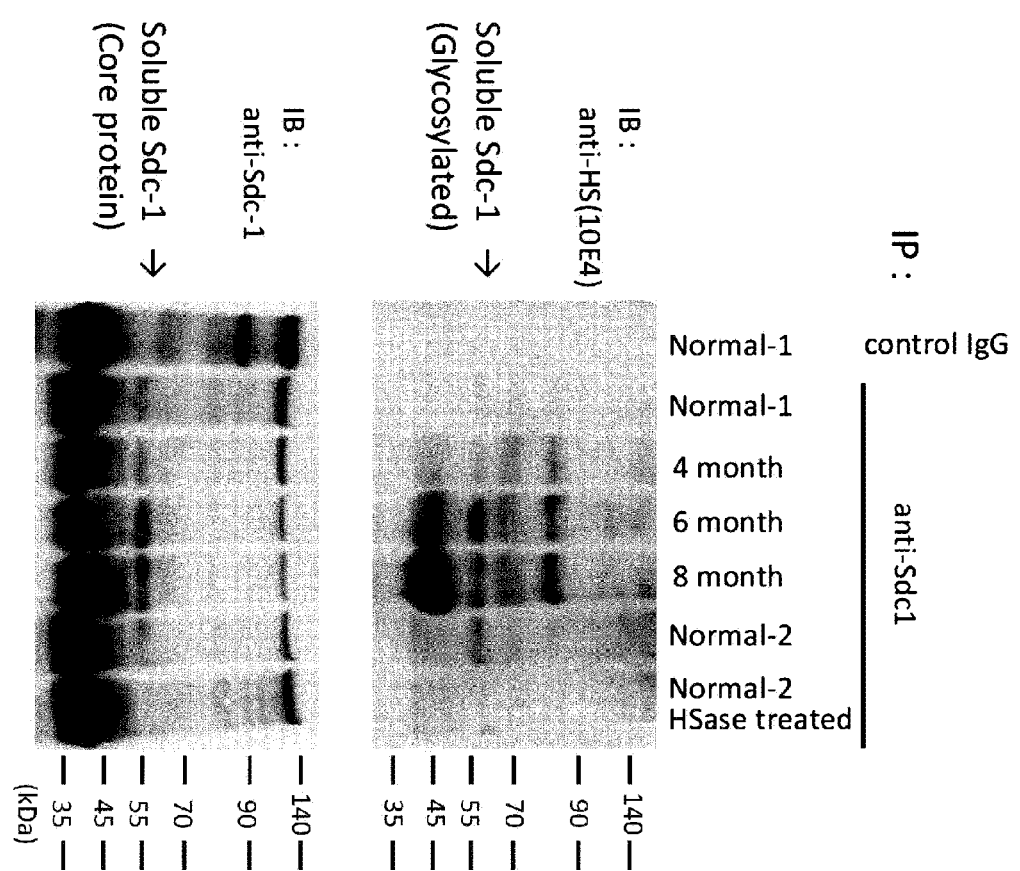
FIG. 21 is a photograph of immunoblotting showing the change in Sdc1 content in serum of systemic lupus erythematosus model animals.

As shown in FIG. 21, it was demonstrated that in comparison with normal mice or NZB/WF1 mice before SLE onset, the content of glycosylated solubilized mSdc1 increased in the early and later phases of SLE onset. Therefore, the content of solubilized Sdc1 in serum can be used as a biomarker capable of monitoring the progression of SLE.

Example 10 Construction of Solubilized DR6 Mutant (1) Preparation of Cysteine Rich Domain (CRD)-Deficient Solubilized mDR6

PCR amplification was carried out by using pcDNA/mDR6-hFcm as a template in which a gene encoding recombinant soluble mDR6 (mDR6-hFcm) consisting of an extracellular region of mDR6 represented by SEQ ID NO: 88 and a Fc region of human IgG was cloned, and DNA primers designed and synthesized so that DNA (SEQ ID NO: 89) encoding a modified extracellular domain of mDR6 (amino acid sequence thereof is represented by SEQ ID NO: 90) lacking CRD1 (amino acids at positions 66 to 105 in SEQ ID NO: 88) was amplified, to obtain pcDNA3/mDR6-hFcm deltaCRD1.

pcDNA3/mDR6-hFcm deltaCRD1 was introduced into HEK293T cells, and cultured for 7 days in a Freestyle 293 Expression culture medium (available from Invitrogen) to allow secretion of mDR6-hFcm deltaCRD1 into the culture medium, and mDR6-hFcm deltaCRD1 was purified by using a protein G-bound agarose column and then labeled.

Figure 22:
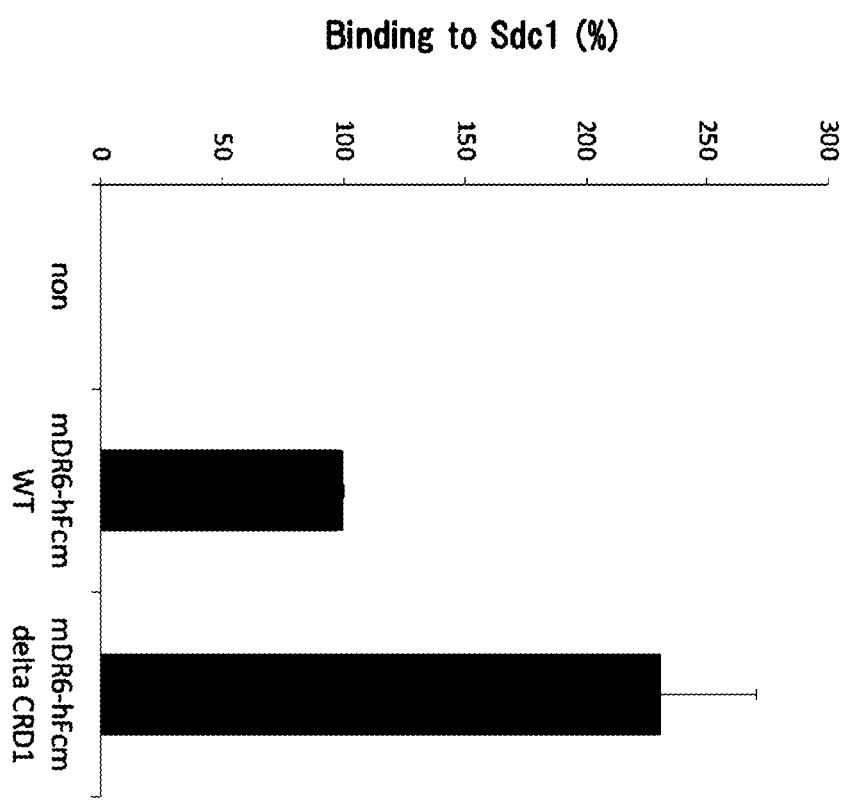
FIG. 22 is a graph showing the binding ability of normal mDR6 and a cysteine rich domain-deficient mDR6 mutant respectively, to transformed cells expressing mSdc1.

An expression vector (pMXsIG/mSdc1) into which a gene encoding mSdc1 (SEQ ID NO: 7) was incorporated in an expressible manner, and a control vector (pMXsIG) were introduced into DO11.10-T cells to prepare transformed cells. Binding abilities of these two kinds of transformed cells to labeled mDR6-hFcm and to labeled mDR6-hFcm deltaCRD1 was examined, and it was confirmed that binding ability of mDR6-hFcm deltaCRD1 increased to about 2.5 times of that of mDR6-hFcm (FIG. 22).

Example 11 Treatment Effect of Anti-DR6 Antibody in Model Animal (1) Eight SLE model mice were placed in an ordinary feeding environment, and fed up to 44-week-old with intraperitoneal administration of monoclonal antibody 25-1 (300 μg/animal/time/2 days) during period from 15-week-old to 27-week-old, and the survival rate and the incidence of proteinuria were measured. Urine protein was measured by the uropaper method, and an individual showing a value of more than or equal to 300 mg/dl was determined as positive. Also, eight SLE model mice to which rat IgG was intraperitoneally administered in place of monoclonal antibody 25-1 were provided as a control group. The results are shown in FIG. 23 and FIG. 24.

Figure 23:
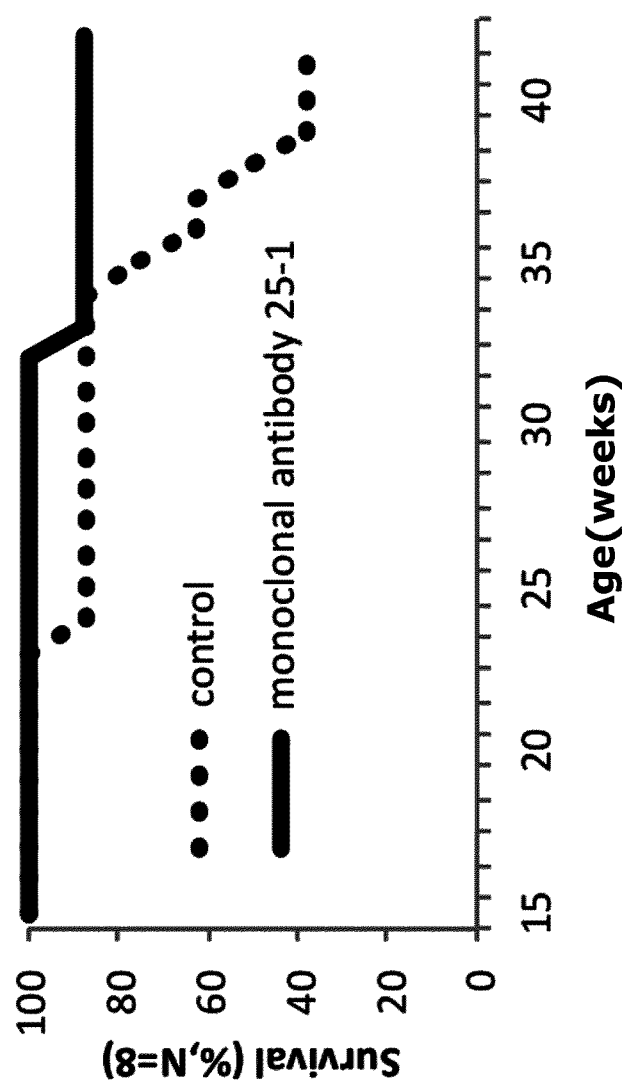
FIG. 23 is a graph showing the survival rate of systemic lupus erythematosus model mice (SLE model mice) administered with monoclonal antibody 25-1.

As shown in FIG. 23, the survival rate at 44-week-old was 87.5% in the group administered with monoclonal antibody 25-1, in contrast to 37.5% in the control group, revealing that the survival rate was improved by administration of monoclonal antibody 25-1.

Figure 24:
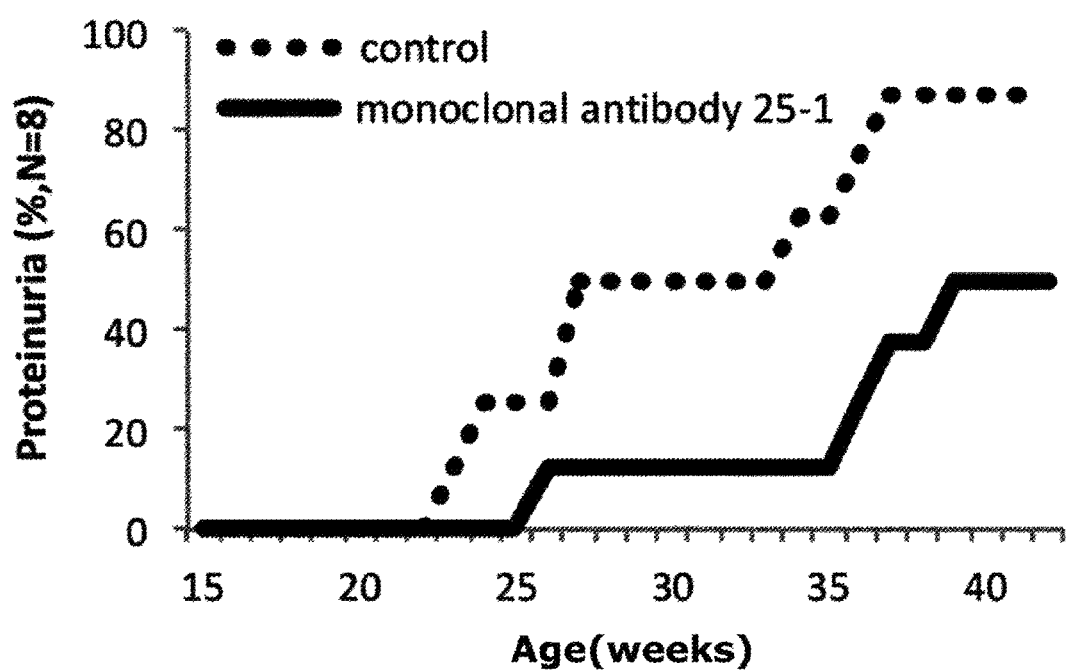
FIG. 24 is a graph showing the incidence of proteinuria in SLE model mice administered with monoclonal antibody 25-1.

Also as shown in FIG. 24, significant delay of onset of proteinuria was observed in the group administered with monoclonal antibody 25-1 in comparison with the control group.

Example 12 Response of Immune Cell by Administration of Anti-DR6 Agonist Antibody The whole splenocyte population was prepared from each of SLE model mice of 10-week-old (before SLE onset) and 24-week-old (after SLE onset) fed in the same condition as in Example 11 and normal mice of the same ages. Expression of T cell surface marker (CD3), DR6, helper T cell surface marker (CD4) and killer T cell surface marker (CD8) in the cell population was analyzed by flow cytometry using monoclonal antibody 25-1, anti-CD3 antibody, anti-CD4 antibody and anti-CD8 antibody. The result is shown in FIG. 25.

Figure 25:
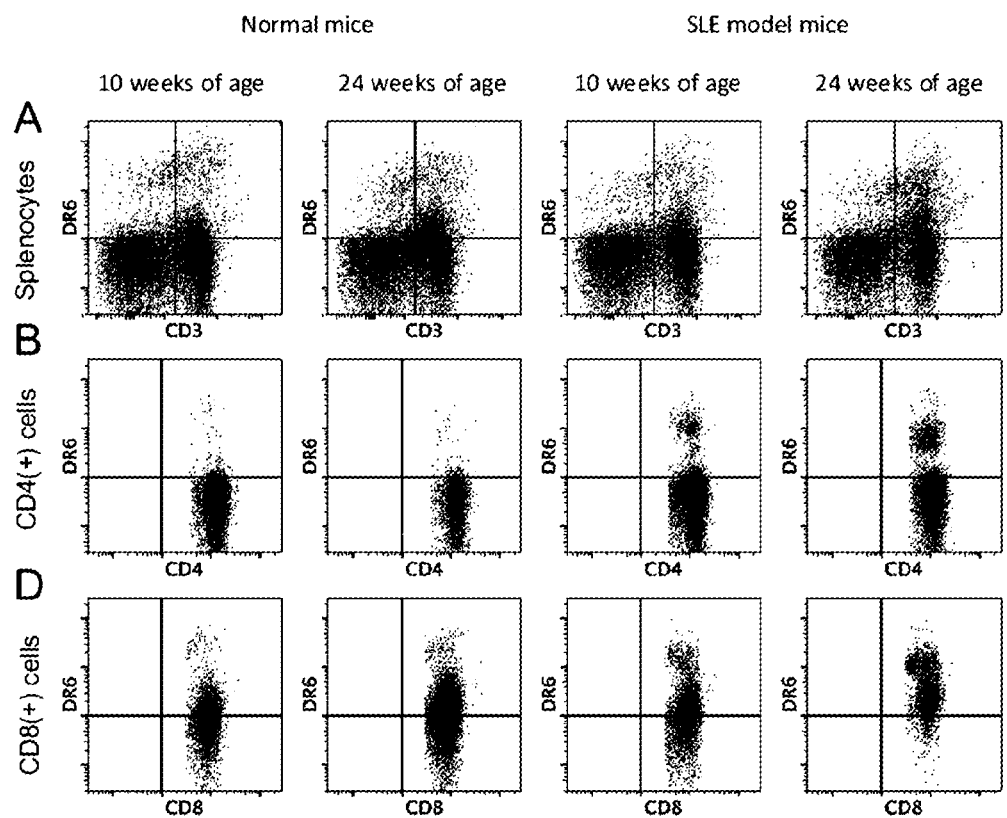
FIG. 25 includes charts showing the results of FACS analysis for cells expressing CD3, DR6, CD4 and CD8 respectively in the whole splenocyte population prepared from SLE model mice administered with monoclonal antibody 25-1.
Figure 26:
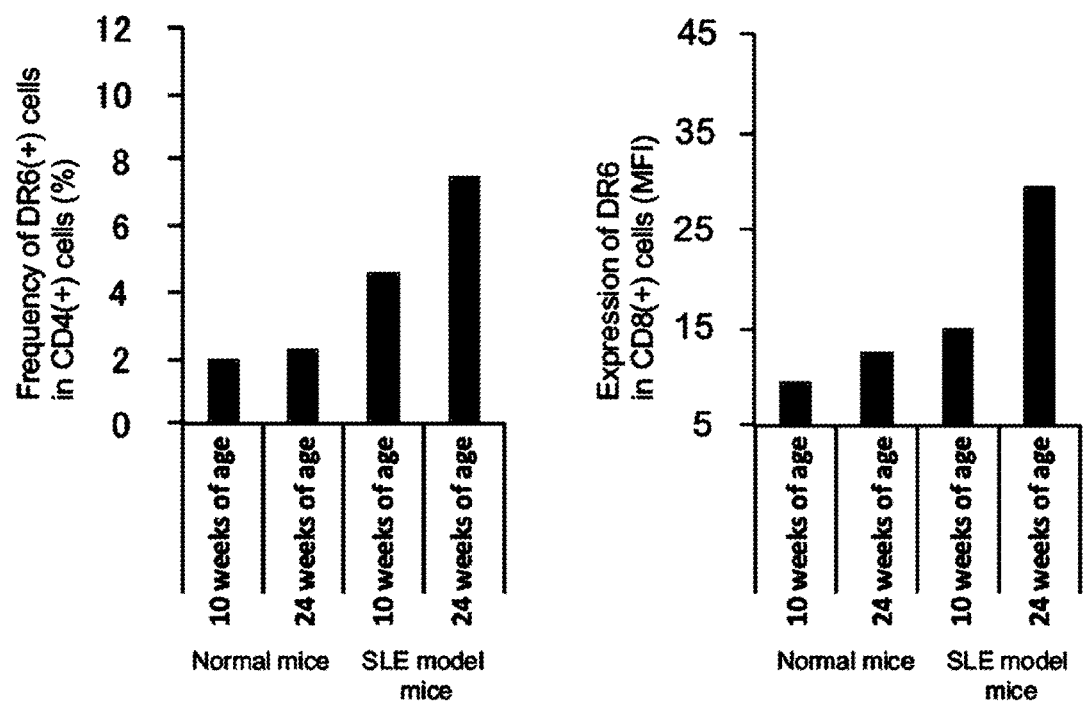
FIG. 26 is a graph showing the increases (average values) in the occurrence of DR6 positive cells observed in panel B and panel D in FIG. 25.

As shown in panel B of FIG. 25, in SLE model mice, an occurrence of CD4 positive cells showing a binding affinity with monoclonal antibody 25-1, namely DR6 positive helper T cells was observed in both of 10-week-old and 24-week-old. As shown in panel D, increase in the DR6 expression level of the whole CD8 positive cells was observed in 24-week-old of SLE model mice. The increases (average values) in the occurrence of DR6 positive cells observed in panel B and panel D in FIG. 25 are shown graphically in FIG. 26.

These results indicate that immune cells expressing DR6 increase as the systemic lupus erythematosus progresses in SLE model mice.

Figure 27:
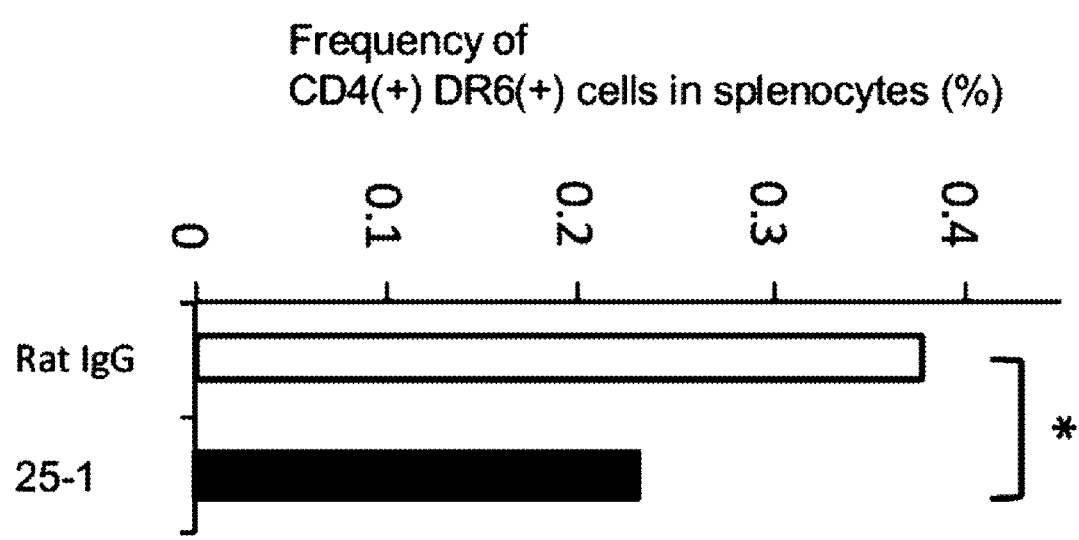
FIG. 27 is a graph indicating that the occurrence of CD4 positive cells (helper T cells) expressing DR6 decreases by administering monoclonal antibody 25-1 to SLE model mice in the onset phase of proteinuria.

Example 13 Response of Immune Cell by Administration of Anti-DR6 Agonist Antibody 24-week-old SLE model mice fed in the same condition as in Example 11 were fed for another 2 weeks with intraperitoneal administration of rat IgG or monoclonal antibody 25-1 (300 μg/animal/time/2 days). After the end of administration, the whole splenocyte population was prepared from mice of each group, and an occurrence of CD4 positive cells (helper T cells) expressing DR6 in the cell population was analyzed by flow cytometry in the same manner as in Example 12. The result (average value) is shown in FIG. 27 ($p<0.05$).

From this test, it was confirmed that the occurrence of CD4 positive cells expressing DR6 decreased by administering monoclonal antibody 25-1 to SLE model mice in the onset phase of proteinuria.

INDUSTRIAL APPLICABILITY

The immune regulating agent of the present invention can be used for treating or preventing diseases caused by excessive or abnormal immune response in mammals or diseases for which enhancement of immune function is desired in mammals, as an immune regulating agent based on a hitherto unknown mechanism, capable of regulating signal transduction induced by specific binding between DR6 and Sdc1.

0-1 Form PCT/RO/134 (SAFE)
0-1-1 The indication of the deposited microorganisms or other biological materials (PCT rule 13(2)) has been made by the right mentioned.
    JPO-PAS
    i221
0-2 International application No.
0-3 Applicant's or agent's file reference
    P13009WO
1 The indications made below relate to the deposited microorganism or other biological material referred to in the Detailed Description of the Invention.
1-1 Paragraph number
    0077
1-3 Identification of deposit
1-3-1 Name of depositary institution
    NPMD National Institute of Technology and Evaluation, Patent Microorganisms Depositary (NPMD)
1-3-2 Address of depositary institution
    2-5-8 Kazusakamatari, Kisarazu-shi, Chiba, Japan 292-0818
1-3-3 Date of deposit
    Oct. 27, 2014

1-3-4 Accession Number
 NPMD NITE BP-01729
1-5 Designated states for which indications are made
 All designated states
2 The indications made below relate to the deposited microorganism or other biological material referred to in the Detailed Description of the Invention.
2-1 Paragraph number
 0079
2-3 Identification of deposit
2-3-1 Name of depositary institution
 NPMD National Institute of Technology and Evaluation, Patent Microorganisms Depositary (NPMD)
2-3-2 Address of depositary institution
 2-5-8 Kazusakamatari, Kisarazu-shi, Chiba, Japan 292-0818
2-3-3 Date of deposit
 Oct. 27, 2014
2-3-4 Accession Number
 NPMD NITE BP-01730
2-5 Designated states for which indications are made
 All designated states
3 The indications made below relate to the deposited microorganism or other biological material referred to in the Detailed Description of the Invention.
3-1 Paragraph number
 0081
3-3 Identification of deposit
3-3-1 Name of depositary institution
 NPMD National Institute of Technology and Evaluation, Patent Microorganisms Depositary (NPMD)
3-3-2 Address of depositary institution
 2-5-8 Kazusakamatari, Kisarazu-shi, Chiba, Japan 292-0818
3-3-3 Date of deposit
 Oct. 27, 2014
3-3-4 Accession Number
 NPMD NITE BP-01731
3-5 Designated states for which indications are made
 All designated states
4 The indications made below relate to the deposited microorganism or other biological material referred to in the Detailed Description of the Invention.
4-1 Paragraph number
 0083
4-3 Identification of deposit
4-3-1 Name of depositary institution
 NPMD National Institute of Technology and Evaluation, Patent Microorganisms Depositary (NPMD)
4-3-2 Address of depositary institution
 2-5-8 Kazusakamatari, Kisarazu-shi, Chiba, Japan 292-0818
4-3-3 Date of deposit
 Oct. 27, 2014
4-3-4 Accession Number
 NPMD NITE BP-01732
4-5 Designated states for which indications are made
 All designated states
5 The indications made below relate to the deposited microorganism or other biological material referred to in the Detailed Description of the Invention.
5-1 Paragraph number
 0085
5-3 Identification of deposit
5-3-1 Name of depositary institution
 NPMD National Institute of Technology and Evaluation, Patent Microorganisms Depositary (NPMD)
5-3-2 Address of depositary institution
 2-5-8 Kazusakamatari, Kisarazu-shi, Chiba, Japan 292-0818
5-3-3 Date of deposit
 Oct. 27, 2014
5-3-4 Accession Number
 NPMD NITE BP-01733
5-5 Designated states for which indications are made
 All designated states
6 The indications made below relate to the deposited microorganism or other biological material referred to in the Detailed Description of the Invention.
6-1 Paragraph number
 0106
6-3 Identification of deposit
6-3-1 Name of depositary institution
 NPMD National Institute of Technology and Evaluation, Patent Microorganisms Depositary (NPMD)
6-3-2 Address of depositary institution
 2-5-8 Kazusakamatari, Kisarazu-shi, Chiba, Japan 292-0818
6-3-3 Date of deposit
 Oct. 27, 2014
6-3-4 Accession Number
 NPMD NITE BP-01734
6-5 Designated states for which indications are made
 All designated states
7 The indications made below relate to the deposited microorganism or other biological material referred to in the Detailed Description of the Invention.
7-1 Paragraph number
 0108
7-3 Identification of deposit
7-3-1 Name of depositary institution
 NPMD National Institute of Technology and Evaluation, Patent Microorganisms Depositary (NPMD)
7-3-2 Address of depositary institution
 2-5-8 Kazusakamatari, Kisarazu-shi, Chiba, Japan 292-0818
7-3-3 Date of deposit
 Oct. 27, 2014
7-3-4 Accession Number
 NPMD NITE BP-01735
7-5 Designated states for which indications are made
 All designated states

The invention claimed is:

1. A method for regulating IL-2 production by T cells expressing Death Receptor 6 in a mammal, comprising administering to the mammal an effective amount of a physiologically active substance, wherein the physiologically active substance is one or more anti-Death Receptor 6 antibodies selected from the group consisting of the following (a) to (g) and functional fragments thereof:

(a) an anti-Death Receptor 6 antibody comprising a heavy chain CDR1 consisting of the amino acid sequence represented by SEQ ID NO: 14, a heavy chain CDR2 consisting of the amino acid sequence represented by SEQ ID NO: 16, a heavy chain CDR3 consisting of the amino acid sequence represented by SEQ ID NO: 18, a light chain CDR1 consisting of the amino acid sequence represented by SEQ ID NO: 20, a light chain CDR2 consisting of the amino acid sequence of Trp- Ala-Ser, and a light chain CDR3 consisting of the amino acid sequence represented by SEQ ID NO: 22, (b) an anti-Death Receptor 6 antibody comprising a heavy chain CDR1 consisting of the amino acid sequence represented by SEQ ID NO: 24, a heavy chain CDR2 consisting of the amino acid sequence represented by SEQ ID NO: 26, a heavy chain CDR3 consisting of the amino acid sequence represented by SEQ ID NO: 28, a light chain CDR1 consisting of the amino acid sequence represented by SEQ ID NO: 30, a light chain CDR2 consisting of the amino acid sequence of Tyr-Ala-Ser, and a light chain CDR3 consisting of the amino acid sequence represented by SEQ ID NO: 32, (c) an anti-Death Receptor 6 antibody comprising a heavy chain CDR1 consisting of the amino acid sequence represented by SEQ ID NO: 34, a heavy chain CDR2 consisting of the amino acid sequence represented by SEQ ID NO: 36, a heavy chain CDR3 consisting of the amino acid sequence represented by SEQ ID NO: 38, a light chain CDR1 consisting of the amino acid sequence represented by SEQ ID NO: 40, a light chain CDR2 consisting of the amino acid sequence of Trp-Ala-Ser, and a light chain CDR3 consisting of the amino acid sequence represented by SEQ ID NO: 42, (d) an anti-Death Receptor 6 antibody comprising a heavy chain CDR1 consisting of the amino acid sequence represented by SEQ ID NO: 44, a heavy chain CDR2 consisting of the amino acid sequence represented by SEQ ID NO: 46, a heavy chain CDR3 consisting of the amino add sequence represented by SEQ ID NO: 48, a light chain CDR1 consisting of the amino acid sequence represented by SEQ ID NO: 50, a light chain CDR2 consisting of the amino acid sequence of Trp-Ala-Ser, and a light chain CDR3 consisting of the amino add sequence represented by SEQ ID NO: 52, (e) an anti-Death Receptor 6 antibody comprising a heavy chain CDR1 consisting of the amino acid sequence represented by SEQ ID NO: 54, a heavy chain CDR2 consisting of the amino acid sequence represented by SEQ ID NO: 56, a heavy chain CDR3 consisting of the amino acid sequence represented by SEQ ID NO: 58, a light chain CDR1 consisting of the amino acid sequence represented by SEQ ID NO: 60, a light chain CDR2 consisting of the amino acid sequence of Trp-Ala-Ser, and a light chain CDR3 consisting of the amino acid sequence represented by SEQ ID NO: 62, (f) an anti-Death Receptor 6 antibody comprising a heavy chain CDR1 consisting of the amino acid sequence represented by SEQ ID NO: 64, a heavy chain CDR2 consisting of the amino acid sequence represented by SEQ ID NO: 66, a heavy chain CDR3 consisting of the amino add sequence represented by SEQ ID NO: 68, a light chain CDR1 consisting of the amino acid sequence represented by SEQ ID NO: 70, a light chain CDR2 consisting of the amino acid sequence of Arg-Val-Ser, and a light chain CDR3 consisting of the amino acid sequence represented by SEQ ID NO: 72, and (g) an anti-Death Receptor 6 antibody comprising a heavy chain CDR1 consisting of the amino add sequence represented by SEQ ID NO: 74, a heavy chain CDR2 consisting of the amino acid sequence represented by SEQ ID NO: 76, a heavy chain CDR3 consisting of the amino acid sequence represented by SEQ ID NO: 78, a light chain CDR1 consisting of the amino acid sequence represented by SEQ ID NO: 80, a light chain CDR2 consisting of the amino acid sequence of Trp-Ala-Ser, and a light chain CDR3 consisting of the amino acid sequence represented by SEQ ID NO: 82.

2. The method according to claim 1, wherein the physiologically active substance is (a) an anti-Death Receptor 6 antibody comprising a heavy chain CDR1 consisting of the amino acid sequence represented by SEQ ID NO: 14, a heavy chain CDR2 consisting of the amino acid sequence represented by SEQ ID NO: 16, a heavy chain CDR3 consisting of the amino acid sequence represented by SEQ ID NO: 18, a light chain CDR1 consisting of the amino acid sequence represented by SEQ ID NO: 20, a light chain CDR2 consisting of the amino acid sequence of Trp-Ala-Ser, and a light chain CDR3 consisting of the amino add sequence represented by SEQ ID NO: 22.

3. The method according to claim 1, wherein the physiologically active substance is (b) an anti-Death Receptor 6 antibody comprising a heavy chain CDR1 consisting of the amino acid sequence represented by SEQ ID NO: 24, a heavy chain CDR2 consisting of the amino acid sequence represented by SEQ ID NO: 26, a heavy chain CDR3 consisting of the amino acid sequence represented by SEQ ID NO: 28, a light chain CDR1 consisting of the amino acid sequence represented by SEQ ID NO: 30, a light chain CDR2 consisting of the amino acid sequence of Tyr-Ala-Ser, and a light chain CDR3 consisting of the amino acid sequence represented by SEQ ID NO: 32.

4. The method according to claim 1, wherein the physiologically active substance is (c) an anti-Death Receptor 6 antibody comprising a heavy chain CDR1 consisting of the amino acid sequence represented by SEQ ID NO: 34, a heavy chain CDR2 consisting of the amino acid sequence represented by SEQ ID NO: 36, a heavy chain CDR3 consisting of the amino acid sequence represented by SEQ ID NO: 38, a light chain CDR1 consisting of the amino acid sequence represented by SEQ ID NO: 40, a light chain CDR2 consisting of the amino acid sequence of Trp-Ala-Ser, and a light chain CDR3 consisting of the amino acid sequence represented by SEQ ID NO: 42.

5. The method according to claim 1, wherein the physiologically active substance is (d) an anti-Death Receptor 6 antibody comprising a heavy chain CDR1 consisting of the amino acid sequence represented by SEQ ID NO: 44, a heavy chain CDR2 consisting of the amino acid sequence represented by SEQ ID NO: 46, a heavy chain CDR3 consisting of the amino acid sequence represented by SEQ ID NO: 48, a light chain CDR1 consisting of the amino acid sequence represented by SEQ ID NO: 50, a light chain CDR2 consisting of the amino acid sequence of Trp-Ala-Ser, and a light chain CDR3 consisting of the amino acid sequence represented by SEQ ID NO: 52.

6. The method according to claim 1, wherein the physiologically active substance is (e) an anti-Death Receptor 6 antibody comprising a heavy chain CDR1 consisting of the amino acid sequence represented by SEQ ID NO: 54, a heavy chain CDR2 consisting of the amino acid sequence represented by SEQ ID NO: 56, a heavy chain CDR3 consisting of the amino acid sequence represented by SEQ ID NO: 58, a light chain CDR1 consisting of the amino acid sequence represented by SEQ ID NO: 60, a light chain CDR2 consisting of the amino acid sequence of Trp-Ala-Ser, and a light chain CDR3 consisting of the amino acid sequence represented by SEQ ID NO: 62.

7. The method according to claim 1, wherein the physiologically active substance is (f) an anti-Death Receptor 6 antibody comprising a heavy chain CDR1 consisting of the amino acid sequence represented by SEQ ID NO: 64, a heavy chain CDR2 consisting of the amino acid sequence represented by SEQ ID NO: 66, a heavy chain CDR3 consisting of the amino acid sequence represented by SEQ ID NO: 68, a light chain CDR1 consisting of the amino acid sequence represented by SEQ ID NO: 70, a light chain CDR2 consisting of the amino acid sequence of Arg-Val-Ser, and a light chain CDR3 consisting of the amino add sequence represented by SEQ ID NO: 72.

8. The method according to claim 1, wherein the physiologically active substance is (g) an anti-Death Receptor 6 antibody comprising a heavy chain CDR1 consisting of the amino acid sequence represented by SEQ ID NO: 74, a heavy chain CDR2 consisting of the amino acid sequence represented by SEQ ID NO: 76, a heavy chain CDR3 consisting of the amino acid sequence represented by SEQ ID NO: 78, a light chain CDR1 consisting of the amino acid sequence represented by SEQ ID NO: 80, a light chain CDR2 consisting of the amino acid sequence of Trp-Ala-Ser, and a light chain CDR3 consisting of the amino acid sequence represented by SEQ ID NO: 82.

9. A method for suppressing proliferation of CD4+ T cells expressing Death Receptor 6 in a mammal, comprising administering to the mammal an effective amount of a physiologically active substance,
wherein the physiologically active substance is an anti-Death Receptor 6 antibody comprising a heavy chain CDR1 consisting of the amino acid sequence represented by SEQ ID NO: 14, a heavy chain CDR2 consisting of the amino acid sequence represented by SEQ ID NO: 16, a heavy chain CDR3 consisting of the amino acid sequence represented by SEQ ID NO: 18, a light chain CDR1 consisting of the amino acid sequence represented by SEQ ID NO: 20, a light chain CDR2 consisting of the amino acid sequence of Trp-Ala-Ser, and a light chain CDR3 consisting of the amino acid sequence represented by SEQ ID NO: 22.

10. A method for treating systemic lupus erythematosus (SLE) in a mammal, comprising administering to the mammal an effective amount of an anti-Death Receptor 6 antibody, wherein the antibody comprises a heavy chain CDR1 consisting of the amino acid sequence represented by SEQ ID NO: 14, a heavy chain CDR2 consisting of the amino acid sequence represented by SEQ ID NO: 16, a heavy chain CDR3 consisting of the amino add sequence represented by SEQ ID NO: 18, a light chain CDR1 consisting of the amino acid sequence represented by SEQ ID NO: 20, a light chain CDR2 consisting of the amino acid sequence of Trp-Ala-Ser, and a light chain CDR3 consisting of the amino acid sequence represented by SEQ ID NO: 22.

* * * * *

SEQUENCE LISTING

<160> NUMBER OF SEQ ID NOS: 90

<210> SEQ ID NO 1
<211> LENGTH: 1968
<212> TYPE: DNA
<213> ORGANISM: Homo sapiens -continued

<220> FEATURE:
<221> NAME/KEY: CDS
<222> LOCATION: (1)..(1968)

<400> SEQUENCE: 1

```
atg ggg acc tct ccg agc agc agc acc gcc ctc gcc tcc tgc agc cgc      48
Met Gly Thr Ser Pro Ser Ser Ser Thr Ala Leu Ala Ser Cys Ser Arg
1               5                   10                  15 atc gcc cgc cga gcc aca gcc acg atg atc gcg ggc tcc ctt ctc ctg      96
Ile Ala Arg Arg Ala Thr Ala Thr Met Ile Ala Gly Ser Leu Leu Leu
                20                  25                  30 ctt gga ttc ctt agc acc acc aca gct cag cca gaa cag aag gcc tcg     144
Leu Gly Phe Leu Ser Thr Thr Thr Ala Gln Pro Glu Gln Lys Ala Ser
        35                  40                  45 aat ctc att ggc aca tac cgc cat gtt gac cgt gcc acc ggc cag gtg     192
Asn Leu Ile Gly Thr Tyr Arg His Val Asp Arg Ala Thr Gly Gln Val
    50                  55                  60 cta acc tgt gac aag tgt cca gca gga acc tat gtc tct gag cat tgt     240
Leu Thr Cys Asp Lys Cys Pro Ala Gly Thr Tyr Val Ser Glu His Cys
65                  70                  75                  80 acc aac aca agc ctg cgc gtc tgc agc agt tgc cct gtg ggg acc ttt     288
Thr Asn Thr Ser Leu Arg Val Cys Ser Ser Cys Pro Val Gly Thr Phe
                85                  90                  95 acc agg cat gag aat ggc ata gag aaa tgc cat gac tgt agt cag cca     336
Thr Arg His Glu Asn Gly Ile Glu Lys Cys His Asp Cys Ser Gln Pro
                100                 105                 110 tgc cca tgg cca atg att gag aaa tta cct tgt gct gcc ttg act gac     384
Cys Pro Trp Pro Met Ile Glu Lys Leu Pro Cys Ala Ala Leu Thr Asp
        115                 120                 125 cga gaa tgc act tgc cca cct ggc atg ttc cag tct aac gct acc tgt     432
Arg Glu Cys Thr Cys Pro Pro Gly Met Phe Gln Ser Asn Ala Thr Cys
    130                 135                 140 gcc ccc cat acg gtg tgt cct gtg ggt tgg ggt gtg cgg aag aaa ggg     480
Ala Pro His Thr Val Cys Pro Val Gly Trp Gly Val Arg Lys Lys Gly
145                 150                 155                 160 aca gag act gag gat gtg cgg tgt aag cag tgt gct cgg ggt acc ttc     528
Thr Glu Thr Glu Asp Val Arg Cys Lys Gln Cys Ala Arg Gly Thr Phe
                165                 170                 175 tca gat gtg cct tct agt gtg atg aaa tgc aaa gca tac aca gac tgt     576
Ser Asp Val Pro Ser Ser Val Met Lys Cys Lys Ala Tyr Thr Asp Cys
                180                 185                 190 ctg agt cag aac ctg gtg gtg atc aag ccg ggg acc aag gag aca gac     624
Leu Ser Gln Asn Leu Val Val Ile Lys Pro Gly Thr Lys Glu Thr Asp
        195                 200                 205 aac gtc tgt ggc aca ctc ccg tcc ttc tcc agc tcc acc tca cct tcc     672
Asn Val Cys Gly Thr Leu Pro Ser Phe Ser Ser Ser Thr Ser Pro Ser
    210                 215                 220 cct ggc aca gcc atc ttt cca cgc cct gag cac atg gaa acc cat gaa     720
Pro Gly Thr Ala Ile Phe Pro Arg Pro Glu His Met Glu Thr His Glu
225                 230                 235                 240 gtc cct tcc tcc act tat gtt ccc aaa ggc atg aac tca aca gaa tcc     768
Val Pro Ser Ser Thr Tyr Val Pro Lys Gly Met Asn Ser Thr Glu Ser
                245                 250                 255 aac tct tct gcc tct gtt aga cca aag gta ctg agt agc atc cag gaa     816
Asn Ser Ser Ala Ser Val Arg Pro Lys Val Leu Ser Ser Ile Gln Glu
                260                 265                 270 ggg aca gtc cct gac aac aca agc tca gca agg ggg aag gaa gac gtg     864
Gly Thr Val Pro Asp Asn Thr Ser Ser Ala Arg Gly Lys Glu Asp Val
        275                 280                 285 aac aag acc ctc cca aac ctt cag gta gtc aac cac cag caa ggc ccc     912
```

|     |     |     |     |     |     |     |     |     |     |     |     |     |     |      |
|-----|-----|-----|-----|-----|-----|-----|-----|-----|-----|-----|-----|-----|-----|------|
| Asn | Lys | Thr | Leu | Pro | Asn | Leu | Gln | Val | Val | Asn | His | Gln | Gln | Gly Pro |
|     | 290 |     |     |     | 295 |     |     |     |     | 300 |     |     |     |      |

| cac | cac | aga | cac | atc | ctg | aag | ctg | ctg | ccg | tcc | atg | gag | gcc | act | ggg | 960 |
|-----|-----|-----|-----|-----|-----|-----|-----|-----|-----|-----|-----|-----|-----|-----|-----|-----|
| His | His | Arg | His | Ile | Leu | Lys | Leu | Leu | Pro | Ser | Met | Glu | Ala | Thr | Gly |     |
| 305 |     |     |     | 310 |     |     |     |     | 315 |     |     |     |     | 320 |     |     |

| ggc | gag | aag | tcc | agc | acg | ccc | atc | aag | ggc | ccc | aag | agg | gga | cat | cct | 1008 |
|-----|-----|-----|-----|-----|-----|-----|-----|-----|-----|-----|-----|-----|-----|-----|-----|------|
| Gly | Glu | Lys | Ser | Ser | Thr | Pro | Ile | Lys | Gly | Pro | Lys | Arg | Gly | His | Pro |      |
|     |     |     |     | 325 |     |     |     |     | 330 |     |     |     |     | 335 |     |      |

| aga | cag | aac | cta | cac | aag | cat | ttt | gac | atc | aat | gag | cat | ttg | ccc | tgg | 1056 |
|-----|-----|-----|-----|-----|-----|-----|-----|-----|-----|-----|-----|-----|-----|-----|-----|------|
| Arg | Gln | Asn | Leu | His | Lys | His | Phe | Asp | Ile | Asn | Glu | His | Leu | Pro | Trp |      |
|     |     |     |     | 340 |     |     |     | 345 |     |     |     |     | 350 |     |     |      |

| atg | att | gtg | ctt | ttc | ctg | ctg | gtg | ctt | gtg | gtg | att | gtg | gtg | tgc |     | 1104 |
|-----|-----|-----|-----|-----|-----|-----|-----|-----|-----|-----|-----|-----|-----|-----|-----|------|
| Met | Ile | Val | Leu | Phe | Leu | Leu | Val | Leu | Val | Val | Ile | Val | Val | Cys |     |      |
|     |     |     |     | 355 |     |     |     |     | 360 |     |     |     |     | 365 |     |      |

| agt | atc | cgg | aaa | agc | tcg | agg | act | ctg | aaa | aag | ggg | ccc | cgg | cag | gat | 1152 |
|-----|-----|-----|-----|-----|-----|-----|-----|-----|-----|-----|-----|-----|-----|-----|-----|------|
| Ser | Ile | Arg | Lys | Ser | Ser | Arg | Thr | Leu | Lys | Lys | Gly | Pro | Arg | Gln | Asp |      |
|     | 370 |     |     |     |     | 375 |     |     |     |     | 380 |     |     |     |     |      |

| ccc | agt | gcc | att | gtg | gaa | aag | gca | ggg | ctg | aag | aaa | tcc | atg | act | cca | 1200 |
|-----|-----|-----|-----|-----|-----|-----|-----|-----|-----|-----|-----|-----|-----|-----|-----|------|
| Pro | Ser | Ala | Ile | Val | Glu | Lys | Ala | Gly | Leu | Lys | Lys | Ser | Met | Thr | Pro |      |
| 385 |     |     |     |     | 390 |     |     |     |     | 395 |     |     |     |     | 400 |      |

| acc | cag | aac | cgg | gag | aaa | tgg | atc | tac | tac | tgc | aat | ggc | cat | ggt | atc | 1248 |
|-----|-----|-----|-----|-----|-----|-----|-----|-----|-----|-----|-----|-----|-----|-----|-----|------|
| Thr | Gln | Asn | Arg | Glu | Lys | Trp | Ile | Tyr | Tyr | Cys | Asn | Gly | His | Gly | Ile |      |
|     |     |     |     | 405 |     |     |     |     | 410 |     |     |     |     | 415 |     |      |

| gat | atc | ctg | aag | ctt | gta | gca | gcc | caa | gtg | gga | agc | cag | tgg | aaa | gat | 1296 |
|-----|-----|-----|-----|-----|-----|-----|-----|-----|-----|-----|-----|-----|-----|-----|-----|------|
| Asp | Ile | Leu | Lys | Leu | Val | Ala | Ala | Gln | Val | Gly | Ser | Gln | Trp | Lys | Asp |      |
|     |     |     | 420 |     |     |     |     | 425 |     |     |     |     | 430 |     |     |      |

| atc | tat | cag | ttt | ctt | tgc | aat | gcc | agt | gag | agg | gag | gtt | gct | gct | ttc | 1344 |
|-----|-----|-----|-----|-----|-----|-----|-----|-----|-----|-----|-----|-----|-----|-----|-----|------|
| Ile | Tyr | Gln | Phe | Leu | Cys | Asn | Ala | Ser | Glu | Arg | Glu | Val | Ala | Ala | Phe |      |
|     |     | 435 |     |     |     |     | 440 |     |     |     |     | 445 |     |     |     |      |

| tcc | aat | ggg | tac | aca | gcc | gac | cac | gag | cgg | gcc | tac | gca | gct | ctg | cag | 1392 |
|-----|-----|-----|-----|-----|-----|-----|-----|-----|-----|-----|-----|-----|-----|-----|-----|------|
| Ser | Asn | Gly | Tyr | Thr | Ala | Asp | His | Glu | Arg | Ala | Tyr | Ala | Ala | Leu | Gln |      |
|     | 450 |     |     |     |     | 455 |     |     |     |     | 460 |     |     |     |     |      |

| cac | tgg | acc | atc | cgg | ggc | ccc | gag | gcc | agc | ctc | gcc | cag | cta | att | agc | 1440 |
|-----|-----|-----|-----|-----|-----|-----|-----|-----|-----|-----|-----|-----|-----|-----|-----|------|
| His | Trp | Thr | Ile | Arg | Gly | Pro | Glu | Ala | Ser | Leu | Ala | Gln | Leu | Ile | Ser |      |
| 465 |     |     |     |     | 470 |     |     |     |     | 475 |     |     |     |     | 480 |      |

| gcc | ctg | cgc | cag | cac | cgg | aga | aac | gat | gtt | gtg | gag | aag | att | cgt | ggg | 1488 |
|-----|-----|-----|-----|-----|-----|-----|-----|-----|-----|-----|-----|-----|-----|-----|-----|------|
| Ala | Leu | Arg | Gln | His | Arg | Arg | Asn | Asp | Val | Val | Glu | Lys | Ile | Arg | Gly |      |
|     |     |     |     | 485 |     |     |     |     | 490 |     |     |     |     | 495 |     |      |

| ctg | atg | gaa | gac | acc | acc | cag | ctg | gaa | act | gac | aaa | cta | gct | ctc | ccg | 1536 |
|-----|-----|-----|-----|-----|-----|-----|-----|-----|-----|-----|-----|-----|-----|-----|-----|------|
| Leu | Met | Glu | Asp | Thr | Thr | Gln | Leu | Glu | Thr | Asp | Lys | Leu | Ala | Leu | Pro |      |
|     |     |     | 500 |     |     |     |     | 505 |     |     |     |     | 510 |     |     |      |

| atg | agc | ccc | agc | ccg | ctt | agc | ccg | agc | ccc | atc | ccc | agc | ccc | aac | gcg | 1584 |
|-----|-----|-----|-----|-----|-----|-----|-----|-----|-----|-----|-----|-----|-----|-----|-----|------|
| Met | Ser | Pro | Ser | Pro | Leu | Ser | Pro | Ser | Pro | Ile | Pro | Ser | Pro | Asn | Ala |      |
|     |     | 515 |     |     |     |     | 520 |     |     |     |     | 525 |     |     |     |      |

| aaa | ctt | gag | aat | tcc | gct | ctc | ctg | acg | gtg | gag | cct | tcc | cca | cag | gac | 1632 |
|-----|-----|-----|-----|-----|-----|-----|-----|-----|-----|-----|-----|-----|-----|-----|-----|------|
| Lys | Leu | Glu | Asn | Ser | Ala | Leu | Leu | Thr | Val | Glu | Pro | Ser | Pro | Gln | Asp |      |
| 530 |     |     |     |     | 535 |     |     |     |     | 540 |     |     |     |     |     |      |

| aag | aac | aag | ggc | ttc | ttc | gtg | gat | gag | tcg | gag | ccc | ctt | ctc | cgc | tgt | 1680 |
|-----|-----|-----|-----|-----|-----|-----|-----|-----|-----|-----|-----|-----|-----|-----|-----|------|
| Lys | Asn | Lys | Gly | Phe | Phe | Val | Asp | Glu | Ser | Glu | Pro | Leu | Leu | Arg | Cys |      |
| 545 |     |     |     |     | 550 |     |     |     |     | 555 |     |     |     |     | 560 |      |

| gac | tct | aca | tcc | agc | ggc | tcc | tcc | gcg | ctg | agc | agg | aac | ggt | tcc | ttt | 1728 |
|-----|-----|-----|-----|-----|-----|-----|-----|-----|-----|-----|-----|-----|-----|-----|-----|------|
| Asp | Ser | Thr | Ser | Ser | Gly | Ser | Ser | Ala | Leu | Ser | Arg | Asn | Gly | Ser | Phe |      |
|     |     |     |     | 565 |     |     |     |     | 570 |     |     |     |     | 575 |     |      |

| att | acc | aaa | gaa | aag | aag | gac | aca | gtg | ttg | cgg | cag | gta | cgc | ctg | gac | 1776 |
|-----|-----|-----|-----|-----|-----|-----|-----|-----|-----|-----|-----|-----|-----|-----|-----|------|
| Ile | Thr | Lys | Glu | Lys | Lys | Asp | Thr | Val | Leu | Arg | Gln | Val | Arg | Leu | Asp |      |
|     |     |     |     | 580 |     |     |     |     | 585 |     |     |     |     | 590 |     |      |

| ccc | tgt | gac | ttg | cag | cct | atc | ttt | gat | gac | atg | ctc | cac | ttt | cta | aat | 1824 |
|-----|-----|-----|-----|-----|-----|-----|-----|-----|-----|-----|-----|-----|-----|-----|-----|------|
| Pro | Cys | Asp | Leu | Gln | Pro | Ile | Phe | Asp | Asp | Met | Leu | His | Phe | Leu | Asn |      |
|     |     | 595 |     |     |     |     | 600 |     |     |     |     | 605 |     |     |     |      |

```
cct gag gag ctg cgg gtg att gaa gag att ccc cag gct gag gac aaa    1872
Pro Glu Glu Leu Arg Val Ile Glu Glu Ile Pro Gln Ala Glu Asp Lys
    610             615                 620 cta gac cgg cta ttc gaa att att gga gtc aag agc cag gaa gcc agc    1920
Leu Asp Arg Leu Phe Glu Ile Ile Gly Val Lys Ser Gln Glu Ala Ser
625             630                 635                 640 cag acc ctc ctg gac tct gtt tat agc cat ctt cct gac ctg ctg tag    1968
Gln Thr Leu Leu Asp Ser Val Tyr Ser His Leu Pro Asp Leu Leu
                645                 650                 655

<210> SEQ ID NO 2
<211> LENGTH: 655
<212> TYPE: PRT
<213> ORGANISM: Homo sapiens

<400> SEQUENCE: 2

Met Gly Thr Ser Pro Ser Ser Thr Ala Leu Ala Ser Cys Ser Arg
1               5                   10                  15

Ile Ala Arg Arg Ala Thr Ala Thr Met Ile Ala Gly Ser Leu Leu Leu
            20                  25                  30

Leu Gly Phe Leu Ser Thr Thr Thr Ala Gln Pro Glu Gln Lys Ala Ser
        35                  40                  45

Asn Leu Ile Gly Thr Tyr Arg His Val Asp Arg Ala Thr Gly Gln Val
    50                  55                  60

Leu Thr Cys Asp Lys Cys Pro Ala Gly Thr Tyr Val Ser Glu His Cys
65                  70                  75                  80

Thr Asn Thr Ser Leu Arg Val Cys Ser Ser Cys Pro Val Gly Thr Phe
                85                  90                  95

Thr Arg His Glu Asn Gly Ile Glu Lys Cys His Asp Cys Ser Gln Pro
            100                 105                 110

Cys Pro Trp Pro Met Ile Glu Lys Leu Pro Cys Ala Ala Leu Thr Asp
        115                 120                 125

Arg Glu Cys Thr Cys Pro Pro Gly Met Phe Gln Ser Asn Ala Thr Cys
    130                 135                 140

Ala Pro His Thr Val Cys Pro Val Gly Trp Gly Val Arg Lys Lys Gly
145                 150                 155                 160

Thr Glu Thr Glu Asp Val Arg Cys Lys Gln Cys Ala Arg Gly Thr Phe
                165                 170                 175

Ser Asp Val Pro Ser Ser Val Met Lys Cys Lys Ala Tyr Thr Asp Cys
            180                 185                 190

Leu Ser Gln Asn Leu Val Val Ile Lys Pro Gly Thr Lys Glu Thr Asp
        195                 200                 205

Asn Val Cys Gly Thr Leu Pro Ser Phe Ser Ser Ser Thr Ser Pro Ser
    210                 215                 220

Pro Gly Thr Ala Ile Phe Pro Arg Pro Glu His Met Glu Thr His Glu
225                 230                 235                 240

Val Pro Ser Ser Thr Tyr Val Pro Lys Gly Met Asn Ser Thr Glu Ser
                245                 250                 255

Asn Ser Ser Ala Ser Val Arg Pro Lys Val Leu Ser Ser Ile Gln Glu
            260                 265                 270

Gly Thr Val Pro Asp Asn Thr Ser Ser Ala Arg Gly Lys Glu Asp Val
        275                 280                 285

Asn Lys Thr Leu Pro Asn Leu Gln Val Val Asn His Gln Gln Gly Pro
    290                 295                 300

His His Arg His Ile Leu Lys Leu Leu Pro Ser Met Glu Ala Thr Gly
305                 310                 315                 320
```

Gly Glu Lys Ser Ser Thr Pro Ile Lys Gly Pro Lys Arg Gly His Pro
            325                 330                 335

Arg Gln Asn Leu His Lys His Phe Asp Ile Asn Glu His Leu Pro Trp
            340                 345                 350

Met Ile Val Leu Phe Leu Leu Leu Val Leu Val Val Ile Val Val Cys
            355                 360                 365

Ser Ile Arg Lys Ser Ser Arg Thr Leu Lys Lys Gly Pro Arg Gln Asp
        370                 375                 380

Pro Ser Ala Ile Val Glu Lys Ala Gly Leu Lys Lys Ser Met Thr Pro
385                 390                 395                 400

Thr Gln Asn Arg Glu Lys Trp Ile Tyr Tyr Cys Asn Gly His Gly Ile
                405                 410                 415

Asp Ile Leu Lys Leu Val Ala Ala Gln Val Gly Ser Gln Trp Lys Asp
            420                 425                 430

Ile Tyr Gln Phe Leu Cys Asn Ala Ser Glu Arg Glu Val Ala Ala Phe
        435                 440                 445

Ser Asn Gly Tyr Thr Ala Asp His Glu Arg Ala Tyr Ala Ala Leu Gln
    450                 455                 460

His Trp Thr Ile Arg Gly Pro Glu Ala Ser Leu Ala Gln Leu Ile Ser
465                 470                 475                 480

Ala Leu Arg Gln His Arg Arg Asn Asp Val Val Glu Lys Ile Arg Gly
                485                 490                 495

Leu Met Glu Asp Thr Thr Gln Leu Glu Thr Asp Lys Leu Ala Leu Pro
            500                 505                 510

Met Ser Pro Ser Pro Leu Ser Pro Ser Pro Ile Pro Ser Pro Asn Ala
        515                 520                 525

Lys Leu Glu Asn Ser Ala Leu Leu Thr Val Glu Pro Ser Pro Gln Asp
530                 535                 540

Lys Asn Lys Gly Phe Phe Val Asp Glu Ser Glu Pro Leu Leu Arg Cys
545                 550                 555                 560

Asp Ser Thr Ser Ser Gly Ser Ser Ala Leu Ser Arg Asn Gly Ser Phe
                565                 570                 575

Ile Thr Lys Glu Lys Lys Asp Thr Val Leu Arg Gln Val Arg Leu Asp
            580                 585                 590

Pro Cys Asp Leu Gln Pro Ile Phe Asp Asp Met Leu His Phe Leu Asn
        595                 600                 605

Pro Glu Glu Leu Arg Val Ile Glu Glu Ile Pro Gln Ala Glu Asp Lys
    610                 615                 620

Leu Asp Arg Leu Phe Glu Ile Ile Gly Val Lys Ser Gln Glu Ala Ser
625                 630                 635                 640

Gln Thr Leu Leu Asp Ser Val Tyr Ser His Leu Pro Asp Leu Leu
                645                 650                 655

<210> SEQ ID NO 3
<211> LENGTH: 1968
<212> TYPE: DNA
<213> ORGANISM: Mus musculus
<220> FEATURE:
<221> NAME/KEY: CDS
<222> LOCATION: (1)..(1968)

<400> SEQUENCE: 3 atg ggg acc cgg gca agc agc atc acc gcc ctc gcc tct tgc agc cgc      48
Met Gly Thr Arg Ala Ser Ser Ile Thr Ala Leu Ala Ser Cys Ser Arg
1               5                   10                  15

-continued

| | | |
|---|---|---|
| acc gcc ggc caa gtc gga gcc acg atg gtc gcc ggc tct ctt ctc ctg<br>Thr Ala Gly Gln Val Gly Ala Thr Met Val Ala Gly Ser Leu Leu Leu<br>20                            25                        30 | 96 |
| ctt gga ttc ctc agc acc atc aca gct caa cca gaa caa aag act ctg<br>Leu Gly Phe Leu Ser Thr Ile Thr Ala Gln Pro Glu Gln Lys Thr Leu<br>35                        40                        45 | 144 |
| agt ctc cct ggc acc tac cgc cat gtt gac cgt acc act ggc cag gtg<br>Ser Leu Pro Gly Thr Tyr Arg His Val Asp Arg Thr Thr Gly Gln Val<br>50                       55                      60 | 192 |
| cta acc tgc gac aag tgc cca gca gga acg tac gtc tcc gag cac tgt<br>Leu Thr Cys Asp Lys Cys Pro Ala Gly Thr Tyr Val Ser Glu His Cys<br>65                     70                      75                  80 | 240 |
| acc aac atg agc ctg cga gtc tgc agc agc tgc ccc gcg ggg acc ttt<br>Thr Asn Met Ser Leu Arg Val Cys Ser Ser Cys Pro Ala Gly Thr Phe<br>85                     90                        95 | 288 |
| acc agg cac gag aac ggc ata gag aga tgc cat gac tgt agt cag cca<br>Thr Arg His Glu Asn Gly Ile Glu Arg Cys His Asp Cys Ser Gln Pro<br>100                     105                   110 | 336 |
| tgt cca tgg ccg atg att gag aga tta cct tgt gct gcc ttg act gac<br>Cys Pro Trp Pro Met Ile Glu Arg Leu Pro Cys Ala Ala Leu Thr Asp<br>115                   120                   125 | 384 |
| cga gag tgc atc tgc cca cct gga atg tat cag tct aat ggt acc tgc<br>Arg Glu Cys Ile Cys Pro Pro Gly Met Tyr Gln Ser Asn Gly Thr Cys<br>130                   135                   140 | 432 |
| gct ccc cat aca gtg tgc ccc gtg ggc tgg ggt gtg cgg aag aaa ggg<br>Ala Pro His Thr Val Cys Pro Val Gly Trp Gly Val Arg Lys Lys Gly<br>145                   150                   155                   160 | 480 |
| aca gag aat gaa gat gtg cgc tgt aag cag tgc gct cgg ggt acc ttc<br>Thr Glu Asn Glu Asp Val Arg Cys Lys Gln Cys Ala Arg Gly Thr Phe<br>                   165                   170                   175 | 528 |
| tct gac gtg cct tcc agt gtg atg aag tgt aaa gct cac acg gac tgt<br>Ser Asp Val Pro Ser Ser Val Met Lys Cys Lys Ala His Thr Asp Cys<br>                   180                   185                   190 | 576 |
| ctg ggt cag aac ctg gag gtg gtc aag cca ggg acc aag gag aca gac<br>Leu Gly Gln Asn Leu Glu Val Val Lys Pro Gly Thr Lys Glu Thr Asp<br>                   195                   200                   205 | 624 |
| aac gtc tgt ggc atg cgc ctg ttc ttc tcc agc aca aac cca cct tcc<br>Asn Val Cys Gly Met Arg Leu Phe Phe Ser Ser Thr Asn Pro Pro Ser<br>210                   215                   220 | 672 |
| tct ggc aca gtt acc ttt tct cac cct gag cat atg gaa tcc cac gat<br>Ser Gly Thr Val Thr Phe Ser His Pro Glu His Met Glu Ser His Asp<br>225                   230                   235                   240 | 720 |
| gtc cct tcc tcc acc tat gag ccc caa ggc atg aac tca aca gat tcc<br>Val Pro Ser Ser Thr Tyr Glu Pro Gln Gly Met Asn Ser Thr Asp Ser<br>                   245                   250                   255 | 768 |
| aac tct act gcc tct gtt aga act aag gta cca agt ggc atc gag gaa<br>Asn Ser Thr Ala Ser Val Arg Thr Lys Val Pro Ser Gly Ile Glu Glu<br>260                   265                   270 | 816 |
| ggg aca gtg cct gac aat acg agc tca acc agt ggg aag gaa ggc act<br>Gly Thr Val Pro Asp Asn Thr Ser Ser Thr Ser Gly Lys Glu Gly Thr<br>275                   280                   285 | 864 |
| aat agg acc ctg cca aac cca cca caa gtt acc cac cag caa gcc ccc<br>Asn Arg Thr Leu Pro Asn Pro Pro Gln Val Thr His Gln Gln Ala Pro<br>290                   295                   300 | 912 |
| cac cac aga cac att ctg aag ctg ctg cca tcg tcc atg gag gcc acg<br>His His Arg His Ile Leu Lys Leu Leu Pro Ser Ser Met Glu Ala Thr<br>305                   310                   315                   320 | 960 |
| ggt gag aag tcc agc aca gcc atc aag gcc ccc aag agg ggt cac ccc<br>Gly Glu Lys Ser Ser Thr Ala Ile Lys Ala Pro Lys Arg Gly His Pro<br>                   325                   330                   335 | 1008 |

-continued

| | | |
|---|---|---|
| aga cag aac gct cac aag cat ttc gac atc aac gag cac ttg cct tgg<br>Arg Gln Asn Ala His Lys His Phe Asp Ile Asn Glu His Leu Pro Trp<br>340                             345                          350 | 1056 |
| atg atc gtc ctc ttc ctt ctg ctg gtc ctg gtg ctg ata gtg gtg tgc<br>Met Ile Val Leu Phe Leu Leu Leu Val Leu Val Leu Ile Val Val Cys<br>355                             360                          365 | 1104 |
| agt atc cga aag agc tcc agg act ctc aaa aag ggg ccc cgg cag gat<br>Ser Ile Arg Lys Ser Ser Arg Thr Leu Lys Lys Gly Pro Arg Gln Asp<br>370                             375                          380 | 1152 |
| ccc agc gcc ata gtg gaa aag gcg ggg ctg aag aag tcc ctg act ccc<br>Pro Ser Ala Ile Val Glu Lys Ala Gly Leu Lys Lys Ser Leu Thr Pro<br>385                             390                          395                          400 | 1200 |
| acc cag aac cgg gag aaa tgg atc tac tac cgc aac ggc cat ggt att<br>Thr Gln Asn Arg Glu Lys Trp Ile Tyr Tyr Arg Asn Gly His Gly Ile<br>                            405                          410                          415 | 1248 |
| gac atc ttg aag ctt gta gca gcc cag gtg gga agc cag tgg aag gac<br>Asp Ile Leu Lys Leu Val Ala Ala Gln Val Gly Ser Gln Trp Lys Asp<br>                            420                          425                          430 | 1296 |
| atc tat cag ttt ctt tgc aac gcc agc gag agg gag gtg gcg gcc ttc<br>Ile Tyr Gln Phe Leu Cys Asn Ala Ser Glu Arg Glu Val Ala Ala Phe<br>                            435                          440                          445 | 1344 |
| tcc aat gga tac act gca gat cat gaa cgg gcc tac gcg gct ctg cag<br>Ser Asn Gly Tyr Thr Ala Asp His Glu Arg Ala Tyr Ala Ala Leu Gln<br>450                             455                          460 | 1392 |
| cac tgg acc atc cgt ggc cct gag gcc agc ctt gcc cag ctc att agc<br>His Trp Thr Ile Arg Gly Pro Glu Ala Ser Leu Ala Gln Leu Ile Ser<br>465                             470                          475                          480 | 1440 |
| gcc ttg cgc cag cac cga cgc aat gat gtt gtg gag aag att cgt ggg<br>Ala Leu Arg Gln His Arg Arg Asn Asp Val Val Glu Lys Ile Arg Gly<br>                            485                          490                          495 | 1488 |
| ctg atg gaa gac acc acg cag ttg gaa aca gac aaa ctg gct ctc ccc<br>Leu Met Glu Asp Thr Thr Gln Leu Glu Thr Asp Lys Leu Ala Leu Pro<br>500                             505                          510 | 1536 |
| atg agc ccc agt ccg ctt agc ccg agc ccc atg ccc agt cct aac gtg<br>Met Ser Pro Ser Pro Leu Ser Pro Ser Pro Met Pro Ser Pro Asn Val<br>515                             520                          525 | 1584 |
| aaa ctt gag aat tcc act ctc ctg aca gtg gag ccc tca ccg ctg gac<br>Lys Leu Glu Asn Ser Thr Leu Leu Thr Val Glu Pro Ser Pro Leu Asp<br>530                             535                          540 | 1632 |
| aag aac aag tgc ttc ttc gtg gac gag tca gag ccc ctt ctg cga tgc<br>Lys Asn Lys Cys Phe Phe Val Asp Glu Ser Glu Pro Leu Leu Arg Cys<br>545                             550                          555                          560 | 1680 |
| gac tcc aca tcc agt ggc tct tca gca ctg agc aga aac ggc tcc ttt<br>Asp Ser Thr Ser Ser Gly Ser Ser Ala Leu Ser Arg Asn Gly Ser Phe<br>                            565                          570                          575 | 1728 |
| att acc aaa gaa aag aag gac aca gtg ttg cgg cag gtc cgc ctg gac<br>Ile Thr Lys Glu Lys Lys Asp Thr Val Leu Arg Gln Val Arg Leu Asp<br>580                             585                          590 | 1776 |
| ccc tgt gac ttg cag ccc atc ttt gat gac atg ctg cat atc ctg aac<br>Pro Cys Asp Leu Gln Pro Ile Phe Asp Asp Met Leu His Ile Leu Asn<br>595                             600                          605 | 1824 |
| ccc gag gag ctg cgg gtg att gaa gag att ccc cag gct gag gac aaa<br>Pro Glu Glu Leu Arg Val Ile Glu Glu Ile Pro Gln Ala Glu Asp Lys<br>610                             615                          620 | 1872 |
| ctg gac cgc ctc ttc gag atc att ggg gtc aag agc caa gaa gcc agc<br>Leu Asp Arg Leu Phe Glu Ile Ile Gly Val Lys Ser Gln Glu Ala Ser<br>625                             630                          635                          640 | 1920 |
| cag acc ctc ttg gac tct gtg tac agt cat ctt cct gac cta ttg tag<br>Gln Thr Leu Leu Asp Ser Val Tyr Ser His Leu Pro Asp Leu Leu | 1968 |

<210> SEQ ID NO 4
<211> LENGTH: 655
<212> TYPE: PRT
<213> ORGANISM: Mus musculus

<400> SEQUENCE: 4

Met Gly Thr Arg Ala Ser Ser Ile Thr Ala Leu Ala Ser Cys Ser Arg
1               5                   10                  15

Thr Ala Gly Gln Val Gly Ala Thr Met Val Ala Gly Ser Leu Leu Leu
            20                  25                  30

Leu Gly Phe Leu Ser Thr Ile Thr Ala Gln Pro Glu Lys Thr Leu
        35                  40                  45

Ser Leu Pro Gly Thr Tyr Arg His Val Asp Arg Thr Thr Gly Gln Val
50                  55                  60

Leu Thr Cys Asp Lys Cys Pro Ala Gly Thr Tyr Val Ser Glu His Cys
65                  70                  75                  80

Thr Asn Met Ser Leu Arg Val Cys Ser Ser Cys Pro Ala Gly Thr Phe
                85                  90                  95

Thr Arg His Glu Asn Gly Ile Glu Arg Cys His Asp Cys Ser Gln Pro
            100                 105                 110

Cys Pro Trp Pro Met Ile Glu Arg Leu Pro Cys Ala Ala Leu Thr Asp
        115                 120                 125

Arg Glu Cys Ile Cys Pro Pro Gly Met Tyr Gln Ser Asn Gly Thr Cys
130                 135                 140

Ala Pro His Thr Val Cys Pro Val Gly Trp Gly Val Arg Lys Lys Gly
145                 150                 155                 160

Thr Glu Asn Glu Asp Val Arg Cys Lys Gln Cys Ala Arg Gly Thr Phe
                165                 170                 175

Ser Asp Val Pro Ser Ser Val Met Lys Cys Lys Ala His Thr Asp Cys
            180                 185                 190

Leu Gly Gln Asn Leu Glu Val Val Lys Pro Gly Thr Lys Glu Thr Asp
        195                 200                 205

Asn Val Cys Gly Met Arg Leu Phe Phe Ser Ser Thr Asn Pro Pro Ser
210                 215                 220

Ser Gly Thr Val Thr Phe Ser His Pro Glu His Met Glu Ser His Asp
225                 230                 235                 240

Val Pro Ser Ser Thr Tyr Glu Pro Gln Gly Met Asn Ser Thr Asp Ser
                245                 250                 255

Asn Ser Thr Ala Ser Val Arg Thr Lys Val Pro Ser Gly Ile Glu Glu
            260                 265                 270

Gly Thr Val Pro Asp Asn Thr Ser Ser Thr Ser Gly Lys Glu Gly Thr
        275                 280                 285

Asn Arg Thr Leu Pro Asn Pro Gln Val Thr His Gln Gln Ala Pro
290                 295                 300

His His Arg His Ile Leu Lys Leu Leu Pro Ser Ser Met Glu Ala Thr
305                 310                 315                 320

Gly Glu Lys Ser Ser Thr Ala Ile Lys Ala Pro Lys Arg Gly His Pro
                325                 330                 335

Arg Gln Asn Ala His Lys His Phe Asp Ile Asn Glu His Leu Pro Trp
            340                 345                 350

Met Ile Val Leu Phe Leu Leu Leu Val Leu Val Leu Ile Val Val Cys
        355                 360                 365

-continued

```
Ser Ile Arg Lys Ser Ser Arg Thr Leu Lys Lys Gly Pro Arg Gln Asp
    370                 375                 380

Pro Ser Ala Ile Val Glu Lys Ala Gly Leu Lys Lys Ser Leu Thr Pro
385                 390                 395                 400

Thr Gln Asn Arg Glu Lys Trp Ile Tyr Tyr Arg Asn Gly His Gly Ile
                405                 410                 415

Asp Ile Leu Lys Leu Val Ala Ala Gln Val Gly Ser Gln Trp Lys Asp
            420                 425                 430

Ile Tyr Gln Phe Leu Cys Asn Ala Ser Glu Arg Glu Val Ala Ala Phe
        435                 440                 445

Ser Asn Gly Tyr Thr Ala Asp His Glu Arg Ala Tyr Ala Ala Leu Gln
450                 455                 460

His Trp Thr Ile Arg Gly Pro Glu Ala Ser Leu Ala Gln Leu Ile Ser
465                 470                 475                 480

Ala Leu Arg Gln His Arg Arg Asn Asp Val Val Glu Lys Ile Arg Gly
                485                 490                 495

Leu Met Glu Asp Thr Thr Gln Leu Glu Thr Asp Lys Leu Ala Leu Pro
            500                 505                 510

Met Ser Pro Ser Pro Leu Ser Pro Ser Pro Met Pro Ser Pro Asn Val
        515                 520                 525

Lys Leu Glu Asn Ser Thr Leu Leu Thr Val Glu Pro Ser Pro Leu Asp
530                 535                 540

Lys Asn Lys Cys Phe Phe Val Asp Glu Ser Glu Pro Leu Leu Arg Cys
545                 550                 555                 560

Asp Ser Thr Ser Ser Gly Ser Ser Ala Leu Ser Arg Asn Gly Ser Phe
                565                 570                 575

Ile Thr Lys Glu Lys Lys Asp Thr Val Leu Arg Gln Val Arg Leu Asp
            580                 585                 590

Pro Cys Asp Leu Gln Pro Ile Phe Asp Asp Met Leu His Ile Leu Asn
        595                 600                 605

Pro Glu Glu Leu Arg Val Ile Glu Glu Ile Pro Gln Ala Glu Asp Lys
610                 615                 620

Leu Asp Arg Leu Phe Glu Ile Ile Gly Val Lys Ser Gln Glu Ala Ser
625                 630                 635                 640

Gln Thr Leu Leu Asp Ser Val Tyr Ser His Leu Pro Asp Leu Leu
                645                 650                 655

<210> SEQ ID NO 5
<211> LENGTH: 933
<212> TYPE: DNA
<213> ORGANISM: Homo sapiens
<220> FEATURE:
<221> NAME/KEY: CDS
<222> LOCATION: (1)..(933)

<400> SEQUENCE: 5 atg agg cgc gcg gcg ctc tgg ctc tgg ctg tgc gcg ctg gcg ctg agc      48
Met Arg Arg Ala Ala Leu Trp Leu Trp Leu Cys Ala Leu Ala Leu Ser
1               5                   10                  15 ctg cag ccg gcc ctg ccg caa att gtg gct act aat ttg ccc cct gaa      96
Leu Gln Pro Ala Leu Pro Gln Ile Val Ala Thr Asn Leu Pro Pro Glu
            20                  25                  30 gat caa gat ggc tct ggg gat gac tct gac aac ttc tcc ggc tca ggt     144
Asp Gln Asp Gly Ser Gly Asp Asp Ser Asp Asn Phe Ser Gly Ser Gly
        35                  40                  45 gca ggt gct ttg caa gat atc acc ttg tca cag cag acc ccc tcc act     192
Ala Gly Ala Leu Gln Asp Ile Thr Leu Ser Gln Gln Thr Pro Ser Thr
```

```
          50                  55                  60
tgg aag gac acg cag ctc ctg acg gct att ccc acg tct cca gaa ccc      240
Trp Lys Asp Thr Gln Leu Leu Thr Ala Ile Pro Thr Ser Pro Glu Pro
 65                  70                  75                  80 acc ggc ctg gag gct aca gct gcc tcc acc tcc acc ctg ccg gct gga      288
Thr Gly Leu Glu Ala Thr Ala Ala Ser Thr Ser Thr Leu Pro Ala Gly
                 85                  90                  95 gag ggg ccc aag gag gga gag gct gta gtc ctg cca gaa gtg gag cct      336
Glu Gly Pro Lys Glu Gly Glu Ala Val Val Leu Pro Glu Val Glu Pro
            100                 105                 110 ggc ctc acc gcc cgg gag cag gag gcc acc ccc cga ccc agg gag acc      384
Gly Leu Thr Ala Arg Glu Gln Glu Ala Thr Pro Arg Pro Arg Glu Thr
        115                 120                 125 aca cag ctc ccg acc act cat cag gcc tca acg acc aca gcc acc acg      432
Thr Gln Leu Pro Thr Thr His Gln Ala Ser Thr Thr Thr Ala Thr Thr
130                 135                 140 gcc cag gag ccc gcc acc tcc cac ccc cac agg gac atg cag cct ggc      480
Ala Gln Glu Pro Ala Thr Ser His Pro His Arg Asp Met Gln Pro Gly
145                 150                 155                 160 cac cat gag acc tca acc cct gca gga ccc agc caa gct gac ctt cac      528
His His Glu Thr Ser Thr Pro Ala Gly Pro Ser Gln Ala Asp Leu His
                165                 170                 175 act ccc cac aca gag gat gga ggt cct tct gcc acc gag agg gct gct      576
Thr Pro His Thr Glu Asp Gly Gly Pro Ser Ala Thr Glu Arg Ala Ala
            180                 185                 190 gag gat gga gcc tcc agt cag ctc cca gca gca gag ggc tct ggg gag      624
Glu Asp Gly Ala Ser Ser Gln Leu Pro Ala Ala Glu Gly Ser Gly Glu
        195                 200                 205 cag gac ttc acc ttt gaa acc tcg ggg gag aat acg gct gta gtg gcc      672
Gln Asp Phe Thr Phe Glu Thr Ser Gly Glu Asn Thr Ala Val Val Ala
    210                 215                 220 gtg gag cct gac cgc cgg aac cag tcc cca gtg gat cag ggg gcc acg      720
Val Glu Pro Asp Arg Arg Asn Gln Ser Pro Val Asp Gln Gly Ala Thr
225                 230                 235                 240 ggg gcc tca cag ggc ctc ctg gac agg aaa gag gtg ctg gga ggg gtc      768
Gly Ala Ser Gln Gly Leu Leu Asp Arg Lys Glu Val Leu Gly Gly Val
                245                 250                 255 att gcc gga ggc ctc gtg ggg ctc atc ttt gct gtg tgc ctg gtg ggt      816
Ile Ala Gly Gly Leu Val Gly Leu Ile Phe Ala Val Cys Leu Val Gly
            260                 265                 270 ttc atg ctg tac cgc atg aag aag aag gac gaa ggc agc tac tcc ttg      864
Phe Met Leu Tyr Arg Met Lys Lys Lys Asp Glu Gly Ser Tyr Ser Leu
        275                 280                 285 gag gag ccg aaa caa gcc aac ggc ggg gcc tac cag aag ccc acc aaa      912
Glu Glu Pro Lys Gln Ala Asn Gly Gly Ala Tyr Gln Lys Pro Thr Lys
    290                 295                 300 cag gag gaa ttc tat gcc tga                                          933
Gln Glu Glu Phe Tyr Ala
305                 310

<210> SEQ ID NO 6
<211> LENGTH: 310
<212> TYPE: PRT
<213> ORGANISM: Homo sapiens

<400> SEQUENCE: 6

Met Arg Arg Ala Ala Leu Trp Leu Trp Leu Cys Ala Leu Ala Leu Ser
 1               5                  10                  15

Leu Gln Pro Ala Leu Pro Gln Ile Val Ala Thr Asn Leu Pro Pro Glu
            20                  25                  30
```

```
Asp Gln Asp Gly Ser Gly Asp Ser Asp Asn Phe Ser Gly Ser Gly
         35                  40                  45

Ala Gly Ala Leu Gln Asp Ile Thr Leu Ser Gln Gln Thr Pro Ser Thr
 50                  55                  60

Trp Lys Asp Thr Gln Leu Leu Thr Ala Ile Pro Thr Ser Pro Glu Pro
 65                  70                  75                  80

Thr Gly Leu Glu Ala Thr Ala Ala Ser Thr Ser Thr Leu Pro Ala Gly
                 85                  90                  95

Glu Gly Pro Lys Glu Gly Glu Ala Val Val Leu Pro Glu Val Glu Pro
            100                 105                 110

Gly Leu Thr Ala Arg Glu Gln Ala Thr Pro Arg Pro Arg Glu Thr
        115                 120                 125

Thr Gln Leu Pro Thr Thr His Gln Ala Ser Thr Thr Ala Thr Thr
130                 135                 140

Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
                165                 170                 175

Thr Pro His Thr Glu Asp Gly Gly Pro Ser Ala Thr Glu Arg Ala Ala
            180                 185                 190

Glu Asp Gly Ala Ser Ser Gln Leu Pro Ala Ala Glu Gly Ser Gly Glu
        195                 200                 205

Gln Asp Phe Thr Phe Glu Thr Ser Gly Glu Asn Thr Ala Val Val Ala
210                 215                 220

Val Glu Pro Asp Arg Arg Asn Gln Ser Pro Val Asp Gln Gly Ala Thr
225                 230                 235                 240

Gly Ala Ser Gln Gly Leu Leu Asp Arg Lys Glu Val Leu Gly Gly Val
                245                 250                 255

Ile Ala Gly Gly Leu Val Gly Leu Ile Phe Ala Val Cys Leu Val Gly
            260                 265                 270

Phe Met Leu Tyr Arg Met Lys Lys Lys Asp Glu Gly Ser Tyr Ser Leu
        275                 280                 285

Glu Glu Pro Lys Gln Ala Asn Gly Gly Ala Tyr Gln Lys Pro Thr Lys
    290                 295                 300

Gln Glu Glu Phe Tyr Ala
305                 310

<210> SEQ ID NO 7
<211> LENGTH: 936
<212> TYPE: DNA
<213> ORGANISM: Mus musculus
<220> FEATURE:
<221> NAME/KEY: CDS
<222> LOCATION: (1)..(936)

<400> SEQUENCE: 7 atg aga cgc gcg gcg ctc tgg ctc tgg ctc tgc gcg ctg gcg ctg cgc      48
Met Arg Arg Ala Ala Leu Trp Leu Trp Leu Cys Ala Leu Ala Leu Arg
 1               5                  10                  15 ctg cag cct gcc ctc ccg caa att gtg gct gta aat gtt cct cct gaa      96
Leu Gln Pro Ala Leu Pro Gln Ile Val Ala Val Asn Val Pro Pro Glu
             20                  25                  30 gat cag gat ggc tct ggg gat gac tct gac aac ttc tct ggc tct ggc     144
Asp Gln Asp Gly Ser Gly Asp Asp Ser Asp Asn Phe Ser Gly Ser Gly
         35                  40                  45 aca ggt gct ttg cca gat act ttg tca cgg cag aca cct tcc act tgg     192
```

| | | | | | | | | | | | | |
|---|---|---|---|---|---|---|---|---|---|---|---|---|
| Thr | Gly | Ala | Leu | Pro | Asp | Thr | Leu | Ser | Arg | Gln | Thr | Pro | Ser | Thr | Trp |
| | 50 | | | | 55 | | | | 60 | | | | |

```
aag gac gtg tgg ctg ttg aca gcc acg ccc aca gct cca gag ccc acc      240
Lys Asp Val Trp Leu Leu Thr Ala Thr Pro Thr Ala Pro Glu Pro Thr
 65              70                  75                  80 agc agc aac acc gag act gct ttt acc tct gtc ctg cca gcc gga gag      288
Ser Ser Asn Thr Glu Thr Ala Phe Thr Ser Val Leu Pro Ala Gly Glu
                 85                  90                  95 aag ccc gag gag gga gag cct gtg ctc cat gta gaa gca gag cct ggc      336
Lys Pro Glu Glu Gly Glu Pro Val Leu His Val Glu Ala Glu Pro Gly
            100                 105                 110 ttc act gct cgg gac aag gaa aag gag gtc acc acc agg ccc agg gag      384
Phe Thr Ala Arg Asp Lys Glu Lys Glu Val Thr Thr Arg Pro Arg Glu
        115                 120                 125 acc gtg cag ctc ccc atc acc caa cgg gcc tca aca gtc aga gtc acc      432
Thr Val Gln Leu Pro Ile Thr Gln Arg Ala Ser Thr Val Arg Val Thr
    130                 135                 140 aca gcc cag gca gct gtc aca tct cat ccg cac ggg ggc atg caa cct      480
Thr Ala Gln Ala Ala Val Thr Ser His Pro His Gly Gly Met Gln Pro
145                 150                 155                 160 ggc ctc cat gag acc tcg gct ccc aca gca cct ggt caa cct gac cat      528
Gly Leu His Glu Thr Ser Ala Pro Thr Ala Pro Gly Gln Pro Asp His
                165                 170                 175 cag cct cca cgt gtg gag ggt ggc ggc act tct gtc atc aaa gag gtt      576
Gln Pro Pro Arg Val Glu Gly Gly Gly Thr Ser Val Ile Lys Glu Val
            180                 185                 190 gtc gag gat gga act gcc aat cag ctt ccc gca gga gag ggc tct gga      624
Val Glu Asp Gly Thr Ala Asn Gln Leu Pro Ala Gly Glu Gly Ser Gly
        195                 200                 205 gaa caa gac ttc acc ttt gaa aca tct ggg gag aac aca gct gtg gct      672
Glu Gln Asp Phe Thr Phe Glu Thr Ser Gly Glu Asn Thr Ala Val Ala
    210                 215                 220 gcc gta gag ccc ggc ctg cgg aat cag ccc ccg gtg gac gaa gga gcc      720
Ala Val Glu Pro Gly Leu Arg Asn Gln Pro Pro Val Asp Glu Gly Ala
225                 230                 235                 240 aca ggt gct tct cag agc ctt ttg gac agg aag gaa gtg ctg gga ggt      768
Thr Gly Ala Ser Gln Ser Leu Leu Asp Arg Lys Glu Val Leu Gly Gly
                245                 250                 255 gtc att gcc gga ggc cta gtg ggc ctc atc ttt gct gtg tgc ctg gtg      816
Val Ile Ala Gly Gly Leu Val Gly Leu Ile Phe Ala Val Cys Leu Val
            260                 265                 270 gct ttc atg ctg tac cgg atg aag aag aag gac gaa ggc agc tac tcc      864
Ala Phe Met Leu Tyr Arg Met Lys Lys Lys Asp Glu Gly Ser Tyr Ser
        275                 280                 285 ttg gag gag ccc aaa caa gcc aat ggc ggt gcc tac cag aaa ccc acc      912
Leu Glu Glu Pro Lys Gln Ala Asn Gly Gly Ala Tyr Gln Lys Pro Thr
    290                 295                 300 aag cag gag gag ttc tac gcc tga                                       936
Lys Gln Glu Glu Phe Tyr Ala
305                 310
```

<210> SEQ ID NO 8
<211> LENGTH: 311
<212> TYPE: PRT
<213> ORGANISM: Mus musculus

<400> SEQUENCE: 8

```
Met Arg Arg Ala Ala Leu Trp Leu Trp Leu Cys Ala Leu Ala Leu Arg
  1               5                  10                  15

Leu Gln Pro Ala Leu Pro Gln Ile Val Ala Val Asn Val Pro Pro Glu
```

20                  25                  30

Asp Gln Asp Gly Ser Gly Asp Asp Ser Asp Asn Phe Ser Gly Ser Gly
            35                  40                  45

Thr Gly Ala Leu Pro Asp Thr Leu Ser Arg Gln Thr Pro Ser Thr Trp
    50                  55                  60

Lys Asp Val Trp Leu Leu Thr Ala Thr Pro Thr Ala Pro Glu Pro Thr
65                  70                  75                  80

Ser Ser Asn Thr Glu Thr Ala Phe Thr Ser Val Leu Pro Ala Gly Glu
                85                  90                  95

Lys Pro Glu Glu Gly Glu Pro Val Leu His Val Glu Ala Glu Pro Gly
            100                 105                 110

Phe Thr Ala Arg Asp Lys Glu Lys Glu Val Thr Thr Arg Pro Arg Glu
        115                 120                 125

Thr Val Gln Leu Pro Ile Thr Gln Arg Ala Ser Thr Val Arg Val Thr
    130                 135                 140

Thr Ala Gln Ala Ala Val Thr Ser His Pro His Gly Gly Met Gln Pro
145                 150                 155                 160

Gly Leu His Glu Thr Ser Ala Pro Thr Ala Pro Gly Gln Pro Asp His
                165                 170                 175

Gln Pro Pro Arg Val Glu Gly Gly Thr Ser Val Ile Lys Glu Val
            180                 185                 190

Val Glu Asp Gly Thr Ala Asn Gln Leu Pro Ala Gly Glu Gly Ser Gly
        195                 200                 205

Glu Gln Asp Phe Thr Phe Glu Thr Ser Gly Glu Asn Thr Ala Val Ala
    210                 215                 220

Ala Val Glu Pro Gly Leu Arg Asn Gln Pro Pro Val Asp Glu Gly Ala
225                 230                 235                 240

Thr Gly Ala Ser Gln Ser Leu Leu Asp Arg Lys Glu Val Leu Gly Gly
                245                 250                 255

Val Ile Ala Gly Gly Leu Val Gly Leu Ile Phe Ala Val Cys Leu Val
            260                 265                 270

Ala Phe Met Leu Tyr Arg Met Lys Lys Lys Asp Glu Gly Ser Tyr Ser
        275                 280                 285

Leu Glu Glu Pro Lys Gln Ala Asn Gly Gly Ala Tyr Gln Lys Pro Thr
    290                 295                 300

Lys Gln Glu Glu Phe Tyr Ala
305                 310

<210> SEQ ID NO 9
<211> LENGTH: 750
<212> TYPE: DNA
<213> ORGANISM: Homo sapiens
<220> FEATURE:
<221> NAME/KEY: CDS
<222> LOCATION: (1)..(750)

<400> SEQUENCE: 9 atg agg cgc gcg gcg ctc tgg ctc tgg ctg tgc gcg ctg gcg ctg agc    48
Met Arg Arg Ala Ala Leu Trp Leu Trp Leu Cys Ala Leu Ala Leu Ser
1               5                   10                  15 ctg cag ccg gcc ctg ccg caa att gtg gct act aat ttg ccc cct gaa    96
Leu Gln Pro Ala Leu Pro Gln Ile Val Ala Thr Asn Leu Pro Pro Glu
            20                  25                  30 gat caa gat ggc tct ggg gat gac tct gac aac ttc tcc ggc tca ggt   144
Asp Gln Asp Gly Ser Gly Asp Asp Ser Asp Asn Phe Ser Gly Ser Gly
        35                  40                  45

```
gca ggt gct ttg caa gat atc acc ttg tca cag cag acc ccc tcc act    192
Ala Gly Ala Leu Gln Asp Ile Thr Leu Ser Gln Gln Thr Pro Ser Thr
 50                  55                  60 tgg aag gac acg cag ctc ctg acg gct att ccc acg tct cca gaa ccc    240
Trp Lys Asp Thr Gln Leu Leu Thr Ala Ile Pro Thr Ser Pro Glu Pro
 65                  70                  75                  80 acc ggc ctg gag gct aca gct gcc tcc acc tcc acc ctg ccg gct gga    288
Thr Gly Leu Glu Ala Thr Ala Ala Ser Thr Ser Thr Leu Pro Ala Gly
                 85                  90                  95 gag ggg ccc aag gag gga gag gct gta gtc ctg cca gaa gtg gag cct    336
Glu Gly Pro Lys Glu Gly Glu Ala Val Val Leu Pro Glu Val Glu Pro
                100                 105                 110 ggc ctc acc gcc cgg gag cag gag gcc acc ccc cga ccc agg gag acc    384
Gly Leu Thr Ala Arg Glu Gln Glu Ala Thr Pro Arg Pro Arg Glu Thr
                115                 120                 125 aca cag ctc ccg acc act cat cag gcc tca acg acc aca gcc acc acg    432
Thr Gln Leu Pro Thr Thr His Gln Ala Ser Thr Thr Thr Ala Thr Thr
130                 135                 140 gcc cag gag ccc gcc acc tcc cac ccc cac agg gac atg cag cct ggc    480
Ala Gln Glu Pro Ala Thr Ser His Pro His Arg Asp Met Gln Pro Gly
145                 150                 155                 160 cac cat gag acc tca acc cct gca gga ccc agc caa gct gac ctt cac    528
His His Glu Thr Ser Thr Pro Ala Gly Pro Ser Gln Ala Asp Leu His
                165                 170                 175 act ccc cac aca gag gat gga ggt cct tct gcc acc gag agg gct gct    576
Thr Pro His Thr Glu Asp Gly Gly Pro Ser Ala Thr Glu Arg Ala Ala
                180                 185                 190 gag gat gga gcc tcc agt cag ctc cca gca gca gag ggc tct ggg gag    624
Glu Asp Gly Ala Ser Ser Gln Leu Pro Ala Ala Glu Gly Ser Gly Glu
                195                 200                 205 cag gac ttc acc ttt gaa acc tcg ggg gag aat acg gct gta gtg gcc    672
Gln Asp Phe Thr Phe Glu Thr Ser Gly Glu Asn Thr Ala Val Val Ala
                210                 215                 220 gtg gag cct gac cgc cgg aac cag tcc cca gtg gat cag ggg gcc acg    720
Val Glu Pro Asp Arg Arg Asn Gln Ser Pro Val Asp Gln Gly Ala Thr
225                 230                 235                 240 ggg gcc tca cag ggc ctc ctg gac agg aaa                            750
Gly Ala Ser Gln Gly Leu Leu Asp Arg Lys
                245                 250

<210> SEQ ID NO 10
<211> LENGTH: 250
<212> TYPE: PRT
<213> ORGANISM: Homo sapiens

<400> SEQUENCE: 10

Met Arg Arg Ala Ala Leu Trp Leu Trp Leu Cys Ala Leu Ala Leu Ser
1               5                   10                  15

Leu Gln Pro Ala Leu Pro Gln Ile Val Ala Thr Asn Leu Pro Pro Glu
            20                  25                  30

Asp Gln Asp Gly Ser Gly Asp Asp Ser Asp Asn Phe Ser Gly Ser Gly
        35                  40                  45

Ala Gly Ala Leu Gln Asp Ile Thr Leu Ser Gln Gln Thr Pro Ser Thr
 50                  55                  60

Trp Lys Asp Thr Gln Leu Leu Thr Ala Ile Pro Thr Ser Pro Glu Pro
 65                  70                  75                  80

Thr Gly Leu Glu Ala Thr Ala Ala Ser Thr Ser Thr Leu Pro Ala Gly
                 85                  90                  95

Glu Gly Pro Lys Glu Gly Glu Ala Val Val Leu Pro Glu Val Glu Pro
```

```
            100                 105                 110
Gly Leu Thr Ala Arg Glu Gln Glu Ala Thr Pro Arg Pro Arg Glu Thr
        115                 120                 125

Thr Gln Leu Pro Thr Thr His Gln Ala Ser Thr Thr Ala Thr Thr
    130                 135                 140

Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
                165                 170                 175

Thr Pro His Thr Glu Asp Gly Gly Pro Ser Ala Thr Glu Arg Ala Ala
            180                 185                 190

Glu Asp Gly Ala Ser Ser Gln Leu Pro Ala Ala Glu Gly Ser Gly Glu
        195                 200                 205

Gln Asp Phe Thr Phe Glu Thr Ser Gly Glu Asn Thr Ala Val Val Ala
    210                 215                 220

Val Glu Pro Asp Arg Arg Asn Gln Ser Pro Val Asp Gln Gly Ala Thr
225                 230                 235                 240

Gly Ala Ser Gln Gly Leu Leu Asp Arg Lys
                245                 250

<210> SEQ ID NO 11
<211> LENGTH: 753
<212> TYPE: DNA
<213> ORGANISM: Mus musculus
<220> FEATURE:
<221> NAME/KEY: CDS
<222> LOCATION: (1)..(753)

<400> SEQUENCE: 11 atg aga cgc gcg gcg ctc tgg ctc tgg ctc tgc gcg ctg gcg ctg cgc    48
Met Arg Arg Ala Ala Leu Trp Leu Trp Leu Cys Ala Leu Ala Leu Arg
1               5                   10                  15 ctg cag cct gcc ctc ccg caa att gtg gct gta aat gtt cct cct gaa    96
Leu Gln Pro Ala Leu Pro Gln Ile Val Ala Val Asn Val Pro Pro Glu
            20                  25                  30 gat cag gat ggc tct ggg gat gac tct gac aac ttc tct ggc tct ggc   144
Asp Gln Asp Gly Ser Gly Asp Asp Ser Asp Asn Phe Ser Gly Ser Gly
        35                  40                  45 aca ggt gct ttg cca gat act ttg tca cgg cag aca cct tcc act tgg   192
Thr Gly Ala Leu Pro Asp Thr Leu Ser Arg Gln Thr Pro Ser Thr Trp
    50                  55                  60 aag gac gtg tgg ctg ttg aca gcc acg ccc aca gct cca gag ccc acc   240
Lys Asp Val Trp Leu Leu Thr Ala Thr Pro Thr Ala Pro Glu Pro Thr
65                  70                  75                  80 agc agc aac acc gag act gct ttt acc tct gtc ctg cca gcc gga gag   288
Ser Ser Asn Thr Glu Thr Ala Phe Thr Ser Val Leu Pro Ala Gly Glu
                85                  90                  95 aag ccc gag gag gga gag cct gtg ctc cat gta gaa gca gag cct ggc   336
Lys Pro Glu Glu Gly Glu Pro Val Leu His Val Glu Ala Glu Pro Gly
            100                 105                 110 ttc act gct cgg gac aag gaa aag gag gtc acc acc agg ccc agg gag   384
Phe Thr Ala Arg Asp Lys Glu Lys Glu Val Thr Thr Arg Pro Arg Glu
        115                 120                 125 acc gtg cag ctc ccc atc acc caa cgg gcc tca aca gtc aga gtc acc   432
Thr Val Gln Leu Pro Ile Thr Gln Arg Ala Ser Thr Val Arg Val Thr
    130                 135                 140 aca gcc cag gca gct gtc aca tct cat ccg cac ggg ggc atg caa cct   480
Thr Ala Gln Ala Ala Val Thr Ser His Pro His Gly Gly Met Gln Pro
145                 150                 155                 160
```

```
ggc ctc cat gag acc tcg gct ccc aca gca cct ggt caa cct gac cat        528
Gly Leu His Glu Thr Ser Ala Pro Thr Ala Pro Gly Gln Pro Asp His
            165                 170                 175 cag cct cca cgt gtg gag ggt ggc ggc act tct gtc atc aaa gag gtt        576
Gln Pro Pro Arg Val Glu Gly Gly Gly Thr Ser Val Ile Lys Glu Val
        180                 185                 190 gtc gag gat gga act gcc aat cag ctt ccc gca gga gag ggc tct gga        624
Val Glu Asp Gly Thr Ala Asn Gln Leu Pro Ala Gly Glu Gly Ser Gly
    195                 200                 205 gaa caa gac ttc acc ttt gaa aca tct ggg gag aac aca gct gtg gct        672
Glu Gln Asp Phe Thr Phe Glu Thr Ser Gly Glu Asn Thr Ala Val Ala
210                 215                 220 gcc gta gag ccc ggc ctg cgg aat cag ccc ccg gtg gac gaa gga gcc        720
Ala Val Glu Pro Gly Leu Arg Asn Gln Pro Pro Val Asp Glu Gly Ala
225                 230                 235                 240 aca ggt gct tct cag agc ctt ttg gac agg aag                            753
Thr Gly Ala Ser Gln Ser Leu Leu Asp Arg Lys
                245                 250

<210> SEQ ID NO 12
<211> LENGTH: 251
<212> TYPE: PRT
<213> ORGANISM: Mus musculus

<400> SEQUENCE: 12

Met Arg Arg Ala Ala Leu Trp Leu Trp Leu Cys Ala Leu Ala Leu Arg
1               5                   10                  15

Leu Gln Pro Ala Leu Pro Gln Ile Val Ala Val Asn Val Pro Pro Glu
            20                  25                  30

Asp Gln Asp Gly Ser Gly Asp Asp Ser Asp Asn Phe Ser Gly Ser Gly
        35                  40                  45

Thr Gly Ala Leu Pro Asp Thr Leu Ser Arg Gln Thr Pro Ser Thr Trp
    50                  55                  60

Lys Asp Val Trp Leu Leu Thr Ala Thr Pro Thr Ala Pro Glu Pro Thr
65                  70                  75                  80

Ser Ser Asn Thr Glu Thr Ala Phe Thr Ser Val Leu Pro Ala Gly Glu
                85                  90                  95

Lys Pro Glu Glu Gly Glu Pro Val Leu His Val Glu Ala Glu Pro Gly
            100                 105                 110

Phe Thr Ala Arg Asp Lys Glu Lys Glu Val Thr Thr Arg Pro Arg Glu
        115                 120                 125

Thr Val Gln Leu Pro Ile Thr Gln Arg Ala Ser Thr Val Arg Val Thr
    130                 135                 140

Thr Ala Gln Ala Ala Val Thr Ser His Pro His Gly Gly Met Gln Pro
145                 150                 155                 160

Gly Leu His Glu Thr Ser Ala Pro Thr Ala Pro Gly Gln Pro Asp His
                165                 170                 175

Gln Pro Pro Arg Val Glu Gly Gly Gly Thr Ser Val Ile Lys Glu Val
            180                 185                 190

Val Glu Asp Gly Thr Ala Asn Gln Leu Pro Ala Gly Glu Gly Ser Gly
        195                 200                 205

Glu Gln Asp Phe Thr Phe Glu Thr Ser Gly Glu Asn Thr Ala Val Ala
    210                 215                 220

Ala Val Glu Pro Gly Leu Arg Asn Gln Pro Pro Val Asp Glu Gly Ala
225                 230                 235                 240

Thr Gly Ala Ser Gln Ser Leu Leu Asp Arg Lys
```

<210> SEQ ID NO 13
<211> LENGTH: 24
<212> TYPE: DNA
<213> ORGANISM: Rattus norvegicus
<220> FEATURE:
<221> NAME/KEY: CDS
<222> LOCATION: (1)..(24)

<400> SEQUENCE: 13 gga ttc act ttc agt aac tat tac                                     24
Gly Phe Thr Phe Ser Asn Tyr Tyr
1               5

<210> SEQ ID NO 14
<211> LENGTH: 8
<212> TYPE: PRT
<213> ORGANISM: Rattus norvegicus

<400> SEQUENCE: 14

Gly Phe Thr Phe Ser Asn Tyr Tyr
1               5

<210> SEQ ID NO 15
<211> LENGTH: 24
<212> TYPE: DNA
<213> ORGANISM: Rattus norvegicus
<220> FEATURE:
<221> NAME/KEY: CDS
<222> LOCATION: (1)..(24)

<400> SEQUENCE: 15 att agt aat ggt ggt ggt aac act                                     24
Ile Ser Asn Gly Gly Gly Asn Thr
1               5

<210> SEQ ID NO 16
<211> LENGTH: 8
<212> TYPE: PRT
<213> ORGANISM: Rattus norvegicus

<400> SEQUENCE: 16

Ile Ser Asn Gly Gly Gly Asn Thr
1               5

<210> SEQ ID NO 17
<211> LENGTH: 42
<212> TYPE: DNA
<213> ORGANISM: Rattus norvegicus
<220> FEATURE:
<221> NAME/KEY: CDS
<222> LOCATION: (1)..(42)

<400> SEQUENCE: 17 gca aga cag gac tac ccg gct ata acc ggg gtt atg gaa gcc             42
Ala Arg Gln Asp Tyr Pro Ala Ile Thr Gly Val Met Glu Ala
1               5                   10

<210> SEQ ID NO 18
<211> LENGTH: 14
<212> TYPE: PRT
<213> ORGANISM: Rattus norvegicus

<400> SEQUENCE: 18

Ala Arg Gln Asp Tyr Pro Ala Ile Thr Gly Val Met Glu Ala
1               5                   10

<210> SEQ ID NO 19
<211> LENGTH: 36
<212> TYPE: DNA
<213> ORGANISM: Rattus norvegicus
<220> FEATURE:
<221> NAME/KEY: CDS
<222> LOCATION: (1)..(36)

<400> SEQUENCE: 19 cag agt ctt tta tac agt gga aac caa aag aac tac                36
Gln Ser Leu Leu Tyr Ser Gly Asn Gln Lys Asn Tyr
1               5                   10

<210> SEQ ID NO 20
<211> LENGTH: 12
<212> TYPE: PRT
<213> ORGANISM: Rattus norvegicus

<400> SEQUENCE: 20

Gln Ser Leu Leu Tyr Ser Gly Asn Gln Lys Asn Tyr
1               5                   10

<210> SEQ ID NO 21
<211> LENGTH: 27
<212> TYPE: DNA
<213> ORGANISM: Rattus norvegicus
<220> FEATURE:
<221> NAME/KEY: CDS
<222> LOCATION: (1)..(27)

<400> SEQUENCE: 21 cag caa tat tat gat act cca ttc acg                             27
Gln Gln Tyr Tyr Asp Thr Pro Phe Thr
1               5

<210> SEQ ID NO 22
<211> LENGTH: 9
<212> TYPE: PRT
<213> ORGANISM: Rattus norvegicus

<400> SEQUENCE: 22

Gln Gln Tyr Tyr Asp Thr Pro Phe Thr
1               5

<210> SEQ ID NO 23
<211> LENGTH: 24
<212> TYPE: DNA
<213> ORGANISM: Rattus norvegicus
<220> FEATURE:
<221> NAME/KEY: CDS
<222> LOCATION: (1)..(24)

<400> SEQUENCE: 23 gga ttc aca ttc aat aac tac tgg                                 24
Gly Phe Thr Phe Asn Asn Tyr Trp
1               5

<210> SEQ ID NO 24
<211> LENGTH: 8
<212> TYPE: PRT
<213> ORGANISM: Rattus norvegicus

<400> SEQUENCE: 24

Gly Phe Thr Phe Asn Asn Tyr Trp
1               5

<210> SEQ ID NO 25
<211> LENGTH: 24
<212> TYPE: DNA
<213> ORGANISM: Rattus norvegicus
<220> FEATURE:
<221> NAME/KEY: CDS
<222> LOCATION: (1)..(24)

<400> SEQUENCE: 25 att act aat act ggt gga agt att                                     24
Ile Thr Asn Thr Gly Gly Ser Ile
1               5

<210> SEQ ID NO 26
<211> LENGTH: 8
<212> TYPE: PRT
<213> ORGANISM: Rattus norvegicus

<400> SEQUENCE: 26

Ile Thr Asn Thr Gly Gly Ser Ile
1               5

<210> SEQ ID NO 27
<211> LENGTH: 42
<212> TYPE: DNA
<213> ORGANISM: Rattus norvegicus
<220> FEATURE:
<221> NAME/KEY: CDS
<222> LOCATION: (1)..(42)

<400> SEQUENCE: 27 aca aga gat tcc gac tac gga ggg tat ggg tgg ttt gct tac            42
Thr Arg Asp Ser Asp Tyr Gly Gly Tyr Gly Trp Phe Ala Tyr
1               5                   10

<210> SEQ ID NO 28
<211> LENGTH: 14
<212> TYPE: PRT
<213> ORGANISM: Rattus norvegicus

<400> SEQUENCE: 28

Thr Arg Asp Ser Asp Tyr Gly Gly Tyr Gly Trp Phe Ala Tyr
1               5                   10

<210> SEQ ID NO 29
<211> LENGTH: 18
<212> TYPE: DNA
<213> ORGANISM: Rattus norvegicus
<220> FEATURE:
<221> NAME/KEY: CDS
<222> LOCATION: (1)..(18)

<400> SEQUENCE: 29 cag agt att agc aca agc                                             18
Gln Ser Ile Ser Thr Ser
1               5

<210> SEQ ID NO 30
<211> LENGTH: 6
<212> TYPE: PRT
<213> ORGANISM: Rattus norvegicus

<400> SEQUENCE: 30

Gln Ser Ile Ser Thr Ser
1               5

```
<210> SEQ ID NO 31
<211> LENGTH: 27
<212> TYPE: DNA
<213> ORGANISM: Rattus norvegicus
<220> FEATURE:
<221> NAME/KEY: CDS
<222> LOCATION: (1)..(27)

<400> SEQUENCE: 31 caa cag agt tac agc agc ccg ctc acg                         27
Gln Gln Ser Tyr Ser Ser Pro Leu Thr
1               5

<210> SEQ ID NO 32
<211> LENGTH: 9
<212> TYPE: PRT
<213> ORGANISM: Rattus norvegicus

<400> SEQUENCE: 32

Gln Gln Ser Tyr Ser Ser Pro Leu Thr
1               5

<210> SEQ ID NO 33
<211> LENGTH: 24
<212> TYPE: DNA
<213> ORGANISM: Rattus norvegicus
<220> FEATURE:
<221> NAME/KEY: CDS
<222> LOCATION: (1)..(24)

<400> SEQUENCE: 33 gga ttc act ttc agt aac tat ggc                             24
Gly Phe Thr Phe Ser Asn Tyr Gly
1               5

<210> SEQ ID NO 34
<211> LENGTH: 8
<212> TYPE: PRT
<213> ORGANISM: Rattus norvegicus

<400> SEQUENCE: 34

Gly Phe Thr Phe Ser Asn Tyr Gly
1               5

<210> SEQ ID NO 35
<211> LENGTH: 24
<212> TYPE: DNA
<213> ORGANISM: Rattus norvegicus
<220> FEATURE:
<221> NAME/KEY: CDS
<222> LOCATION: (1)..(24)

<400> SEQUENCE: 35 att agt act agt act ggt agc act                             24
Ile Ser Thr Ser Thr Gly Ser Thr
1               5

<210> SEQ ID NO 36
<211> LENGTH: 8
<212> TYPE: PRT
<213> ORGANISM: Rattus norvegicus

<400> SEQUENCE: 36

Ile Ser Thr Ser Thr Gly Ser Thr
1               5

<210> SEQ ID NO 37
```

```
<211> LENGTH: 33
<212> TYPE: DNA
<213> ORGANISM: Rattus norvegicus
<220> FEATURE:
<221> NAME/KEY: CDS
<222> LOCATION: (1)..(33)

<400> SEQUENCE: 37 aca aat tac tat gat ggt agt tac ttt gat tac                           33
Thr Asn Tyr Tyr Asp Gly Ser Tyr Phe Asp Tyr
1               5                   10

<210> SEQ ID NO 38
<211> LENGTH: 11
<212> TYPE: PRT
<213> ORGANISM: Rattus norvegicus

<400> SEQUENCE: 38

Thr Asn Tyr Tyr Asp Gly Ser Tyr Phe Asp Tyr
1               5                   10

<210> SEQ ID NO 39
<211> LENGTH: 36
<212> TYPE: DNA
<213> ORGANISM: Rattus norvegicus
<220> FEATURE:
<221> NAME/KEY: CDS
<222> LOCATION: (1)..(36)

<400> SEQUENCE: 39 cag aat ctt tta tac agt gga aac caa aag aac tac                       36
Gln Asn Leu Leu Tyr Ser Gly Asn Gln Lys Asn Tyr
1               5                   10

<210> SEQ ID NO 40
<211> LENGTH: 12
<212> TYPE: PRT
<213> ORGANISM: Rattus norvegicus

<400> SEQUENCE: 40

Gln Asn Leu Leu Tyr Ser Gly Asn Gln Lys Asn Tyr
1               5                   10

<210> SEQ ID NO 41
<211> LENGTH: 27
<212> TYPE: DNA
<213> ORGANISM: Rattus norvegicus
<220> FEATURE:
<221> NAME/KEY: CDS
<222> LOCATION: (1)..(27)

<400> SEQUENCE: 41 cag cag tat tat gat act cca ttc acg                                   27
Gln Gln Tyr Tyr Asp Thr Pro Phe Thr
1               5

<210> SEQ ID NO 42
<211> LENGTH: 9
<212> TYPE: PRT
<213> ORGANISM: Rattus norvegicus

<400> SEQUENCE: 42

Gln Gln Tyr Tyr Asp Thr Pro Phe Thr
1               5

<210> SEQ ID NO 43
<211> LENGTH: 24
```

<212> TYPE: DNA
<213> ORGANISM: Rattus norvegicus
<220> FEATURE:
<221> NAME/KEY: CDS
<222> LOCATION: (1)..(24)

<400> SEQUENCE: 43 gga ttc act ttc agt gac tat ggc                            24
Gly Phe Thr Phe Ser Asp Tyr Gly
1               5

<210> SEQ ID NO 44
<211> LENGTH: 8
<212> TYPE: PRT
<213> ORGANISM: Rattus norvegicus

<400> SEQUENCE: 44

Gly Phe Thr Phe Ser Asp Tyr Gly
1               5

<210> SEQ ID NO 45
<211> LENGTH: 24
<212> TYPE: DNA
<213> ORGANISM: Rattus norvegicus
<220> FEATURE:
<221> NAME/KEY: CDS
<222> LOCATION: (1)..(24)

<400> SEQUENCE: 45 att agt tat gat ggt agt agg act                            24
Ile Ser Tyr Asp Gly Ser Arg Thr
1               5

<210> SEQ ID NO 46
<211> LENGTH: 8
<212> TYPE: PRT
<213> ORGANISM: Rattus norvegicus

<400> SEQUENCE: 46

Ile Ser Tyr Asp Gly Ser Arg Thr
1               5

<210> SEQ ID NO 47
<211> LENGTH: 39
<212> TYPE: DNA
<213> ORGANISM: Rattus norvegicus
<220> FEATURE:
<221> NAME/KEY: CDS
<222> LOCATION: (1)..(39)

<400> SEQUENCE: 47 gca aga cat ggg aat tac ttt gat ggt tat tat gat tac        39
Ala Arg His Gly Asn Tyr Phe Asp Gly Tyr Tyr Asp Tyr
1               5                   10

<210> SEQ ID NO 48
<211> LENGTH: 13
<212> TYPE: PRT
<213> ORGANISM: Rattus norvegicus

<400> SEQUENCE: 48

Ala Arg His Gly Asn Tyr Phe Asp Gly Tyr Tyr Asp Tyr
1               5                   10

<210> SEQ ID NO 49
<211> LENGTH: 36
<212> TYPE: DNA

```
<213> ORGANISM: Rattus norvegicus
<220> FEATURE:
<221> NAME/KEY: CDS
<222> LOCATION: (1)..(36)

<400> SEQUENCE: 49 cag agt ctt tta tac agt gga aac caa aag aac tac          36
Gln Ser Leu Leu Tyr Ser Gly Asn Gln Lys Asn Tyr
1               5                   10

<210> SEQ ID NO 50
<211> LENGTH: 12
<212> TYPE: PRT
<213> ORGANISM: Rattus norvegicus

<400> SEQUENCE: 50

Gln Ser Leu Leu Tyr Ser Gly Asn Gln Lys Asn Tyr
1               5                   10

<210> SEQ ID NO 51
<211> LENGTH: 27
<212> TYPE: DNA
<213> ORGANISM: Rattus norvegicus
<220> FEATURE:
<221> NAME/KEY: CDS
<222> LOCATION: (1)..(27)

<400> SEQUENCE: 51 cag cag tat tat gat act cca ttc acg                      27
Gln Gln Tyr Tyr Asp Thr Pro Phe Thr
1               5

<210> SEQ ID NO 52
<211> LENGTH: 9
<212> TYPE: PRT
<213> ORGANISM: Rattus norvegicus

<400> SEQUENCE: 52

Gln Gln Tyr Tyr Asp Thr Pro Phe Thr
1               5

<210> SEQ ID NO 53
<211> LENGTH: 24
<212> TYPE: DNA
<213> ORGANISM: Rattus norvegicus
<220> FEATURE:
<221> NAME/KEY: CDS
<222> LOCATION: (1)..(24)

<400> SEQUENCE: 53 gga ttc act ttc agt aac tat tac                          24
Gly Phe Thr Phe Ser Asn Tyr Tyr
1               5

<210> SEQ ID NO 54
<211> LENGTH: 8
<212> TYPE: PRT
<213> ORGANISM: Rattus norvegicus

<400> SEQUENCE: 54

Gly Phe Thr Phe Ser Asn Tyr Tyr
1               5

<210> SEQ ID NO 55
<211> LENGTH: 24
<212> TYPE: DNA
<213> ORGANISM: Rattus norvegicus
```

```
<220> FEATURE:
<221> NAME/KEY: CDS
<222> LOCATION: (1)..(24)

<400> SEQUENCE: 55 att agt aat ggt ggt gat tcc act                                              24
Ile Ser Asn Gly Gly Asp Ser Thr
1               5

<210> SEQ ID NO 56
<211> LENGTH: 8
<212> TYPE: PRT
<213> ORGANISM: Rattus norvegicus

<400> SEQUENCE: 56

Ile Ser Asn Gly Gly Asp Ser Thr
1               5

<210> SEQ ID NO 57
<211> LENGTH: 42
<212> TYPE: DNA
<213> ORGANISM: Rattus norvegicus
<220> FEATURE:
<221> NAME/KEY: CDS
<222> LOCATION: (1)..(42)

<400> SEQUENCE: 57 gca aga cag gac tac ccg agt ata acc ggg gtt ttg aat gcc                     42
Ala Arg Gln Asp Tyr Pro Ser Ile Thr Gly Val Leu Asn Ala
1               5                  10

<210> SEQ ID NO 58
<211> LENGTH: 14
<212> TYPE: PRT
<213> ORGANISM: Rattus norvegicus

<400> SEQUENCE: 58

Ala Arg Gln Asp Tyr Pro Ser Ile Thr Gly Val Leu Asn Ala
1               5                  10

<210> SEQ ID NO 59
<211> LENGTH: 36
<212> TYPE: DNA
<213> ORGANISM: Rattus norvegicus
<220> FEATURE:
<221> NAME/KEY: CDS
<222> LOCATION: (1)..(36)

<400> SEQUENCE: 59 cag agt ctt tta tac agt gga aac caa aag aac tac                             36
Gln Ser Leu Leu Tyr Ser Gly Asn Gln Lys Asn Tyr
1               5                  10

<210> SEQ ID NO 60
<211> LENGTH: 12
<212> TYPE: PRT
<213> ORGANISM: Rattus norvegicus

<400> SEQUENCE: 60

Gln Ser Leu Leu Tyr Ser Gly Asn Gln Lys Asn Tyr
1               5                  10

<210> SEQ ID NO 61
<211> LENGTH: 27
<212> TYPE: DNA
<213> ORGANISM: Rattus norvegicus
<220> FEATURE:
```

```
<221> NAME/KEY: CDS
<222> LOCATION: (1)..(27)

<400> SEQUENCE: 61 cag caa tat tat gat act cca ttc acg                                      27
Gln Gln Tyr Tyr Asp Thr Pro Phe Thr
1               5

<210> SEQ ID NO 62
<211> LENGTH: 9
<212> TYPE: PRT
<213> ORGANISM: Rattus norvegicus

<400> SEQUENCE: 62

Gln Gln Tyr Tyr Asp Thr Pro Phe Thr
1               5

<210> SEQ ID NO 63
<211> LENGTH: 24
<212> TYPE: DNA
<213> ORGANISM: Rattus norvegicus
<220> FEATURE:
<221> NAME/KEY: CDS
<222> LOCATION: (1)..(24)

<400> SEQUENCE: 63 gga ttc act ttc agt aac tat gac                                          24
Gly Phe Thr Phe Ser Asn Tyr Asp
1               5

<210> SEQ ID NO 64
<211> LENGTH: 8
<212> TYPE: PRT
<213> ORGANISM: Rattus norvegicus

<400> SEQUENCE: 64

Gly Phe Thr Phe Ser Asn Tyr Asp
1               5

<210> SEQ ID NO 65
<211> LENGTH: 24
<212> TYPE: DNA
<213> ORGANISM: Rattus norvegicus
<220> FEATURE:
<221> NAME/KEY: CDS
<222> LOCATION: (1)..(24)

<400> SEQUENCE: 65 att agt cct agt ggt ggt agc act                                          24
Ile Ser Pro Ser Gly Gly Ser Thr
1               5

<210> SEQ ID NO 66
<211> LENGTH: 8
<212> TYPE: PRT
<213> ORGANISM: Rattus norvegicus

<400> SEQUENCE: 66

Ile Ser Pro Ser Gly Gly Ser Thr
1               5

<210> SEQ ID NO 67
<211> LENGTH: 48
<212> TYPE: DNA
<213> ORGANISM: Rattus norvegicus
<220> FEATURE:
<221> NAME/KEY: CDS
```

```
<222> LOCATION: (1)..(48)

<400> SEQUENCE: 67 gca aga ctc tat gat ggt agt tat tac cgc tac tgg tac ttt gac ttc    48
Ala Arg Leu Tyr Asp Gly Ser Tyr Tyr Arg Tyr Trp Tyr Phe Asp Phe
1               5                   10                  15

<210> SEQ ID NO 68
<211> LENGTH: 16
<212> TYPE: PRT
<213> ORGANISM: Rattus norvegicus

<400> SEQUENCE: 68

Ala Arg Leu Tyr Asp Gly Ser Tyr Tyr Arg Tyr Trp Tyr Phe Asp Phe
1               5                   10                  15

<210> SEQ ID NO 69
<211> LENGTH: 33
<212> TYPE: DNA
<213> ORGANISM: Rattus norvegicus
<220> FEATURE:
<221> NAME/KEY: CDS
<222> LOCATION: (1)..(33)

<400> SEQUENCE: 69 cag agc ctt gta cac agt gat gga aac acc tac                        33
Gln Ser Leu Val His Ser Asp Gly Asn Thr Tyr
1               5                   10

<210> SEQ ID NO 70
<211> LENGTH: 11
<212> TYPE: PRT
<213> ORGANISM: Rattus norvegicus

<400> SEQUENCE: 70

Gln Ser Leu Val His Ser Asp Gly Asn Thr Tyr
1               5                   10

<210> SEQ ID NO 71
<211> LENGTH: 27
<212> TYPE: DNA
<213> ORGANISM: Rattus norvegicus
<220> FEATURE:
<221> NAME/KEY: CDS
<222> LOCATION: (1)..(27)

<400> SEQUENCE: 71 tta caa agt aca cat ttt cct ctc acg                                27
Leu Gln Ser Thr His Phe Pro Leu Thr
1               5

<210> SEQ ID NO 72
<211> LENGTH: 9
<212> TYPE: PRT
<213> ORGANISM: Rattus norvegicus

<400> SEQUENCE: 72

Leu Gln Ser Thr His Phe Pro Leu Thr
1               5

<210> SEQ ID NO 73
<211> LENGTH: 24
<212> TYPE: DNA
<213> ORGANISM: Rattus norvegicus
<220> FEATURE:
<221> NAME/KEY: CDS
<222> LOCATION: (1)..(24)
```

```
<400> SEQUENCE: 73 gga ttc act ttc agt aac tat tac                                    24
Gly Phe Thr Phe Ser Asn Tyr Tyr
1               5

<210> SEQ ID NO 74
<211> LENGTH: 8
<212> TYPE: PRT
<213> ORGANISM: Rattus norvegicus

<400> SEQUENCE: 74

Gly Phe Thr Phe Ser Asn Tyr Tyr
1               5

<210> SEQ ID NO 75
<211> LENGTH: 24
<212> TYPE: DNA
<213> ORGANISM: Rattus norvegicus
<220> FEATURE:
<221> NAME/KEY: CDS
<222> LOCATION: (1)..(24)

<400> SEQUENCE: 75 att agt aat ggt ggt gga aat act                                    24
Ile Ser Asn Gly Gly Gly Asn Thr
1               5

<210> SEQ ID NO 76
<211> LENGTH: 8
<212> TYPE: PRT
<213> ORGANISM: Rattus norvegicus

<400> SEQUENCE: 76

Ile Ser Asn Gly Gly Gly Asn Thr
1               5

<210> SEQ ID NO 77
<211> LENGTH: 42
<212> TYPE: DNA
<213> ORGANISM: Rattus norvegicus
<220> FEATURE:
<221> NAME/KEY: CDS
<222> LOCATION: (1)..(42)

<400> SEQUENCE: 77 gca aga cag gac tac ccg gct ata acc ggg gtt atg gat gcc            42
Ala Arg Gln Asp Tyr Pro Ala Ile Thr Gly Val Met Asp Ala
1               5                   10

<210> SEQ ID NO 78
<211> LENGTH: 14
<212> TYPE: PRT
<213> ORGANISM: Rattus norvegicus

<400> SEQUENCE: 78

Ala Arg Gln Asp Tyr Pro Ala Ile Thr Gly Val Met Asp Ala
1               5                   10

<210> SEQ ID NO 79
<211> LENGTH: 36
<212> TYPE: DNA
<213> ORGANISM: Rattus norvegicus
<220> FEATURE:
<221> NAME/KEY: CDS
<222> LOCATION: (1)..(36)
```

```
<400> SEQUENCE: 79 cag agt ctt tta tac agt gga aac caa aag acc tac                   36
Gln Ser Leu Leu Tyr Ser Gly Asn Gln Lys Thr Tyr
1               5                   10

<210> SEQ ID NO 80
<211> LENGTH: 12
<212> TYPE: PRT
<213> ORGANISM: Rattus norvegicus

<400> SEQUENCE: 80

Gln Ser Leu Leu Tyr Ser Gly Asn Gln Lys Thr Tyr
1               5                   10

<210> SEQ ID NO 81
<211> LENGTH: 27
<212> TYPE: DNA
<213> ORGANISM: Rattus norvegicus
<220> FEATURE:
<221> NAME/KEY: CDS
<222> LOCATION: (1)..(27)

<400> SEQUENCE: 81 cag caa tat tat gat act cca ttc acg                               27
Gln Gln Tyr Tyr Asp Thr Pro Phe Thr
1               5

<210> SEQ ID NO 82
<211> LENGTH: 9
<212> TYPE: PRT
<213> ORGANISM: Rattus norvegicus

<400> SEQUENCE: 82

Gln Gln Tyr Tyr Asp Thr Pro Phe Thr
1               5

<210> SEQ ID NO 83
<211> LENGTH: 876
<212> TYPE: DNA
<213> ORGANISM: Mus musculus
<220> FEATURE:
<221> NAME/KEY: CDS
<222> LOCATION: (1)..(876)

<400> SEQUENCE: 83 atg aga cgc gcg gcg ctc tgg ctc tgg ctc tgc gcg ctg gcg ctg cgc   48
Met Arg Arg Ala Ala Leu Trp Leu Trp Leu Cys Ala Leu Ala Leu Arg
1               5                   10                  15 ctg cag cct gcc ctc ccg caa att gtg gct gta aat gtt cct cct gaa   96
Leu Gln Pro Ala Leu Pro Gln Ile Val Ala Val Asn Val Pro Pro Glu
            20                  25                  30 gat cag gat ggc tct ggg gat gac tct gac aac ttc tct ggc tct ggc   144
Asp Gln Asp Gly Ser Gly Asp Asp Ser Asp Asn Phe Ser Gly Ser Gly
        35                  40                  45 aca ggt gct ttg cca gat act ttg tca cgg cag aca cct tcc act tgg   192
Thr Gly Ala Leu Pro Asp Thr Leu Ser Arg Gln Thr Pro Ser Thr Trp
    50                  55                  60 aag gac gtg tgg ctg ttg aca gcc acg ccc aca gct cca gag ccc acc   240
Lys Asp Val Trp Leu Leu Thr Ala Thr Pro Thr Ala Pro Glu Pro Thr
65                  70                  75                  80 agc agc aac acc gag act gct ttt acc tct gtc ctg cca gcc gga gag   288
Ser Ser Asn Thr Glu Thr Ala Phe Thr Ser Val Leu Pro Ala Gly Glu
                85                  90                  95 aag ccc gag gag gga gag cct gtg ctc cat gta gaa gca gag cct ggc   336
```

| | | | | | | | | | | | | | | | |
|---|---|---|---|---|---|---|---|---|---|---|---|---|---|---|---|
|Lys|Pro|Glu|Glu<br>100|Gly|Glu|Pro|Val|Leu<br>105|His|Val|Glu|Ala|Glu<br>110|Pro|Gly|

```
ttc act gct cgg gac aag gaa aag gag gtc acc acc agg ccc agg gag    384
Phe Thr Ala Arg Asp Lys Glu Lys Glu Val Thr Thr Arg Pro Arg Glu
        115                 120                 125 acc gtg cag ctc ccc atc acc caa cgg gcc tca aca gtc aga gtc acc    432
Thr Val Gln Leu Pro Ile Thr Gln Arg Ala Ser Thr Val Arg Val Thr
130                 135                 140 aca gcc cag gca gct gtc aca tct cat ccg cac ggg ggc atg caa cct    480
Thr Ala Gln Ala Ala Val Thr Ser His Pro His Gly Gly Met Gln Pro
145                 150                 155                 160 ggc ctc cat gag acc tcg gct ccc aca gca cct ggt caa cct gac cat    528
Gly Leu His Glu Thr Ser Ala Pro Thr Ala Pro Gly Gln Pro Asp His
        165                 170                 175 cag cct cca cgt gtg gag ggt ggc ggc act tct gtc atc aaa gag gtt    576
Gln Pro Pro Arg Val Glu Gly Gly Gly Thr Ser Val Ile Lys Glu Val
        180                 185                 190 gtc gag gat gga act gcc aat cag ctt ccc gca gga gag ggc tct gga    624
Val Glu Asp Gly Thr Ala Asn Gln Leu Pro Ala Gly Glu Gly Ser Gly
        195                 200                 205 gaa caa gac ttc acc ttt gaa aca tct ggg gag aac aca gct gtg gct    672
Glu Gln Asp Phe Thr Phe Glu Thr Ser Gly Glu Asn Thr Ala Val Ala
210                 215                 220 gcc gta gag ccc ggc ctg cgg aat cag ccc ccg gtg gac gaa gga gcc    720
Ala Val Glu Pro Gly Leu Arg Asn Gln Pro Pro Val Asp Glu Gly Ala
225                 230                 235                 240 aca ggt gct tct cag agc ctt ttg gac agg aag aat tct gca gat atc    768
Thr Gly Ala Ser Gln Ser Leu Leu Asp Arg Lys Asn Ser Ala Asp Ile
        245                 250                 255 cag cac agt ggc ggc cgc tcg agt cta gag ggc ccg cgg ttc gaa caa    816
Gln His Ser Gly Gly Arg Ser Ser Leu Glu Gly Pro Arg Phe Glu Gln
        260                 265                 270 aaa ctc atc tca gaa gag gat ctg aat atg cat acc ggt cat cat cac    864
Lys Leu Ile Ser Glu Glu Asp Leu Asn Met His Thr Gly His His His
        275                 280                 285 cat cac cat tga                                                    876
His His His
    290

<210> SEQ ID NO 84
<211> LENGTH: 291
<212> TYPE: PRT
<213> ORGANISM: Mus musculus

<400> SEQUENCE: 84

Met Arg Arg Ala Ala Leu Trp Leu Trp Leu Cys Ala Leu Ala Leu Arg
1               5                   10                  15

Leu Gln Pro Ala Leu Pro Gln Ile Val Ala Val Asn Val Pro Pro Glu
            20                  25                  30

Asp Gln Asp Gly Ser Gly Asp Asp Ser Asp Asn Phe Ser Gly Ser Gly
        35                  40                  45

Thr Gly Ala Leu Pro Asp Thr Leu Ser Arg Gln Thr Pro Ser Thr Trp
    50                  55                  60

Lys Asp Val Trp Leu Leu Thr Ala Thr Pro Thr Ala Pro Glu Pro Thr
65                  70                  75                  80

Ser Ser Asn Thr Glu Thr Ala Phe Thr Ser Val Leu Pro Ala Gly Glu
                85                  90                  95

Lys Pro Glu Glu Gly Glu Pro Val Leu His Val Glu Ala Glu Pro Gly
            100                 105                 110
```

```
Phe Thr Ala Arg Asp Lys Glu Lys Glu Val Thr Thr Arg Pro Arg Glu
            115                 120                 125

Thr Val Gln Leu Pro Ile Thr Gln Arg Ala Ser Thr Val Arg Val Thr
    130                 135                 140

Thr Ala Gln Ala Ala Val Thr Ser His Pro His Gly Gly Met Gln Pro
145                 150                 155                 160

Gly Leu His Glu Thr Ser Ala Pro Thr Ala Pro Gly Gln Pro Asp His
                165                 170                 175

Gln Pro Pro Arg Val Glu Gly Gly Thr Ser Val Ile Lys Glu Val
            180                 185                 190

Val Glu Asp Gly Thr Ala Asn Gln Leu Pro Ala Gly Gly Ser Gly
        195                 200                 205

Glu Gln Asp Phe Thr Phe Glu Thr Ser Gly Glu Asn Thr Ala Val Ala
        210                 215                 220

Ala Val Glu Pro Gly Leu Arg Asn Gln Pro Val Asp Glu Gly Ala
225                 230                 235                 240

Thr Gly Ala Ser Gln Ser Leu Leu Asp Arg Lys Asn Ser Ala Asp Ile
                245                 250                 255

Gln His Ser Gly Gly Arg Ser Ser Leu Glu Gly Pro Arg Phe Glu Gln
            260                 265                 270

Lys Leu Ile Ser Glu Glu Asp Leu Asn Met His Thr Gly His His His
            275                 280                 285

His His His
    290

<210> SEQ ID NO 85
<211> LENGTH: 1050
<212> TYPE: DNA
<213> ORGANISM: Homo sapiens
<220> FEATURE:
<221> NAME/KEY: CDS
<222> LOCATION: (1)..(1050)

<400> SEQUENCE: 85
```

| | | | | | | | | | | | | | | | | |
|---|---|---|---|---|---|---|---|---|---|---|---|---|---|---|---|---|
| atg | ggg | acc | tct | ccg | agc | agc | agc | acc | gcc | ctc | gcc | tcc | tgc | agc | cgc | 48 |
| Met | Gly | Thr | Ser | Pro | Ser | Ser | Ser | Thr | Ala | Leu | Ala | Ser | Cys | Ser | Arg | |
| 1 | | | | 5 | | | | | 10 | | | | | 15 | | |
| atc | gcc | cgc | cga | gcc | aca | gcc | acg | atg | atc | gcg | ggc | tcc | ctt | ctc | ctg | 96 |
| Ile | Ala | Arg | Arg | Ala | Thr | Ala | Thr | Met | Ile | Ala | Gly | Ser | Leu | Leu | Leu | |
| | | | 20 | | | | | 25 | | | | | 30 | | | |
| ctt | gga | ttc | ctt | agc | acc | acc | aca | gct | cag | cca | gaa | cag | aag | gcc | tcg | 144 |
| Leu | Gly | Phe | Leu | Ser | Thr | Thr | Thr | Ala | Gln | Pro | Glu | Gln | Lys | Ala | Ser | |
| | | 35 | | | | | 40 | | | | | 45 | | | | |
| aat | ctc | att | ggc | aca | tac | cgc | cat | gtt | gac | cgt | gcc | acc | ggc | cag | gtg | 192 |
| Asn | Leu | Ile | Gly | Thr | Tyr | Arg | His | Val | Asp | Arg | Ala | Thr | Gly | Gln | Val | |
| | 50 | | | | | 55 | | | | | 60 | | | | | |
| cta | acc | tgt | gac | aag | tgt | cca | gca | gga | acc | tat | gtc | tct | gag | cat | tgt | 240 |
| Leu | Thr | Cys | Asp | Lys | Cys | Pro | Ala | Gly | Thr | Tyr | Val | Ser | Glu | His | Cys | |
| 65 | | | | | 70 | | | | | 75 | | | | | 80 | |
| acc | aac | aca | agc | ctg | cgc | gtc | tgc | agc | agt | tgc | cct | gtg | ggg | acc | ttt | 288 |
| Thr | Asn | Thr | Ser | Leu | Arg | Val | Cys | Ser | Ser | Cys | Pro | Val | Gly | Thr | Phe | |
| | | | | 85 | | | | | 90 | | | | | 95 | | |
| acc | agg | cat | gag | aat | ggc | ata | gag | aaa | tgc | cat | gac | tgt | agt | cag | cca | 336 |
| Thr | Arg | His | Glu | Asn | Gly | Ile | Glu | Lys | Cys | His | Asp | Cys | Ser | Gln | Pro | |
| | | | | 100 | | | | | 105 | | | | | 110 | | |
| tgc | cca | tgg | cca | atg | att | gag | aaa | tta | cct | tgt | gct | gcc | ttg | act | gac | 384 |
| Cys | Pro | Trp | Pro | Met | Ile | Glu | Lys | Leu | Pro | Cys | Ala | Ala | Leu | Thr | Asp | |
| | | | | 115 | | | | | 120 | | | | | 125 | | |

| | | | | | | | | | | | | | | | | |
|---|---|---|---|---|---|---|---|---|---|---|---|---|---|---|---|---|
| cga | gaa | tgc | act | tgc | cca | cct | ggc | atg | ttc | cag | tct | aac | gct | acc | tgt | 432 |
| Arg | Glu | Cys | Thr | Cys | Pro | Pro | Gly | Met | Phe | Gln | Ser | Asn | Ala | Thr | Cys | |
| | 130 | | | | 135 | | | | | 140 | | | | | | |
| gcc | ccc | cat | acg | gtg | tgt | cct | gtg | ggt | tgg | ggt | gtg | cgg | aag | aaa | ggg | 480 |
| Ala | Pro | His | Thr | Val | Cys | Pro | Val | Gly | Trp | Gly | Val | Arg | Lys | Lys | Gly | |
| 145 | | | | | 150 | | | | | 155 | | | | | 160 | |
| aca | gag | act | gag | gat | gtg | cgg | tgt | aag | cag | tgt | gct | cgg | ggt | acc | ttc | 528 |
| Thr | Glu | Thr | Glu | Asp | Val | Arg | Cys | Lys | Gln | Cys | Ala | Arg | Gly | Thr | Phe | |
| | | | | 165 | | | | | 170 | | | | | 175 | | |
| tca | gat | gtg | cct | tct | agt | gtg | atg | aaa | tgc | aaa | gca | tac | aca | gac | tgt | 576 |
| Ser | Asp | Val | Pro | Ser | Ser | Val | Met | Lys | Cys | Lys | Ala | Tyr | Thr | Asp | Cys | |
| | | | 180 | | | | | 185 | | | | | 190 | | | |
| ctg | agt | cag | aac | ctg | gtg | gtg | atc | aag | ccg | ggg | acc | aag | gag | aca | gac | 624 |
| Leu | Ser | Gln | Asn | Leu | Val | Val | Ile | Lys | Pro | Gly | Thr | Lys | Glu | Thr | Asp | |
| | | 195 | | | | | 200 | | | | | 205 | | | | |
| aac | gtc | tgt | ggc | aca | ctc | ccg | tcc | ttc | tcc | agc | tcc | acc | tca | cct | tcc | 672 |
| Asn | Val | Cys | Gly | Thr | Leu | Pro | Ser | Phe | Ser | Ser | Ser | Thr | Ser | Pro | Ser | |
| | 210 | | | | 215 | | | | | 220 | | | | | | |
| cct | ggc | aca | gcc | atc | ttt | cca | cgc | cct | gag | cac | atg | gaa | acc | cat | gaa | 720 |
| Pro | Gly | Thr | Ala | Ile | Phe | Pro | Arg | Pro | Glu | His | Met | Glu | Thr | His | Glu | |
| 225 | | | | | 230 | | | | | 235 | | | | | 240 | |
| gtc | cct | tcc | tcc | act | tat | gtt | ccc | aaa | ggc | atg | aac | tca | aca | gaa | tcc | 768 |
| Val | Pro | Ser | Ser | Thr | Tyr | Val | Pro | Lys | Gly | Met | Asn | Ser | Thr | Glu | Ser | |
| | | | | 245 | | | | | 250 | | | | | 255 | | |
| aac | tct | tct | gcc | tct | gtt | aga | cca | aag | gta | ctg | agt | agc | atc | cag | gaa | 816 |
| Asn | Ser | Ser | Ala | Ser | Val | Arg | Pro | Lys | Val | Leu | Ser | Ser | Ile | Gln | Glu | |
| | | | 260 | | | | | 265 | | | | | 270 | | | |
| ggg | aca | gtc | cct | gac | aac | aca | agc | tca | gca | agg | ggg | aag | gaa | gac | gtg | 864 |
| Gly | Thr | Val | Pro | Asp | Asn | Thr | Ser | Ser | Ala | Arg | Gly | Lys | Glu | Asp | Val | |
| | | 275 | | | | | 280 | | | | | 285 | | | | |
| aac | aag | acc | ctc | cca | aac | ctt | cag | gta | gtc | aac | cac | cag | caa | ggc | ccc | 912 |
| Asn | Lys | Thr | Leu | Pro | Asn | Leu | Gln | Val | Val | Asn | His | Gln | Gln | Gly | Pro | |
| | 290 | | | | 295 | | | | | 300 | | | | | | |
| cac | cac | aga | cac | atc | ctg | aag | ctg | ctg | ccg | tcc | atg | gag | gcc | act | ggg | 960 |
| His | His | Arg | His | Ile | Leu | Lys | Leu | Leu | Pro | Ser | Met | Glu | Ala | Thr | Gly | |
| 305 | | | | | 310 | | | | | 315 | | | | | 320 | |
| ggc | gag | aag | tcc | agc | acg | ccc | atc | aag | ggc | ccc | aag | agg | gga | cat | cct | 1008 |
| Gly | Glu | Lys | Ser | Ser | Thr | Pro | Ile | Lys | Gly | Pro | Lys | Arg | Gly | His | Pro | |
| | | | | 325 | | | | | 330 | | | | | 335 | | |
| aga | cag | aac | cta | cac | aag | cat | ttt | gac | atc | aat | gag | cat | ttg | | | 1050 |
| Arg | Gln | Asn | Leu | His | Lys | His | Phe | Asp | Ile | Asn | Glu | His | Leu | | | |
| | | | 340 | | | | | 345 | | | | | 350 | | | |

<210> SEQ ID NO 86
<211> LENGTH: 350
<212> TYPE: PRT
<213> ORGANISM: Homo sapiens

<400> SEQUENCE: 86

| | | | | | | | | | | | | | | | |
|---|---|---|---|---|---|---|---|---|---|---|---|---|---|---|---|
| Met | Gly | Thr | Ser | Pro | Ser | Ser | Thr | Ala | Leu | Ala | Ser | Cys | Ser | Arg | |
| 1 | | | | 5 | | | | | 10 | | | | | 15 | |

| | | | | | | | | | | | | | | |
|---|---|---|---|---|---|---|---|---|---|---|---|---|---|---|
| Ile | Ala | Arg | Arg | Ala | Thr | Ala | Thr | Met | Ile | Ala | Gly | Ser | Leu | Leu | Leu |
| | | | 20 | | | | | 25 | | | | | 30 | | |

| | | | | | | | | | | | | | | |
|---|---|---|---|---|---|---|---|---|---|---|---|---|---|---|
| Leu | Gly | Phe | Leu | Ser | Thr | Thr | Thr | Ala | Gln | Pro | Glu | Gln | Lys | Ala | Ser |
| | | 35 | | | | | 40 | | | | | 45 | | | |

| | | | | | | | | | | | | | | |
|---|---|---|---|---|---|---|---|---|---|---|---|---|---|---|
| Asn | Leu | Ile | Gly | Thr | Tyr | Arg | His | Val | Asp | Arg | Ala | Thr | Gly | Gln | Val |
| | 50 | | | | | 55 | | | | | 60 | | | | |

| | | | | | | | | | | | | | | | |
|---|---|---|---|---|---|---|---|---|---|---|---|---|---|---|---|
| Leu | Thr | Cys | Asp | Lys | Cys | Pro | Ala | Gly | Thr | Tyr | Val | Ser | Glu | His | Cys |
| 65 | | | | | 70 | | | | | 75 | | | | | 80 |

```
Thr Asn Thr Ser Leu Arg Val Cys Ser Ser Cys Pro Val Gly Thr Phe
                85                  90                  95

Thr Arg His Glu Asn Gly Ile Glu Lys Cys His Asp Cys Ser Gln Pro
            100                 105                 110

Cys Pro Trp Pro Met Ile Glu Lys Leu Pro Cys Ala Ala Leu Thr Asp
        115                 120                 125

Arg Glu Cys Thr Cys Pro Pro Gly Met Phe Gln Ser Asn Ala Thr Cys
    130                 135                 140

Ala Pro His Thr Val Cys Pro Val Gly Trp Gly Val Arg Lys Lys Gly
145                 150                 155                 160

Thr Glu Thr Glu Asp Val Arg Cys Lys Gln Cys Ala Arg Gly Thr Phe
                165                 170                 175

Ser Asp Val Pro Ser Ser Val Met Lys Cys Lys Ala Tyr Thr Asp Cys
            180                 185                 190

Leu Ser Gln Asn Leu Val Val Ile Lys Pro Gly Thr Lys Glu Thr Asp
        195                 200                 205

Asn Val Cys Gly Thr Leu Pro Ser Phe Ser Ser Ser Thr Ser Pro Ser
    210                 215                 220

Pro Gly Thr Ala Ile Phe Pro Arg Pro Glu His Met Glu Thr His Glu
225                 230                 235                 240

Val Pro Ser Ser Thr Tyr Val Pro Lys Gly Met Asn Ser Thr Glu Ser
                245                 250                 255

Asn Ser Ser Ala Ser Val Arg Pro Lys Val Leu Ser Ser Ile Gln Glu
            260                 265                 270

Gly Thr Val Pro Asp Asn Thr Ser Ser Ala Arg Gly Lys Glu Asp Val
        275                 280                 285

Asn Lys Thr Leu Pro Asn Leu Gln Val Val Asn His Gln Gln Gly Pro
    290                 295                 300

His His Arg His Ile Leu Lys Leu Leu Pro Ser Met Glu Ala Thr Gly
305                 310                 315                 320

Gly Glu Lys Ser Ser Thr Pro Ile Lys Gly Pro Lys Arg Gly His Pro
                325                 330                 335

Arg Gln Asn Leu His Lys His Phe Asp Ile Asn Glu His Leu
            340                 345                 350

<210> SEQ ID NO 87
<211> LENGTH: 1050
<212> TYPE: DNA
<213> ORGANISM: Mus musculus
<220> FEATURE:
<221> NAME/KEY: CDS
<222> LOCATION: (1)..(1050)

<400> SEQUENCE: 87 atg ggg acc cgg gca agc agc atc acc gcc ctc gcc tct tgc agc cgc     48
Met Gly Thr Arg Ala Ser Ser Ile Thr Ala Leu Ala Ser Cys Ser Arg
1               5                   10                  15 acc gcc ggc caa gtc gga gcc acg atg gtc gcc ggc tct ctt ctc ctg     96
Thr Ala Gly Gln Val Gly Ala Thr Met Val Ala Gly Ser Leu Leu Leu
            20                  25                  30 ctt gga ttc ctc agc acc atc aca gct caa cca gaa caa aag act ctg    144
Leu Gly Phe Leu Ser Thr Ile Thr Ala Gln Pro Glu Gln Lys Thr Leu
        35                  40                  45 agt ctc cct ggc acc tac cgc cat gtt gac cgt acc act ggc cag gtg    192
Ser Leu Pro Gly Thr Tyr Arg His Val Asp Arg Thr Thr Gly Gln Val
    50                  55                  60
```

| | | | | | | | | | | | | | | | | |
|---|---|---|---|---|---|---|---|---|---|---|---|---|---|---|---|---|
| cta | acc | tgc | gac | aag | tgc | cca | gca | gga | acg | tac | gtc | tcc | gag | cac | tgt | 240 |
| Leu | Thr | Cys | Asp | Lys | Cys | Pro | Ala | Gly | Thr | Tyr | Val | Ser | Glu | His | Cys | |
| 65 | | | | 70 | | | | | 75 | | | | | 80 | | |
| acc | aac | atg | agc | ctg | cga | gtc | tgc | agc | agc | tgc | ccc | gcg | ggg | acc | ttt | 288 |
| Thr | Asn | Met | Ser | Leu | Arg | Val | Cys | Ser | Ser | Cys | Pro | Ala | Gly | Thr | Phe | |
| | | | | 85 | | | | | 90 | | | | | 95 | | |
| acc | agg | cac | gag | aac | ggc | ata | gag | aga | tgc | cat | gac | tgt | agt | cag | cca | 336 |
| Thr | Arg | His | Glu | Asn | Gly | Ile | Glu | Arg | Cys | His | Asp | Cys | Ser | Gln | Pro | |
| | | | 100 | | | | | 105 | | | | | 110 | | | |
| tgt | cca | tgg | ccg | atg | att | gag | aga | tta | cct | tgt | gct | gcc | ttg | act | gac | 384 |
| Cys | Pro | Trp | Pro | Met | Ile | Glu | Arg | Leu | Pro | Cys | Ala | Ala | Leu | Thr | Asp | |
| | | | 115 | | | | | 120 | | | | | 125 | | | |
| cga | gag | tgc | atc | tgc | cca | cct | gga | atg | tat | cag | tct | aat | ggt | acc | tgc | 432 |
| Arg | Glu | Cys | Ile | Cys | Pro | Pro | Gly | Met | Tyr | Gln | Ser | Asn | Gly | Thr | Cys | |
| | 130 | | | | | 135 | | | | | 140 | | | | | |
| gct | ccc | cat | aca | gtg | tgc | ccc | gtg | ggc | tgg | ggt | gtg | cgg | aag | aaa | ggg | 480 |
| Ala | Pro | His | Thr | Val | Cys | Pro | Val | Gly | Trp | Gly | Val | Arg | Lys | Lys | Gly | |
| 145 | | | | | 150 | | | | | 155 | | | | | 160 | |
| aca | gag | aat | gaa | gat | gtg | cgc | tgt | aag | cag | tgc | gct | cgg | ggt | acc | ttc | 528 |
| Thr | Glu | Asn | Glu | Asp | Val | Arg | Cys | Lys | Gln | Cys | Ala | Arg | Gly | Thr | Phe | |
| | | | | 165 | | | | | 170 | | | | | 175 | | |
| tct | gac | gtg | cct | tcc | agt | gtg | atg | aag | tgt | aaa | gct | cac | acg | gac | tgt | 576 |
| Ser | Asp | Val | Pro | Ser | Ser | Val | Met | Lys | Cys | Lys | Ala | His | Thr | Asp | Cys | |
| | | | 180 | | | | | 185 | | | | | 190 | | | |
| ctg | ggt | cag | aac | ctg | gag | gtg | gtc | aag | cca | ggg | acc | aag | gag | aca | gac | 624 |
| Leu | Gly | Gln | Asn | Leu | Glu | Val | Val | Lys | Pro | Gly | Thr | Lys | Glu | Thr | Asp | |
| | | | 195 | | | | | 200 | | | | | 205 | | | |
| aac | gtc | tgt | ggc | atg | cgc | ctg | ttc | ttc | tcc | agc | aca | aac | cca | cct | tcc | 672 |
| Asn | Val | Cys | Gly | Met | Arg | Leu | Phe | Phe | Ser | Ser | Thr | Asn | Pro | Pro | Ser | |
| | 210 | | | | | 215 | | | | | 220 | | | | | |
| tct | ggc | aca | gtt | acc | ttt | tct | cac | cct | gag | cat | atg | gaa | tcc | cac | gat | 720 |
| Ser | Gly | Thr | Val | Thr | Phe | Ser | His | Pro | Glu | His | Met | Glu | Ser | His | Asp | |
| 225 | | | | | 230 | | | | | 235 | | | | | 240 | |
| gtc | cct | tcc | tcc | acc | tat | gag | ccc | caa | ggc | atg | aac | tca | aca | gat | tcc | 768 |
| Val | Pro | Ser | Ser | Thr | Tyr | Glu | Pro | Gln | Gly | Met | Asn | Ser | Thr | Asp | Ser | |
| | | | | 245 | | | | | 250 | | | | | 255 | | |
| aac | tct | act | gcc | tct | gtt | aga | act | aag | gta | cca | agt | ggc | atc | gag | gaa | 816 |
| Asn | Ser | Thr | Ala | Ser | Val | Arg | Thr | Lys | Val | Pro | Ser | Gly | Ile | Glu | Glu | |
| | | | 260 | | | | | 265 | | | | | 270 | | | |
| ggg | aca | gtg | cct | gac | aat | acg | agc | tca | acc | agt | ggg | aag | gaa | ggc | act | 864 |
| Gly | Thr | Val | Pro | Asp | Asn | Thr | Ser | Ser | Thr | Ser | Gly | Lys | Glu | Gly | Thr | |
| | | 275 | | | | | 280 | | | | | 285 | | | | |
| aat | agg | acc | ctg | cca | aac | cca | cca | caa | gtt | acc | cac | cag | caa | gcc | ccc | 912 |
| Asn | Arg | Thr | Leu | Pro | Asn | Pro | Pro | Gln | Val | Thr | His | Gln | Gln | Ala | Pro | |
| | 290 | | | | | 295 | | | | | 300 | | | | | |
| cac | cac | aga | cac | att | ctg | aag | ctg | ctg | cca | tcg | tcc | atg | gag | gcc | acg | 960 |
| His | His | Arg | His | Ile | Leu | Lys | Leu | Leu | Pro | Ser | Ser | Met | Glu | Ala | Thr | |
| 305 | | | | | 310 | | | | | 315 | | | | | 320 | |
| ggt | gag | aag | tcc | agc | aca | gcc | atc | aag | gcc | ccc | aag | agg | ggt | cac | ccc | 1008 |
| Gly | Glu | Lys | Ser | Ser | Thr | Ala | Ile | Lys | Ala | Pro | Lys | Arg | Gly | His | Pro | |
| | | | | 325 | | | | | 330 | | | | | 335 | | |
| aga | cag | aac | gct | cac | aag | cat | ttc | gac | atc | aac | gag | cac | ttg | | | 1050 |
| Arg | Gln | Asn | Ala | His | Lys | His | Phe | Asp | Ile | Asn | Glu | His | Leu | | | |
| | | 340 | | | | | 345 | | | | | 350 | | | | |

<210> SEQ ID NO 88
<211> LENGTH: 350
<212> TYPE: PRT
<213> ORGANISM: Mus musculus

<400> SEQUENCE: 88

```
Met Gly Thr Arg Ala Ser Ser Ile Thr Ala Leu Ala Ser Cys Ser Arg
1               5                   10                  15

Thr Ala Gly Gln Val Gly Ala Thr Met Val Ala Gly Ser Leu Leu Leu
            20                  25                  30

Leu Gly Phe Leu Ser Thr Ile Thr Ala Gln Pro Glu Gln Lys Thr Leu
        35                  40                  45

Ser Leu Pro Gly Thr Tyr Arg His Val Asp Arg Thr Thr Gly Gln Val
    50                  55                  60

Leu Thr Cys Asp Lys Cys Pro Ala Gly Thr Tyr Val Ser Glu His Cys
65                  70                  75                  80

Thr Asn Met Ser Leu Arg Val Cys Ser Ser Cys Pro Ala Gly Thr Phe
                85                  90                  95

Thr Arg His Glu Asn Gly Ile Glu Arg Cys His Asp Cys Ser Gln Pro
            100                 105                 110

Cys Pro Trp Pro Met Ile Glu Arg Leu Pro Cys Ala Ala Leu Thr Asp
        115                 120                 125

Arg Glu Cys Ile Cys Pro Pro Gly Met Tyr Gln Ser Asn Gly Thr Cys
    130                 135                 140

Ala Pro His Thr Val Cys Pro Val Gly Trp Gly Val Arg Lys Lys Gly
145                 150                 155                 160

Thr Glu Asn Glu Asp Val Arg Cys Lys Gln Cys Ala Arg Gly Thr Phe
                165                 170                 175

Ser Asp Val Pro Ser Ser Val Met Lys Cys Lys Ala His Thr Asp Cys
            180                 185                 190

Leu Gly Gln Asn Leu Glu Val Val Lys Pro Gly Thr Lys Glu Thr Asp
        195                 200                 205

Asn Val Cys Gly Met Arg Leu Phe Phe Ser Ser Thr Asn Pro Pro Ser
210                 215                 220

Ser Gly Thr Val Thr Phe Ser His Pro Glu His Met Glu Ser His Asp
225                 230                 235                 240

Val Pro Ser Ser Thr Tyr Glu Pro Gln Gly Met Asn Ser Thr Asp Ser
                245                 250                 255

Asn Ser Thr Ala Ser Val Arg Thr Lys Val Pro Ser Gly Ile Glu Glu
            260                 265                 270

Gly Thr Val Pro Asp Asn Thr Ser Ser Thr Ser Gly Lys Glu Gly Thr
        275                 280                 285

Asn Arg Thr Leu Pro Asn Pro Pro Gln Val Thr His Gln Gln Ala Pro
    290                 295                 300

His His Arg His Ile Leu Lys Leu Leu Pro Ser Ser Met Glu Ala Thr
305                 310                 315                 320

Gly Glu Lys Ser Ser Thr Ala Ile Lys Ala Pro Lys Arg Gly His Pro
                325                 330                 335

Arg Gln Asn Ala His Lys His Phe Asp Ile Asn Glu His Leu
            340                 345                 350

<210> SEQ ID NO 89
<211> LENGTH: 930
<212> TYPE: DNA
<213> ORGANISM: Mus musculus
<220> FEATURE:
<221> NAME/KEY: CDS
<222> LOCATION: (1)..(930)

<400> SEQUENCE: 89 atg ggg acc cgg gca agc agc atc acc gcc ctc gcc tct tgc agc cgc        48
```

```
Met Gly Thr Arg Ala Ser Ser Ile Thr Ala Leu Ala Ser Cys Ser Arg
1               5                   10                  15 acc gcc ggc caa gtc gga gcc acg atg gtc gcc ggc tct ctt ctc ctg    96
Thr Ala Gly Gln Val Gly Ala Thr Met Val Ala Gly Ser Leu Leu Leu
                20                  25                  30 ctt gga ttc ctc agc acc atc aca gct caa cca gaa caa aag act ctg   144
Leu Gly Phe Leu Ser Thr Ile Thr Ala Gln Pro Glu Gln Lys Thr Leu
            35                  40                  45 agt ctc cct ggc acc tac cgc cat gtt gac cgt acc act ggc cag gtg   192
Ser Leu Pro Gly Thr Tyr Arg His Val Asp Arg Thr Thr Gly Gln Val
50                  55                  60 cta tgc cat gac tgt agt cag cca tgt cca tgg ccg atg att gag aga   240
Leu Cys His Asp Cys Ser Gln Pro Cys Pro Trp Pro Met Ile Glu Arg
65                  70                  75                  80 tta cct tgt gct gcc ttg act gac cga gag tgc atc tgc cca cct gga   288
Leu Pro Cys Ala Ala Leu Thr Asp Arg Glu Cys Ile Cys Pro Pro Gly
                85                  90                  95 atg tat cag tct aat ggt acc tgc gct ccc cat aca gtg tgc ccc gtg   336
Met Tyr Gln Ser Asn Gly Thr Cys Ala Pro His Thr Val Cys Pro Val
            100                 105                 110 ggc tgg ggt gtg cgg aag aaa ggg aca gag aat gaa gat gtg cgc tgt   384
Gly Trp Gly Val Arg Lys Lys Gly Thr Glu Asn Glu Asp Val Arg Cys
        115                 120                 125 aag cag tgc gct cgg ggt acc ttc tct gac gtg cct tcc agt gtg atg   432
Lys Gln Cys Ala Arg Gly Thr Phe Ser Asp Val Pro Ser Ser Val Met
130                 135                 140 aag tgt aaa gct cac acg gac tgt ctg ggt cag aac ctg gag gtg gtc   480
Lys Cys Lys Ala His Thr Asp Cys Leu Gly Gln Asn Leu Glu Val Val
145                 150                 155                 160 aag cca ggg acc aag gag aca gac aac gtc tgt ggc atg cgc ctg ttc   528
Lys Pro Gly Thr Lys Glu Thr Asp Asn Val Cys Gly Met Arg Leu Phe
                165                 170                 175 ttc tcc agc aca aac cca cct tcc tct ggc aca gtt acc ttt tct cac   576
Phe Ser Ser Thr Asn Pro Pro Ser Ser Gly Thr Val Thr Phe Ser His
            180                 185                 190 cct gag cat atg gaa tcc cac gat gtc cct tcc tcc acc tat gag ccc   624
Pro Glu His Met Glu Ser His Asp Val Pro Ser Ser Thr Tyr Glu Pro
        195                 200                 205 caa ggc atg aac tca aca gat tcc aac tct act gcc tct gtt aga act   672
Gln Gly Met Asn Ser Thr Asp Ser Asn Ser Thr Ala Ser Val Arg Thr
210                 215                 220 aag gta cca agt ggc atc gag gaa ggg aca gtg cct gac aat acg agc   720
Lys Val Pro Ser Gly Ile Glu Glu Gly Thr Val Pro Asp Asn Thr Ser
225                 230                 235                 240 tca acc agt ggg aag gaa ggc act aat agg acc ctg cca aac cca cca   768
Ser Thr Ser Gly Lys Glu Gly Thr Asn Arg Thr Leu Pro Asn Pro Pro
                245                 250                 255 caa gtt acc cac cag caa gcc ccc cac cac aga cac att ctg aag ctg   816
Gln Val Thr His Gln Gln Ala Pro His His Arg His Ile Leu Lys Leu
            260                 265                 270 ctg cca tcg tcc atg gag gcc acg ggt gag aag tcc agc aca gcc atc   864
Leu Pro Ser Ser Met Glu Ala Thr Gly Glu Lys Ser Ser Thr Ala Ile
        275                 280                 285 aag gcc ccc aag agg ggt cac ccc aga cag aac gct cac aag cat ttc   912
Lys Ala Pro Lys Arg Gly His Pro Arg Gln Asn Ala His Lys His Phe
290                 295                 300 gac atc aac gag cac ttg                                           930
Asp Ile Asn Glu His Leu
305             310
```

```
<210> SEQ ID NO 90
<211> LENGTH: 310
<212> TYPE: PRT
<213> ORGANISM: Mus musculus

<400> SEQUENCE: 90

Met Gly Thr Arg Ala Ser Ser Ile Thr Ala Leu Ala Ser Cys Ser Arg
1               5                   10                  15

Thr Ala Gly Gln Val Gly Ala Thr Met Val Ala Gly Ser Leu Leu Leu
            20                  25                  30

Leu Gly Phe Leu Ser Thr Ile Thr Ala Gln Pro Glu Gln Lys Thr Leu
        35                  40                  45

Ser Leu Pro Gly Thr Tyr Arg His Val Asp Arg Thr Thr Gly Gln Val
    50                  55                  60

Leu Cys His Asp Cys Ser Gln Pro Cys Pro Trp Pro Met Ile Glu Arg
65                  70                  75                  80

Leu Pro Cys Ala Ala Leu Thr Asp Arg Glu Cys Ile Cys Pro Pro Gly
                85                  90                  95

Met Tyr Gln Ser Asn Gly Thr Cys Ala Pro His Thr Val Cys Pro Val
            100                 105                 110

Gly Trp Gly Val Arg Lys Lys Gly Thr Glu Asn Glu Asp Val Arg Cys
        115                 120                 125

Lys Gln Cys Ala Arg Gly Thr Phe Ser Asp Val Pro Ser Ser Val Met
130                 135                 140

Lys Cys Lys Ala His Thr Asp Cys Leu Gly Gln Asn Leu Glu Val Val
145                 150                 155                 160

Lys Pro Gly Thr Lys Glu Thr Asp Asn Val Cys Gly Met Arg Leu Phe
                165                 170                 175

Phe Ser Ser Thr Asn Pro Pro Ser Ser Gly Thr Val Thr Phe Ser His
            180                 185                 190

Pro Glu His Met Glu Ser His Asp Val Pro Ser Ser Thr Tyr Glu Pro
        195                 200                 205

Gln Gly Met Asn Ser Thr Asp Ser Asn Ser Thr Ala Ser Val Arg Thr
    210                 215                 220

Lys Val Pro Ser Gly Ile Glu Glu Gly Thr Val Pro Asp Asn Thr Ser
225                 230                 235                 240

Ser Thr Ser Gly Lys Glu Gly Thr Asn Arg Thr Leu Pro Asn Pro Pro
                245                 250                 255

Gln Val Thr His Gln Gln Ala Pro His His Arg His Ile Leu Lys Leu
            260                 265                 270

Leu Pro Ser Ser Met Glu Ala Thr Gly Glu Lys Ser Ser Thr Ala Ile
        275                 280                 285

Lys Ala Pro Lys Arg Gly His Pro Arg Gln Asn Ala His Lys His Phe
    290                 295                 300

Asp Ile Asn Glu His Leu
305                 310
```